(12) United States Patent
Longinotti-Buitoni et al.

(10) Patent No.: US 10,159,440 B2
(45) Date of Patent: Dec. 25, 2018

(54) PHYSIOLOGICAL MONITORING GARMENTS

(71) Applicant: L.I.F.E. CORPORATION S.A., Luxembourg (LU)

(72) Inventors: Gianluigi Longinotti-Buitoni, Riverside, CT (US); Andrea Aliverti, Como (IT)

(73) Assignee: L.I.F.E. Corporation S.A., Luxembourg (LU)

( * ) Notice: Subject to any disclaimer, the term of this patent is extended or adjusted under 35 U.S.C. 154(b) by 31 days.

(21) Appl. No.: 14/644,180

(22) Filed: Mar. 10, 2015

(65) Prior Publication Data

US 2015/0250420 A1   Sep. 10, 2015

Related U.S. Application Data

(63) Continuation-in-part of application No. 14/612,060, filed on Feb. 2, 2015, now Pat. No. 9,986,771, which is a continuation of application No. 14/331,185, filed on Jul. 14, 2014, now Pat. No. 8,945,328.

(60) Provisional application No. 62/097,560, filed on Dec. 29, 2014, provisional application No. 62/080,966, filed on Nov. 17, 2014, provisional application No.
(Continued)

(51) Int. Cl.
| | |
|---|---|
| *A61B 5/00* | (2006.01) |
| *A41D 1/00* | (2018.01) |
| *A61B 5/113* | (2006.01) |
| *A61B 5/0408* | (2006.01) |
| *G01L 1/22* | (2006.01) |
| *A61B 5/0205* | (2006.01) |

(52) U.S. Cl.
CPC ............ *A61B 5/6804* (2013.01); *A41D 1/002* (2013.01); *A61B 5/0002* (2013.01); *A61B 5/02055* (2013.01); *A61B 5/04085* (2013.01); *A61B 5/1135* (2013.01); *G01L 1/22* (2013.01); *A61B 5/0022* (2013.01); *A61B 2562/12* (2013.01); *H04R 2201/023* (2013.01)

(58) Field of Classification Search
CPC ................ A61B 5/6804; A61B 5/6805; H04R 2201/023; A41D 1/002
See application file for complete search history.

(56) References Cited

U.S. PATENT DOCUMENTS

| | | |
|---|---|---|
| 3,591,526 A | 7/1971 | Junshi |
| 3,793,716 A | 2/1974 | Smith-Johannsen |
| (Continued) | | |

FOREIGN PATENT DOCUMENTS

| | | |
|---|---|---|
| EP | 1057923 A1 | 12/2000 |
| EP | 1335831 A1 | 8/2003 |
| (Continued) | | |

OTHER PUBLICATIONS

Aliverti et al.; U.S. Appl. No. 15/202,833 entitled "Systems and methods to automatically determine garment fit," filed Jul. 6, 2016.
(Continued)

*Primary Examiner* — William Levicky
(74) *Attorney, Agent, or Firm* — Shay Glenn LLP

(57) ABSTRACT

Described herein are apparatuses (e.g., garments, including but not limited to shirts, pants, and the like) for detecting and monitoring physiological parameters, such as respiration, cardiac parameters, and the like.

15 Claims, 45 Drawing Sheets

Related U.S. Application Data

62/058,519, filed on Oct. 1, 2014, provisional application No. 61/950,782, filed on Mar. 10, 2014.

(56) References Cited

U.S. PATENT DOCUMENTS

| | | | |
|---|---|---|---|
| 4,624,817 A | 11/1986 | Gusack et al. | |
| 4,710,981 A | 12/1987 | Sanchez | |
| 4,823,240 A | 4/1989 | Shenker | |
| 4,867,166 A | 9/1989 | Axelgaard et al. | |
| 5,036,865 A | 8/1991 | Keaton | |
| 5,111,818 A | 5/1992 | Suzuki et al. | |
| 5,148,002 A | 9/1992 | Kuo et al. | |
| 5,163,006 A | 11/1992 | Deziel | |
| 5,241,300 A * | 8/1993 | Buschmann | A61B 5/1135 340/531 |
| 5,280,265 A | 1/1994 | Kramer et al. | |
| 5,352,315 A | 10/1994 | Carrier et al. | |
| 5,379,461 A | 1/1995 | Wilmers | |
| 5,395,508 A | 3/1995 | Jolly et al. | |
| 5,557,263 A | 9/1996 | Fisher et al. | |
| 5,581,492 A | 12/1996 | Janik | |
| 5,635,909 A | 6/1997 | Cole | |
| 5,678,448 A | 10/1997 | Fullen et al. | |
| 5,694,645 A | 12/1997 | Triplette | |
| 5,749,365 A | 5/1998 | Magill | |
| 5,802,607 A | 9/1998 | Triplette | |
| 5,824,996 A | 10/1998 | Kochman et al. | |
| 5,845,644 A | 12/1998 | Hughes et al. | |
| 5,853,005 A | 12/1998 | Scanlon | |
| 5,865,740 A | 2/1999 | Kelly et al. | |
| 5,903,222 A | 5/1999 | Kawarizadeh et al. | |
| 5,906,004 A | 5/1999 | Lebby et al. | |
| 5,912,653 A | 6/1999 | Fitch | |
| 5,921,674 A | 7/1999 | Koczi | |
| 6,019,877 A | 2/2000 | Dupelle et al. | |
| 6,024,575 A | 2/2000 | Ulrich | |
| 6,047,203 A | 4/2000 | Sackner et al. | |
| 6,080,690 A | 6/2000 | Lebby et al. | |
| 6,097,297 A | 8/2000 | Fard | |
| 6,136,127 A | 10/2000 | De Bastiani | |
| 6,144,120 A | 11/2000 | Doi et al. | |
| 6,210,771 B1 | 4/2001 | Post et al. | |
| 6,232,879 B1 | 5/2001 | Tyren | |
| 6,259,399 B1 | 7/2001 | Krasner | |
| 6,319,015 B1 | 11/2001 | Faunce | |
| 6,325,066 B1 | 12/2001 | Hughes et al. | |
| 6,341,504 B1 | 1/2002 | Istook | |
| 6,349,201 B1 | 2/2002 | Ford | |
| 6,415,176 B1 | 7/2002 | Scheirer et al. | |
| 6,436,064 B1 | 8/2002 | Kloecker | |
| 6,490,534 B1 | 12/2002 | Pfister | |
| 6,561,814 B2 | 5/2003 | Tilbury et al. | |
| 6,563,424 B1 | 5/2003 | Kaario | |
| 6,642,467 B2 | 11/2003 | Farringdon | |
| 6,668,380 B2 | 12/2003 | Marmaropolous et al. | |
| 6,701,296 B1 * | 3/2004 | Kramer | A61B 5/6806 370/545 |
| 6,713,733 B2 | 3/2004 | Kochman et al. | |
| 6,729,025 B2 | 5/2004 | Farrell et al. | |
| 6,792,124 B2 | 9/2004 | Tilbury et al. | |
| 6,801,140 B2 | 10/2004 | Mantyjarvi et al. | |
| 6,830,344 B2 | 12/2004 | Reho et al. | |
| 6,895,261 B1 | 5/2005 | Palamides | |
| 6,930,608 B2 | 8/2005 | Grajales et al. | |
| 6,968,075 B1 | 11/2005 | Chang | |
| 6,970,731 B1 | 11/2005 | Jayaraman et al. | |
| 6,982,115 B2 | 1/2006 | Poulos et al. | |
| 7,020,508 B2 | 3/2006 | Stivoric et al. | |
| 7,034,685 B2 | 4/2006 | Fabre et al. | |
| 7,161,084 B2 | 1/2007 | Sandbach | |
| 7,173,437 B2 | 2/2007 | Hervieux et al. | |
| 7,191,803 B2 * | 3/2007 | Orr | A61B 5/0002 139/408 |
| 7,210,939 B2 | 5/2007 | Marmaropolous et al. | |
| 7,211,053 B2 | 5/2007 | Marmaropolous et al. | |
| 7,230,610 B2 | 6/2007 | Jung et al. | |
| 7,248,756 B2 | 7/2007 | Ebbesen et al. | |
| 7,250,547 B1 | 7/2007 | Hofmeister et al. | |
| 7,299,034 B2 | 11/2007 | Kates | |
| 7,299,964 B2 | 11/2007 | Jayaraman et al. | |
| 7,319,895 B2 | 1/2008 | Klefstad-Sillonville et al. | |
| 7,320,947 B2 | 1/2008 | Child et al. | |
| 7,321,785 B2 | 1/2008 | Harris | |
| 7,324,841 B2 | 1/2008 | Reho et al. | |
| 7,344,379 B2 | 3/2008 | Marmaropolous et al. | |
| 7,348,645 B2 | 3/2008 | Xu | |
| 7,365,031 B2 | 4/2008 | Swallow et al. | |
| 7,377,133 B2 | 5/2008 | Sandbach et al. | |
| 7,388,166 B2 | 6/2008 | Marmaropolous et al. | |
| 7,429,959 B2 | 9/2008 | Gerder et al. | |
| 7,448,874 B2 | 11/2008 | Willis | |
| 7,476,104 B2 | 1/2009 | Marmaropolous et al. | |
| 7,559,768 B2 | 7/2009 | Marmaropolous et al. | |
| 7,578,195 B2 | 8/2009 | DeAngelis et al. | |
| 7,616,112 B2 | 11/2009 | Miller, III | |
| 7,645,220 B2 | 1/2010 | Hoffman et al. | |
| 7,665,288 B2 | 2/2010 | Karayianni et al. | |
| 7,683,643 B2 | 3/2010 | Qi et al. | |
| 7,712,373 B2 | 5/2010 | Nagle et al. | |
| 7,715,873 B1 | 5/2010 | Biere et al. | |
| 7,719,007 B2 | 5/2010 | Thompkins et al. | |
| 7,732,002 B2 | 6/2010 | Kodas et al. | |
| 7,753,685 B2 | 7/2010 | Lee et al. | |
| 7,753,845 B2 | 7/2010 | Gopinathan et al. | |
| 7,760,082 B2 | 7/2010 | Wong et al. | |
| 7,769,412 B1 | 8/2010 | Gailloux | |
| 7,770,473 B2 | 8/2010 | Von Lilienfeld-Toal et al. | |
| 7,779,656 B2 | 8/2010 | Dias et al. | |
| 7,783,334 B2 | 8/2010 | Nam et al. | |
| 7,787,726 B2 | 8/2010 | Ten Eyck et al. | |
| 7,849,888 B2 | 12/2010 | Karayianni et al. | |
| 7,862,624 B2 | 1/2011 | Tran | |
| 7,870,761 B2 | 1/2011 | Valentine et al. | |
| 7,872,557 B2 | 1/2011 | Seibert | |
| 7,878,030 B2 | 2/2011 | Burr | |
| 7,880,607 B2 | 2/2011 | Olson et al. | |
| 7,891,020 B2 | 2/2011 | Von Bluecher | |
| 7,914,108 B2 | 3/2011 | Konno et al. | |
| 7,933,554 B2 | 4/2011 | Hoyt et al. | |
| 7,955,696 B2 | 6/2011 | Baikerikar et al. | |
| 7,976,480 B2 | 7/2011 | Grajales et al. | |
| 7,982,613 B2 | 7/2011 | Zheng | |
| 7,983,876 B2 | 7/2011 | Vock et al. | |
| 8,008,606 B2 | 8/2011 | Kaiserman et al. | |
| 8,024,023 B2 | 9/2011 | Tolvanen | |
| 8,032,199 B2 | 10/2011 | Linti et al. | |
| 8,063,307 B2 | 11/2011 | Bukshpun et al. | |
| 8,099,258 B2 | 1/2012 | Alten et al. | |
| 8,140,143 B2 | 3/2012 | Picard et al. | |
| 8,146,171 B2 | 4/2012 | Chung et al. | |
| 8,162,857 B2 | 4/2012 | Lanfermann et al. | |
| 8,186,231 B2 | 5/2012 | Graumann et al. | |
| 8,214,008 B2 | 7/2012 | Hassonjee et al. | |
| 8,228,202 B2 | 7/2012 | Buchner et al. | |
| 8,253,586 B1 | 8/2012 | Matak | |
| 8,262,217 B2 | 9/2012 | Furukawa | |
| 8,263,215 B2 | 9/2012 | Burr et al. | |
| 8,267,862 B2 | 9/2012 | Jeong et al. | |
| 8,308,489 B2 | 11/2012 | Lee et al. | |
| 8,331,097 B2 | 12/2012 | Yang et al. | |
| 8,340,740 B2 | 12/2012 | Holzer et al. | |
| 8,348,841 B2 | 1/2013 | Varadan | |
| 8,348,865 B2 | 1/2013 | Jeong et al. | |
| 8,362,882 B2 | 1/2013 | Heubel et al. | |
| 8,373,079 B2 | 2/2013 | Walkington | |
| 8,398,546 B2 | 3/2013 | Pacione et al. | |
| 8,403,845 B2 | 3/2013 | Stivoric et al. | |
| 8,416,579 B2 | 4/2013 | Biesheuvel et al. | |
| 8,475,371 B2 | 7/2013 | Derchak et al. | |
| 8,739,397 B2 | 6/2014 | Nagata et al. | |
| 8,862,431 B2 | 10/2014 | Hodge | |
| 8,925,393 B2 | 1/2015 | Cannard et al. | |
| 8,945,328 B2 | 2/2015 | Longinotti-Buitoni et al. | |

(56) References Cited

U.S. PATENT DOCUMENTS

| | | |
|---|---|---|
| 8,948,839 B1 | 2/2015 | Longinotti-Buitoni et al. |
| 8,954,129 B1 | 2/2015 | Schlegel et al. |
| 9,566,032 B2 | 2/2017 | Babaeizadeh et al. |
| 9,979,547 B2 | 5/2018 | Starner et al. |
| 2002/0032386 A1* | 3/2002 | Sackner ............... A61B 5/0205 600/536 |
| 2002/0093515 A1 | 7/2002 | Fay et al. |
| 2003/0139692 A1 | 7/2003 | Barrey et al. |
| 2004/0115430 A1 | 6/2004 | Leonard |
| 2004/0249242 A1* | 12/2004 | Lau ..................... A61F 2/2481 600/37 |
| 2005/0029680 A1 | 2/2005 | Jung et al. |
| 2005/0058744 A1 | 3/2005 | Steinberg et al. |
| 2005/0067816 A1 | 3/2005 | Buckman |
| 2005/0107722 A1 | 5/2005 | Ozaki et al. |
| 2005/0228234 A1 | 10/2005 | Yang |
| 2006/0007059 A1 | 1/2006 | Bell |
| 2006/0062993 A1 | 3/2006 | Ogata et al. |
| 2006/0080182 A1 | 4/2006 | Thompson et al. |
| 2006/0124470 A1 | 6/2006 | Zama et al. |
| 2006/0139165 A1 | 6/2006 | Bader |
| 2006/0155182 A1 | 7/2006 | Mazzarolo |
| 2007/0000912 A1 | 1/2007 | Aisenbrey |
| 2007/0046720 A1 | 3/2007 | Konno et al. |
| 2007/0049842 A1 | 3/2007 | Hill et al. |
| 2007/0151312 A1 | 7/2007 | Bruce et al. |
| 2007/0153363 A1 | 7/2007 | Gruner |
| 2007/0177770 A1 | 8/2007 | Derchak et al. |
| 2007/0178716 A1 | 8/2007 | Glaser et al. |
| 2007/0202765 A1 | 8/2007 | Krans et al. |
| 2007/0293781 A1* | 12/2007 | Sims ..................... A61B 5/1135 600/534 |
| 2008/0045815 A1 | 2/2008 | Derchak et al. |
| 2008/0058744 A1 | 3/2008 | Tippey et al. |
| 2008/0064964 A1 | 3/2008 | Nagata et al. |
| 2008/0083720 A1 | 4/2008 | Gentile et al. |
| 2008/0083721 A1 | 4/2008 | Kaiserman et al. |
| 2008/0083740 A1 | 4/2008 | Kaiserman et al. |
| 2008/0171914 A1 | 7/2008 | Ouwerkerk et al. |
| 2008/0177168 A1* | 7/2008 | Callahan ............ A61B 5/04085 600/382 |
| 2008/0234561 A1 | 9/2008 | Roesicke et al. |
| 2008/0241391 A1 | 10/2008 | Kim et al. |
| 2008/0246629 A1 | 10/2008 | Tsui et al. |
| 2008/0255794 A1 | 10/2008 | Levine |
| 2008/0258921 A1 | 10/2008 | Woo et al. |
| 2008/0269629 A1* | 10/2008 | Reiner ................. A61B 5/4836 600/544 |
| 2008/0269652 A1 | 10/2008 | Reiner |
| 2008/0287769 A1 | 11/2008 | Kurzweil et al. |
| 2008/0287770 A1 | 11/2008 | Kurzweil et al. |
| 2008/0294019 A1 | 11/2008 | Tran |
| 2009/0012408 A1 | 1/2009 | Nagata et al. |
| 2009/0018410 A1 | 1/2009 | Coene et al. |
| 2009/0105795 A1 | 4/2009 | Minogue et al. |
| 2009/0112078 A1 | 4/2009 | Tabe |
| 2009/0157327 A1 | 6/2009 | Nissila |
| 2009/0227856 A1 | 9/2009 | Russell et al. |
| 2009/0281394 A1 | 11/2009 | Russell et al. |
| 2009/0286055 A1 | 11/2009 | Pourdeyhimi et al. |
| 2010/0004720 A1 | 1/2010 | Li et al. |
| 2010/0029598 A1 | 2/2010 | Kopitz et al. |
| 2010/0041974 A1* | 2/2010 | Ting ..................... A61B 5/0408 600/388 |
| 2010/0059274 A1 | 3/2010 | Ives et al. |
| 2010/0071205 A1 | 3/2010 | Graumann et al. |
| 2010/0077528 A1 | 4/2010 | Lind et al. |
| 2010/0112195 A1 | 5/2010 | Kodas et al. |
| 2010/0113910 A1 | 5/2010 | Brauers et al. |
| 2010/0149567 A1 | 6/2010 | Kanazawa et al. |
| 2010/0185062 A1 | 7/2010 | Salazar et al. |
| 2010/0185398 A1 | 7/2010 | Berns et al. |
| 2010/0194815 A1 | 8/2010 | Furukawa |
| 2010/0198038 A1* | 8/2010 | Nagata ............... A61B 5/04085 600/372 |
| 2010/0234715 A1 | 9/2010 | Shin et al. |
| 2010/0274100 A1 | 10/2010 | Behar et al. |
| 2010/0292598 A1 | 11/2010 | Roschk et al. |
| 2010/0309209 A1 | 12/2010 | Hodgins et al. |
| 2010/0312071 A1 | 12/2010 | Schenk |
| 2010/0324405 A1 | 12/2010 | Niemi et al. |
| 2011/0000412 A1 | 1/2011 | Chung et al. |
| 2011/0015498 A1 | 1/2011 | Mestrovic et al. |
| 2011/0032103 A1 | 2/2011 | Bhat et al. |
| 2011/0042125 A1 | 2/2011 | Lee et al. |
| 2011/0087115 A1 | 4/2011 | Sackner et al. |
| 2011/0092795 A1 | 4/2011 | Derchak |
| 2011/0100683 A1 | 5/2011 | Bhattacharya et al. |
| 2011/0102304 A1 | 5/2011 | Nelson |
| 2011/0115624 A1 | 5/2011 | Tran |
| 2011/0125064 A1 | 5/2011 | Shyr |
| 2011/0130643 A1 | 6/2011 | Derchak et al. |
| 2011/0144457 A1 | 6/2011 | Coulon |
| 2011/0183068 A1 | 7/2011 | Yamakawa et al. |
| 2011/0184270 A1 | 7/2011 | Russell et al. |
| 2011/0259638 A1 | 10/2011 | Sherrill et al. |
| 2011/0267578 A1 | 11/2011 | Wilson |
| 2011/0277206 A1 | 11/2011 | Sokolowski |
| 2011/0288605 A1 | 11/2011 | Kaib et al. |
| 2012/0024833 A1 | 2/2012 | Klewer et al. |
| 2012/0029299 A1 | 2/2012 | Deremer et al. |
| 2012/0030935 A1 | 2/2012 | Slade et al. |
| 2012/0031431 A1 | 2/2012 | Carlson et al. |
| 2012/0035426 A1 | 2/2012 | Mielcarz et al. |
| 2012/0071039 A1 | 3/2012 | Debock et al. |
| 2012/0071793 A1 | 3/2012 | Gal |
| 2012/0078127 A1 | 3/2012 | McDonald et al. |
| 2012/0088986 A1 | 4/2012 | David et al. |
| 2012/0118427 A1 | 5/2012 | Brookstein et al. |
| 2012/0127687 A1 | 5/2012 | Allee et al. |
| 2012/0136231 A1 | 5/2012 | Markel |
| 2012/0143093 A1 | 6/2012 | Stirling et al. |
| 2012/0144551 A1 | 6/2012 | Guldalian |
| 2012/0144561 A1 | 6/2012 | Begriche et al. |
| 2012/0144934 A1 | 6/2012 | Russell et al. |
| 2012/0146797 A1 | 6/2012 | Oskin et al. |
| 2012/0158074 A1 | 6/2012 | Hall |
| 2012/0165645 A1 | 6/2012 | Russell et al. |
| 2012/0165717 A1 | 6/2012 | Al Khaburi |
| 2012/0184826 A1 | 7/2012 | Keenan et al. |
| 2012/0188158 A1 | 7/2012 | Tan et al. |
| 2012/0197224 A1 | 8/2012 | Chagger |
| 2012/0215076 A1 | 8/2012 | Yang et al. |
| 2012/0223833 A1 | 9/2012 | Thomas et al. |
| 2012/0233751 A1 | 9/2012 | Hexels |
| 2012/0238845 A1 | 9/2012 | Yang |
| 2012/0246795 A1 | 10/2012 | Scheffler et al. |
| 2012/0255166 A1 | 10/2012 | Kim et al. |
| 2012/0324616 A1 | 12/2012 | Hyde et al. |
| 2012/0330109 A1 | 12/2012 | Tran |
| 2013/0013331 A1 | 1/2013 | Horseman |
| 2013/0019372 A1 | 1/2013 | Esses |
| 2013/0019383 A1 | 1/2013 | Korkala et al. |
| 2013/0041272 A1 | 2/2013 | Guillen et al. |
| 2013/0053674 A1 | 2/2013 | Volker |
| 2013/0066168 A1 | 3/2013 | Yang et al. |
| 2013/0072777 A1 | 3/2013 | Tremblay |
| 2013/0077263 A1 | 3/2013 | Oleson et al. |
| 2013/0079860 A1 | 3/2013 | Besio |
| 2013/0144111 A1 | 6/2013 | Wang et al. |
| 2013/0179288 A1 | 7/2013 | Moses et al. |
| 2013/0211208 A1 | 8/2013 | Varadan |
| 2013/0212900 A1 | 8/2013 | Stewart |
| 2013/0231711 A1 | 9/2013 | Kalb |
| 2013/0244121 A1 | 9/2013 | Gogotsi et al. |
| 2013/0245423 A1 | 9/2013 | Derchak et al. |
| 2013/0281795 A1 | 10/2013 | Varadan |
| 2013/0314668 A1 | 11/2013 | Haddadi et al. |
| 2014/0061273 A1 | 3/2014 | Bullivant et al. |
| 2014/0070957 A1 | 3/2014 | Longinotti-Buitoni et al. |
| 2014/0100436 A1 | 4/2014 | Brunner et al. |
| 2014/0135593 A1 | 5/2014 | Jayalth et al. |

(56) References Cited

U.S. PATENT DOCUMENTS

| | | |
|---|---|---|
| 2014/0182880 A1 | 7/2014 | Simenhaus et al. |
| 2014/0206948 A1 | 7/2014 | Romem |
| 2014/0303470 A1 | 10/2014 | Tsukada et al. |
| 2014/0312027 A1 | 10/2014 | Augustine et al. |
| 2015/0143601 A1 | 5/2015 | Longinotti-Buitoni et al. |
| 2015/0289820 A1 | 10/2015 | Miller et al. |

FOREIGN PATENT DOCUMENTS

| | | |
|---|---|---|
| EP | 1478249 A1 | 11/2004 |
| EP | 1509128 A1 | 3/2005 |
| EP | 1622512 A2 | 2/2006 |
| EP | 1709903 A1 | 10/2006 |
| EP | 1905112 A2 | 4/2008 |
| EP | 1907075 A2 | 4/2008 |
| EP | 1925718 A2 | 5/2008 |
| EP | 2025369 A2 | 2/2009 |
| EP | 2191737 A1 | 6/2010 |
| EP | 2196142 A1 | 6/2010 |
| EP | 2217145 A1 | 8/2010 |
| EP | 2314744 A2 | 4/2011 |
| EP | 3037036 A1 | 6/2016 |
| WO | WO 90/06189 A1 | 6/1990 |
| WO | WO 00/16493 A1 | 3/2000 |
| WO | WO 01/01855 A1 | 1/2001 |
| WO | WO03/000015 A2 | 1/2003 |
| WO | WO 03/060449 A1 | 7/2003 |
| WO | WO 2004/076731 A1 | 9/2004 |
| WO | WO 2004/107831 A2 | 12/2004 |
| WO | WO 2005/032447 A2 | 4/2005 |
| WO | WO2005/067796 A1 | 7/2005 |
| WO | WO 2005/096133 A1 | 10/2005 |
| WO | WO 2006/064447 A2 | 6/2006 |
| WO | WO 2006/102538 A2 | 9/2006 |
| WO | WO 2007/056557 A1 | 5/2007 |
| WO | WO 2008/137046 A1 | 11/2008 |
| WO | WO 2008/153786 A1 | 12/2008 |
| WO | WO 2009/040696 A1 | 4/2009 |
| WO | WO 2009/112281 A1 | 9/2009 |
| WO | WO 2010/038176 A1 | 4/2010 |
| WO | WO 2010/044018 A1 | 4/2010 |
| WO | WO 2010/058346 A2 | 5/2010 |
| WO | WO 2010/085671 A1 | 7/2010 |
| WO | WO 2010/085688 A1 | 7/2010 |
| WO | WO2010/096907 A1 | 9/2010 |
| WO | WO 2010/120945 A1 | 10/2010 |
| WO | WO 2011/092620 A1 | 8/2011 |
| WO | WO 2011/156095 A2 | 12/2011 |
| WO | WO2012/011068 A1 | 1/2012 |
| WO | WO 2012/060524 A1 | 5/2012 |
| WO | WO 2012/066056 A1 | 5/2012 |
| WO | WO 2012/073076 A1 | 6/2012 |
| WO | WO 2012/073230 A1 | 6/2012 |
| WO | WO 2012/083066 A2 | 6/2012 |
| WO | WO 2012/104484 A1 | 8/2012 |
| WO | WO 2012/110954 A1 | 8/2012 |
| WO | WO 2012/112186 A1 | 8/2012 |
| WO | WO 2012/113014 A1 | 8/2012 |
| WO | WO 2012/140079 A1 | 10/2012 |
| WO | WO 2012/140522 A2 | 10/2012 |
| WO | WO 2012/168836 A2 | 12/2012 |
| WO | WO 2012/176193 A1 | 12/2012 |
| WO | WO 2014/025430 A2 | 2/2014 |
| WO | WO2014/075682 A1 | 5/2014 |
| WO | WO2014/204323 A1 | 12/2014 |
| WO | WO2015/103620 A1 | 7/2015 |
| WO | WO 2015/138515 A1 | 9/2015 |
| WO | WO2016/035350 A1 | 3/2016 |

OTHER PUBLICATIONS

Aliverti et al.; Compartmental analysis of breathing in the supine and prone positions by optoelectronic plethysmography; Ann Biomed Eng; 29(1):60-70; Jan. 2001.

Babchenko et al.; Fiber optic sensor for the measurement of respiratory chest circumference changes; J Biomed Opt; 4(2):224-229; Apr. 1999.

Cala et al.; Chest wall and lung volume estimation by optical reflectance motion analysis; J Appl Physiol; 81(6):2680-2689; Dec. 1996.

Chadha et al.; Validation of respiratory inductive plethysmography using different calibration procedures; Am Rev Respir Dis; 125:644-649; Jun. 1982.

Chen et al.; Color structured light system of chest wall motion measurement for respiratory volume evaluation; J Biomed Opt; 15(2):026013; Mar.-Apr. 2010.

D'Angelo et al.; A system for respiratory motion detection using optical fibers embedded into textiles; Conf Proc IEEE Med Biol Soc; 3694-3697; Aug. 2008.

Ferrigno et al.; Three-dimensional optical analysis of chest wall motion; J Appl Physiol; 77(3):1224-1231; Sep. 1994.

Gramse et al.; Novel concept for a noninvasive cardiopulmonary monitor for infants: a pair of pajamas with an integrated sensor module; Ann Biomed Eng; 31(2):152-158; Feb. 2003.

Heilman et al.; Accuracy of the LifeShirt (Vivometrics) in the detection of cardiac rhythms; Biol Psychol; 75(3):300-305; Jul. 2007.

Kenyon et al.; Rib cage mechanics during quiet breathing and exercise in humans; J Appl Physiol; 83(4):1242-1255; Oct. 1997.

Konno et al.; Measurement of the separate volume changes of rib cage and abdomen during breathing; J Appl Physiol; 22(3):407-422; Mar. 1967.

LaFortuna et al.; A new instrument for the measurement of rib cage and abdomen circumference variation in respiration at rest and during exercise; Eur J Appl Physiol Occup Physiol; 71(2-3):259-265; Mar. 1995.

Milledge et al.; Inductive plethysmography—a new respiratory transducer; J Physiol; 267(1):4P-5P; May 1977.

Peacock et al.; Optical mapping of the thoracoabdominal wall; Thorax; 39 (2):93-100; Feb. 1984.

Peacock et al.; Optical measurement of the change in trunk volume with breathing; Bull Eur Physiopathol Respir; 21(2):125-129; Mar.-Apr. 1985.

Pennock B.E.; Rib cage and abdominal piezoelectric film belts to measure ventilatory airflow; J Clin Monit; 6(4):276-283; Oct. 1990.

Sackner et al.; Calibration of respiratory inductive plethysmograph during natural breathing; J Appl Physiol; 66(1)410-420; Jan. 1989.

Saumarez; Automated optical measurements of human torso surface movements during freathing; J. Appl. Physiol.; 60(2); pp. 702-709; Feb. 1986.

Zimmerman et al.; Postural changes in rib cage and abdominal volume—motion coefficients and their effect on the calibration of a respiratory inductance plethysmograph; Am Rev Respir Dis; 127(2):209-214; Feb. 1983.

Dodgson; Variation and extrema of human interpupillary distance; Prod. of SPIE: Stereoscopic Displays and Virtual Reality Systems XI; vol. 5291; pp. 36-46; Jan. 2004.

Mauri et al.; U.S. Appl. No. 15/335,403 entitled "Calibration packaging apparatuses for physiological monitoring garments," filed Oct. 26, 2016.

Longinotti-Buitoni et al; U.S. Appl. No. 15/324,152 entitled "Garments having stretchable and conductive ink," filed Jan. 5, 2017.

\* cited by examiner

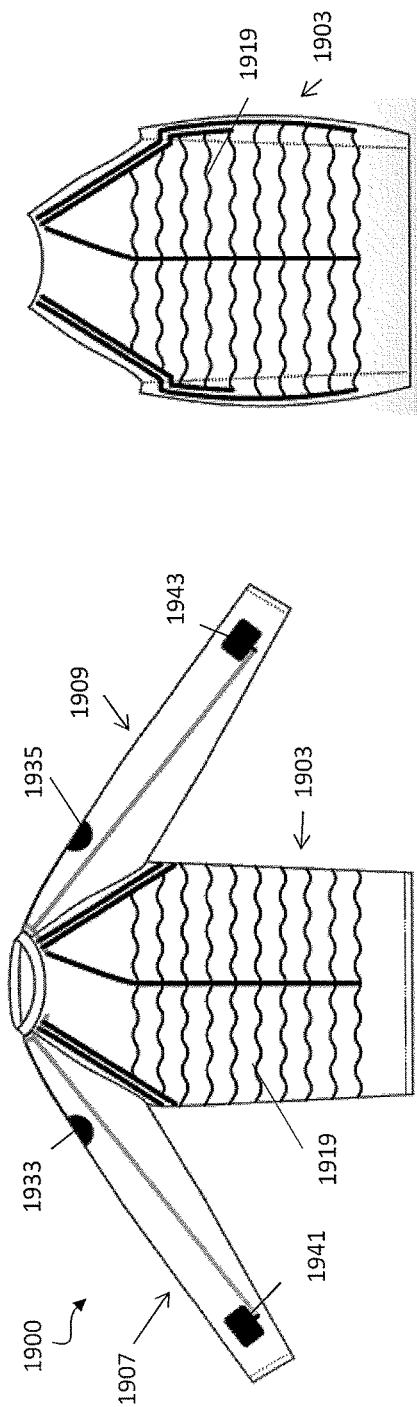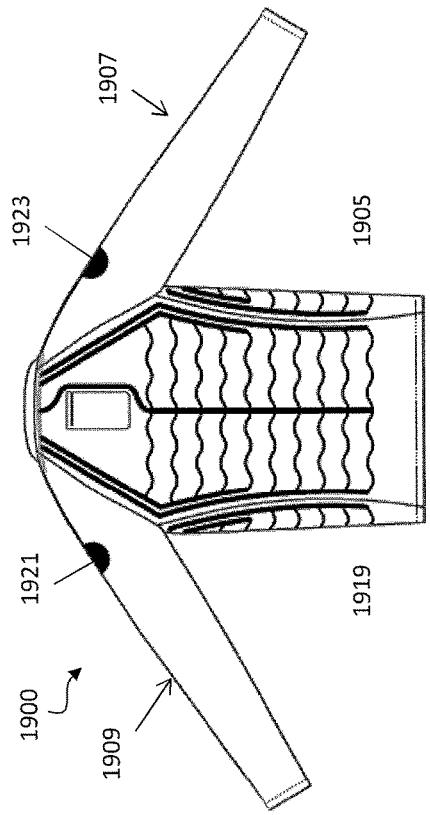

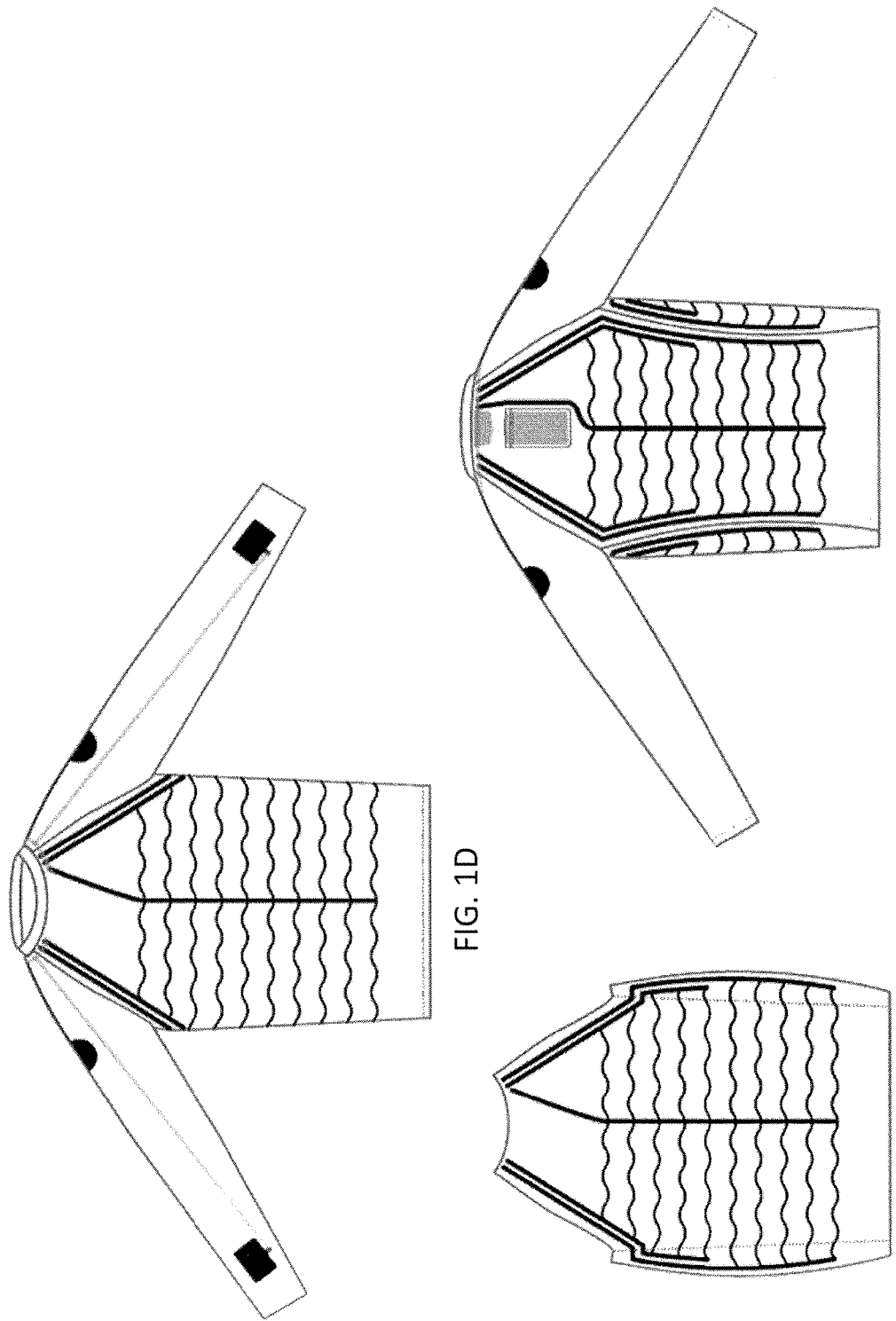

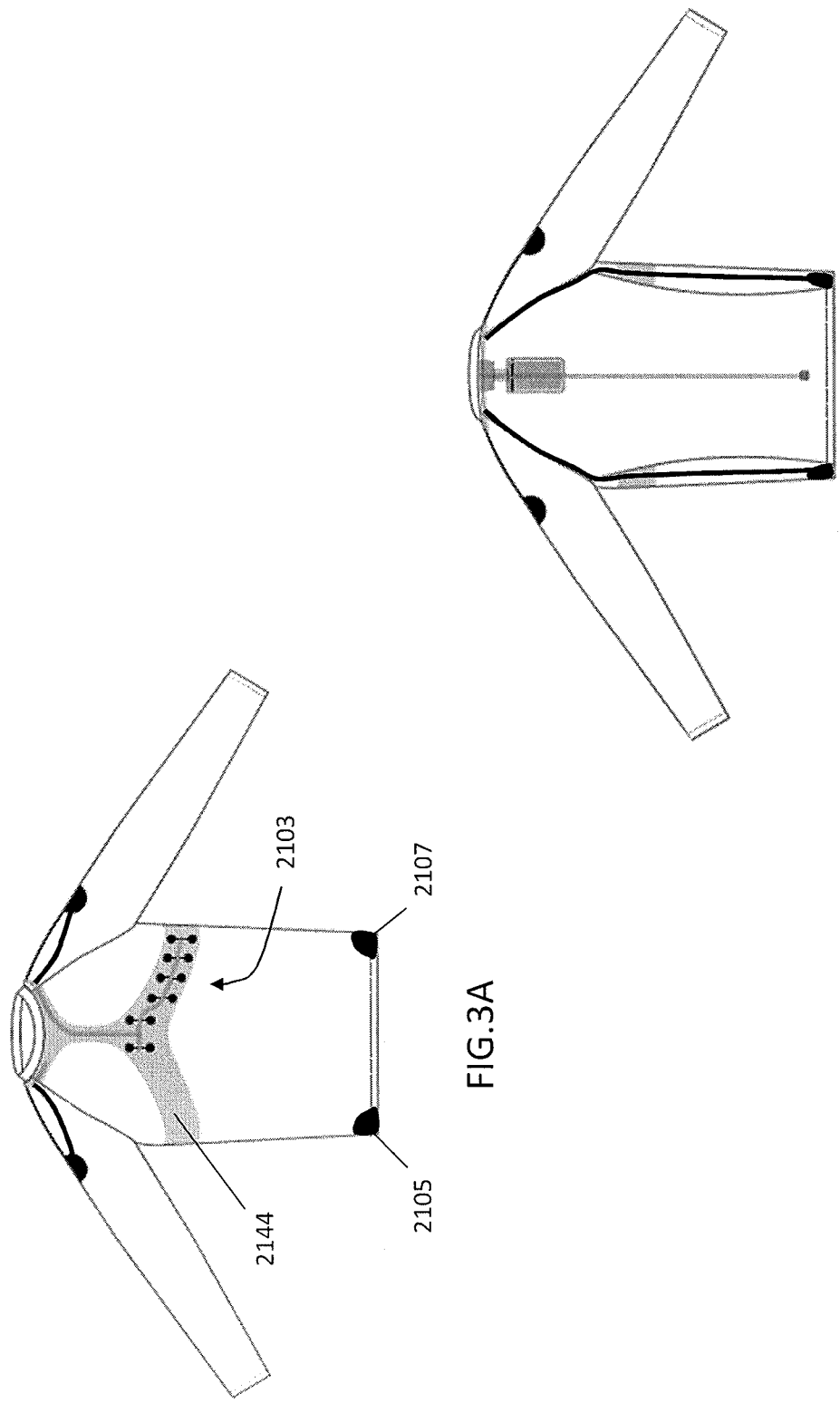

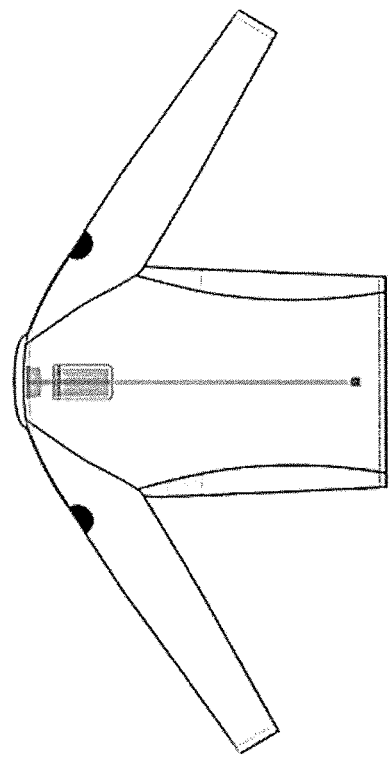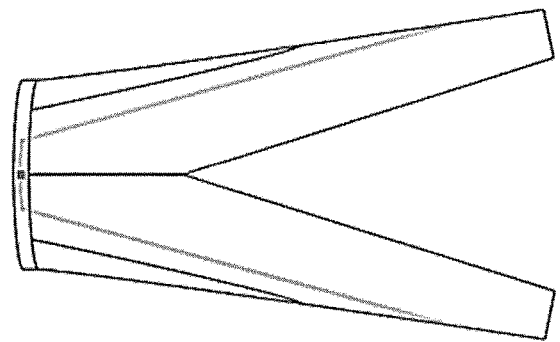
FIG. 4B
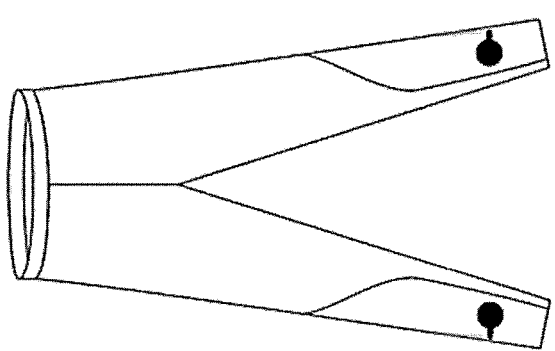
FIG. 4A

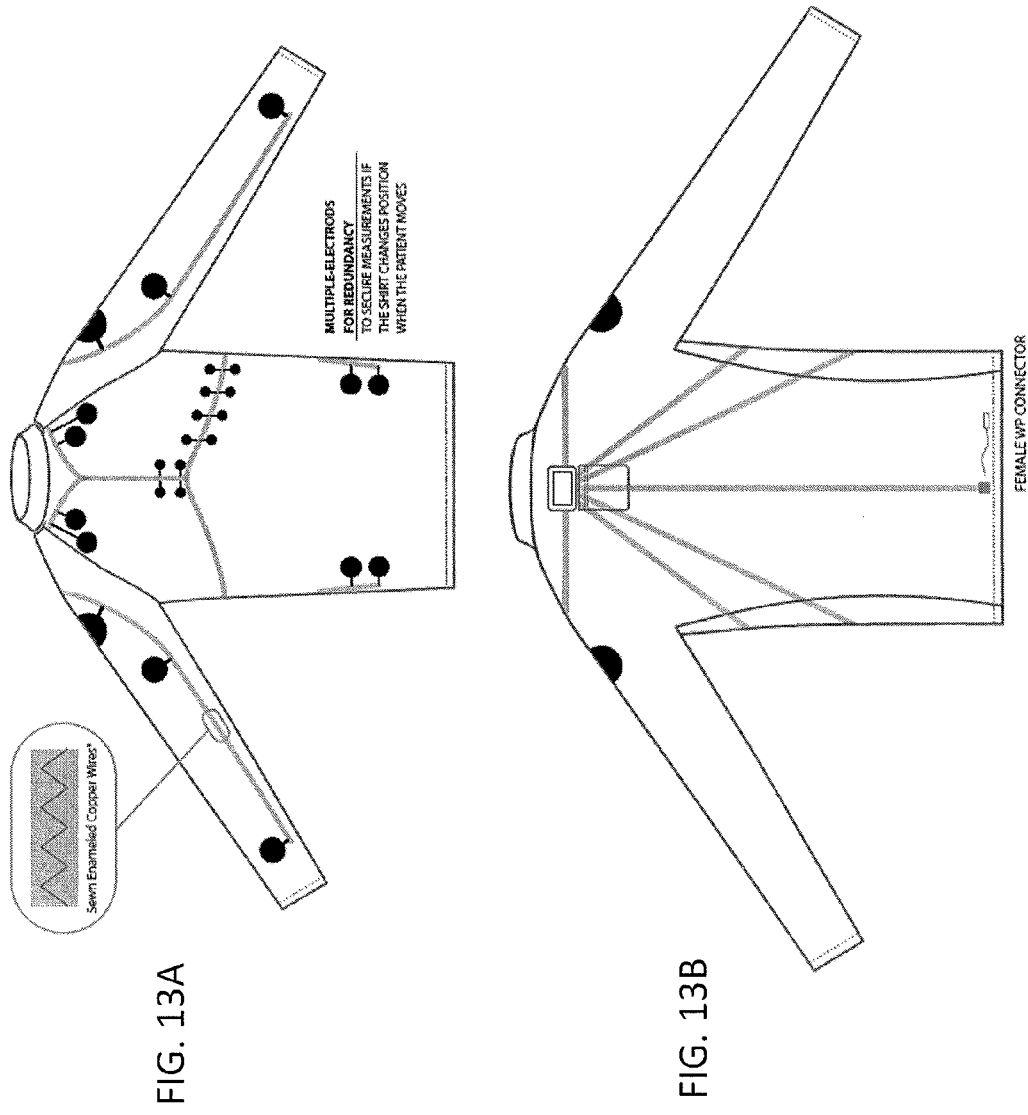

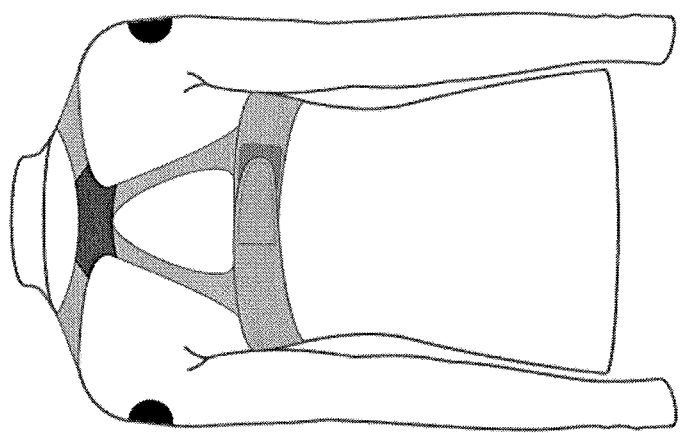
FIG. 14B
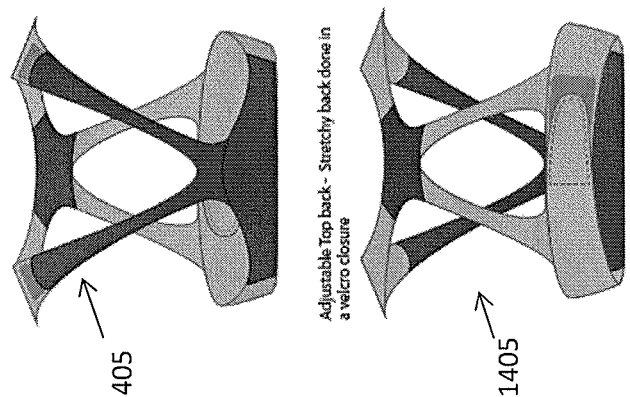
FIG. 14C
Adjustable Top Front - Velcro strips to get the ideal fit
FIG. 14D
Adjustable Top back - Stretchy back done in a velcro closure
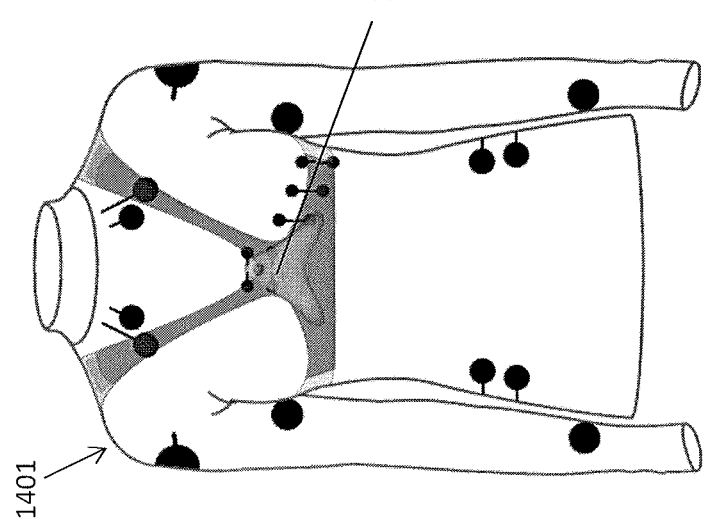
FIG. 14A FIG. 15A
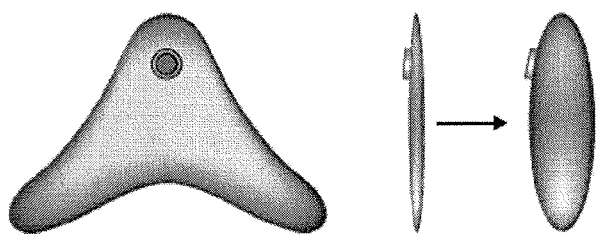
FIG. 15B
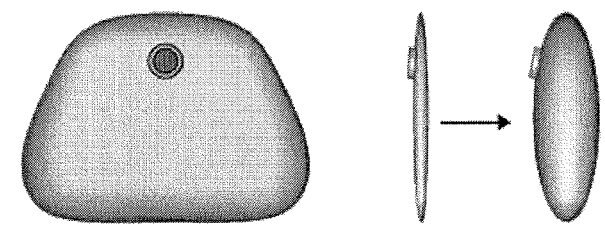
FIG. 15C
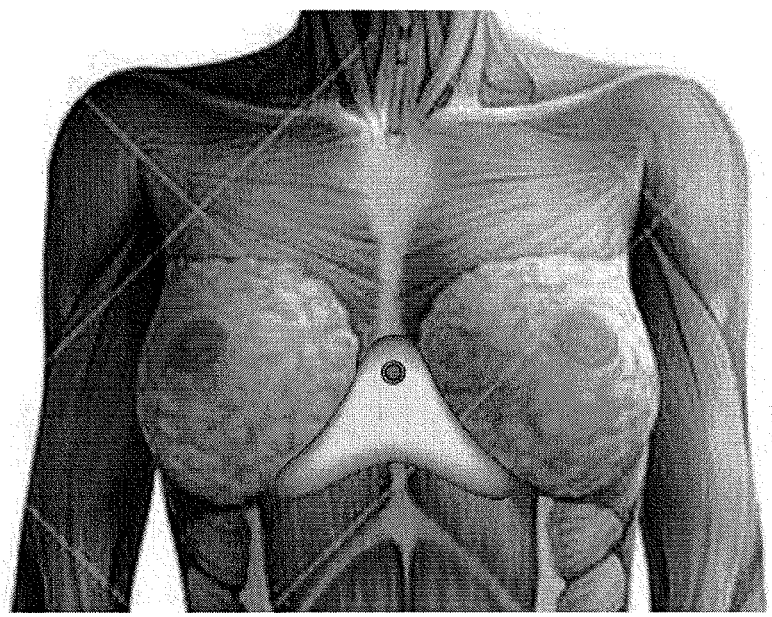
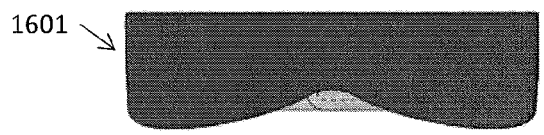
FIG. 16A
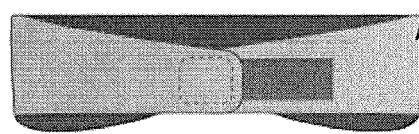
FIG. 16B

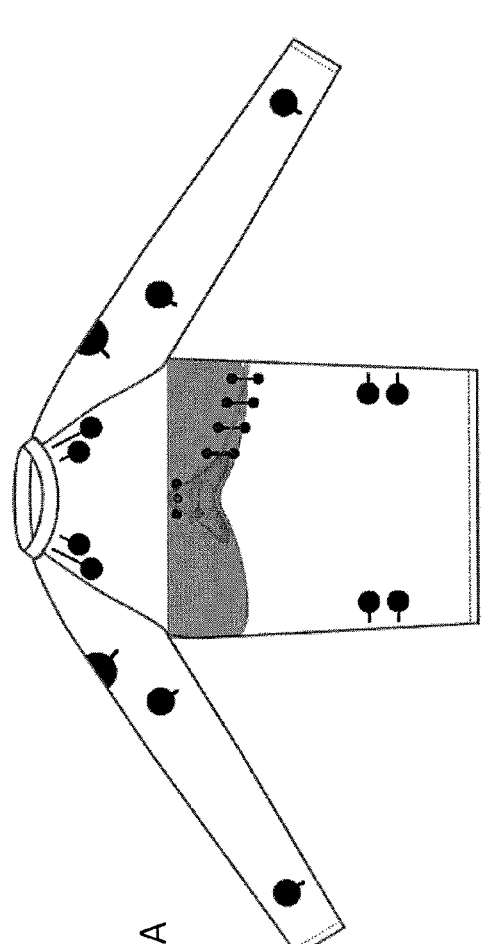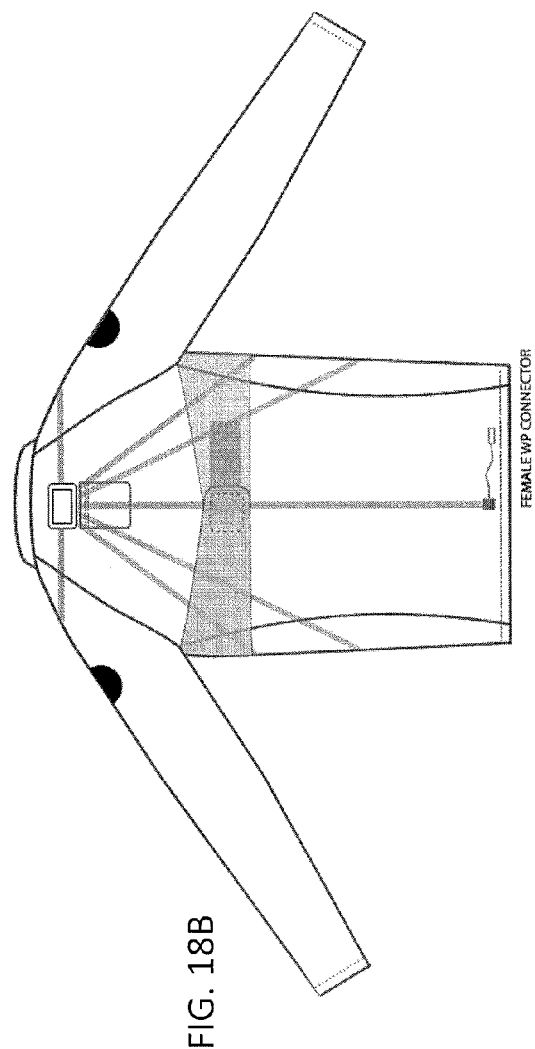
FIG. 18A
FIG. 18B

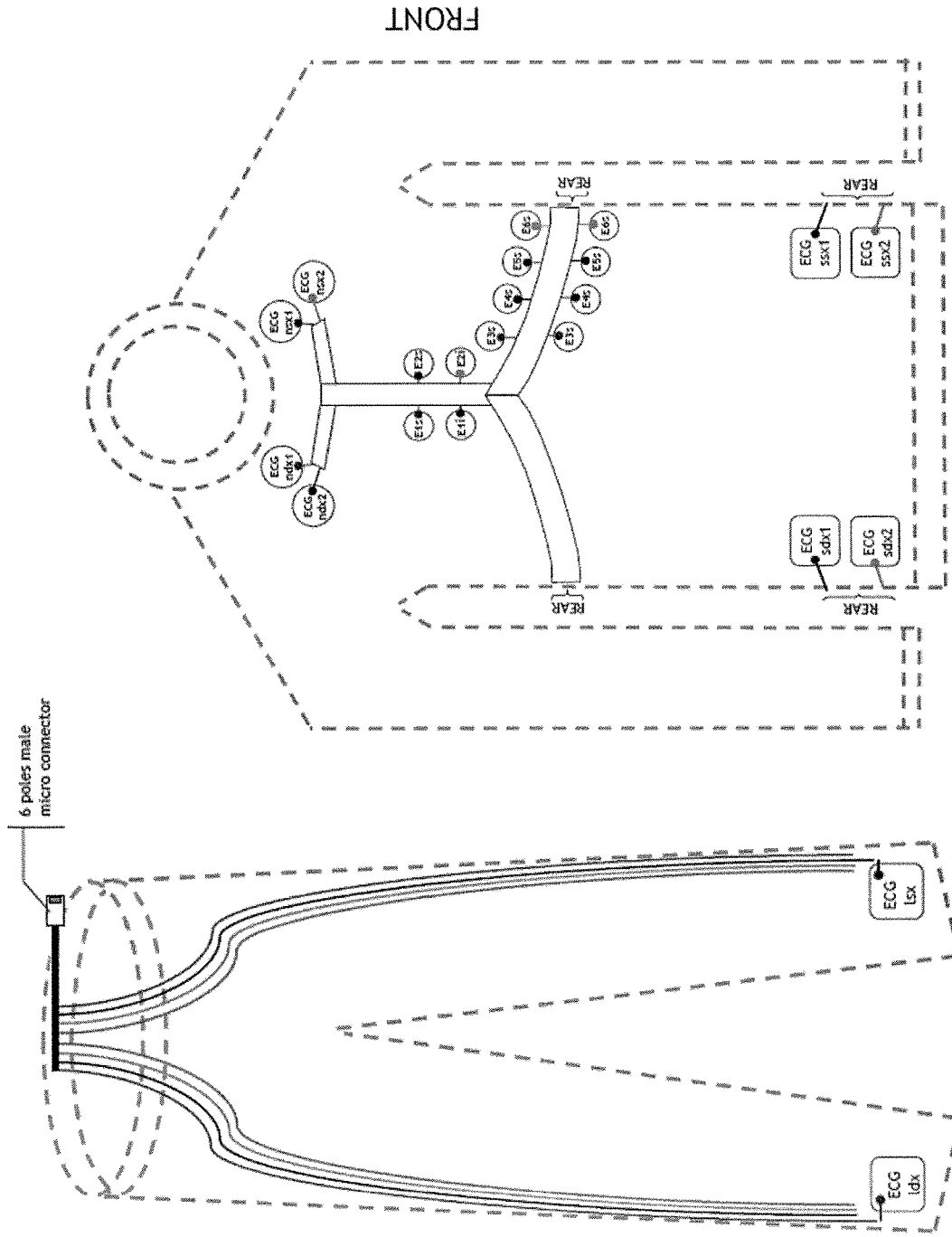

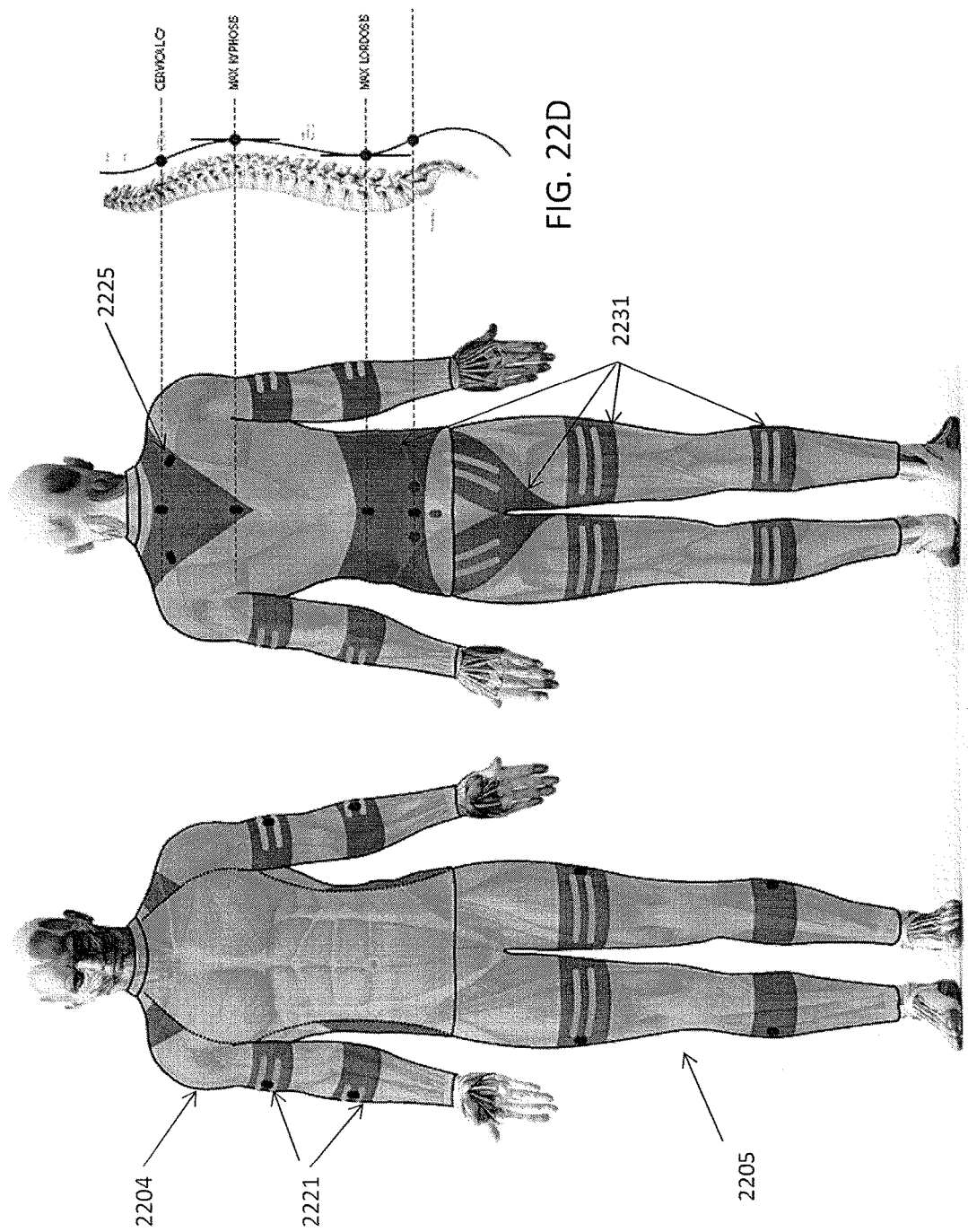

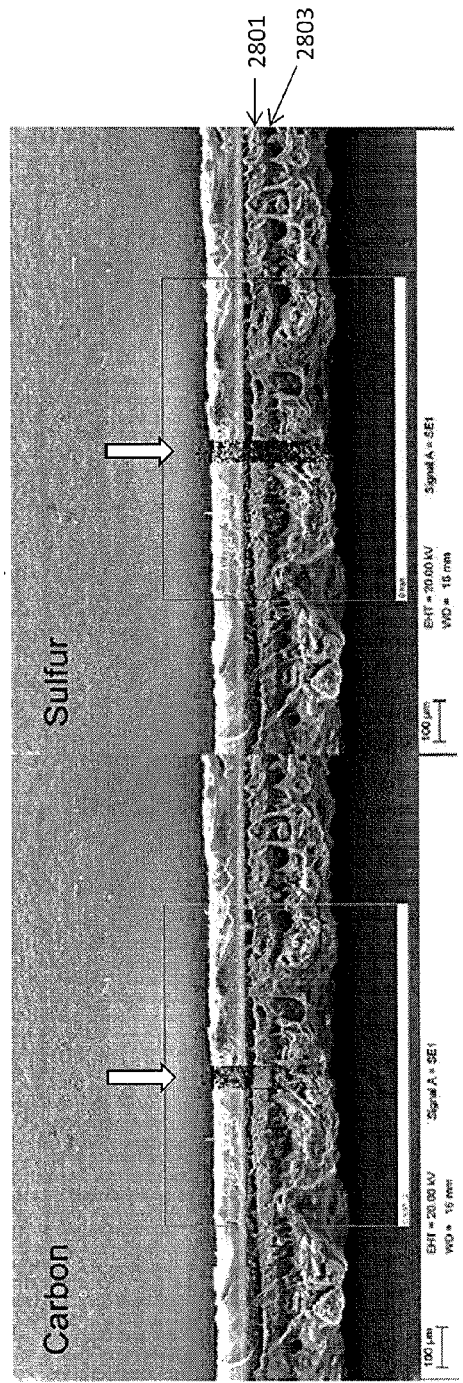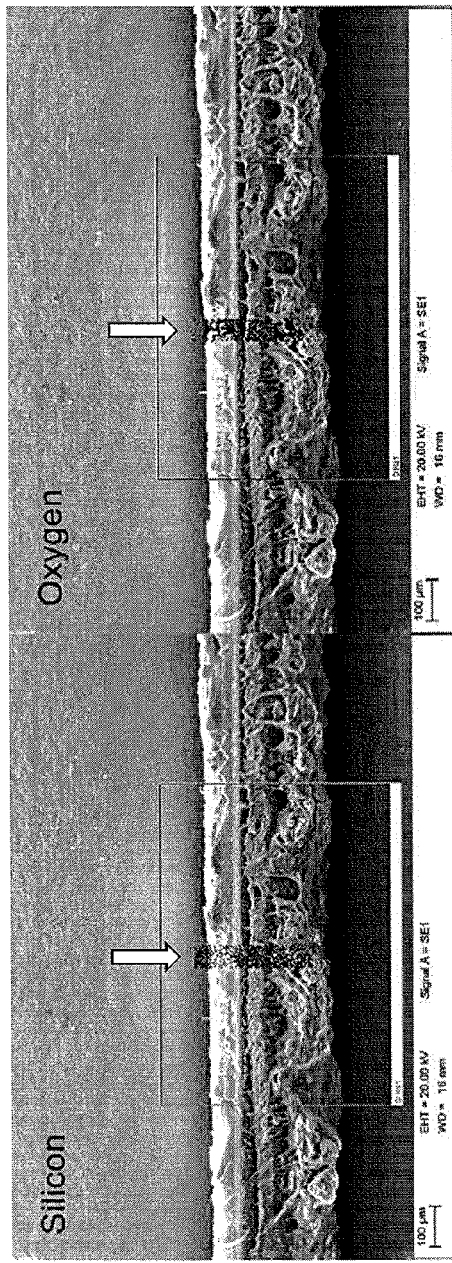
FIG. 40A
FIG. 40B
FIG. 40C
FIG. 40D

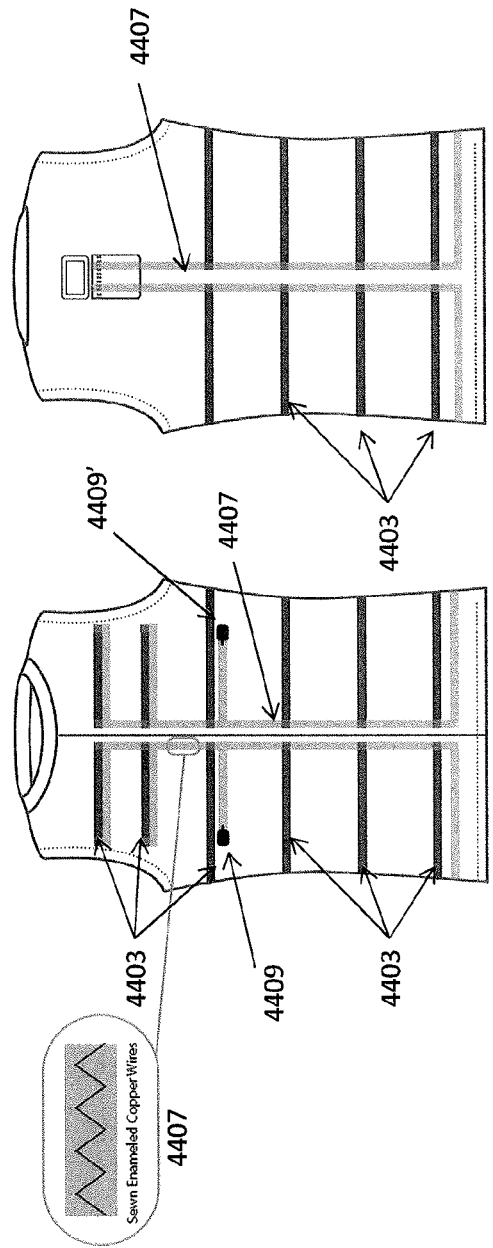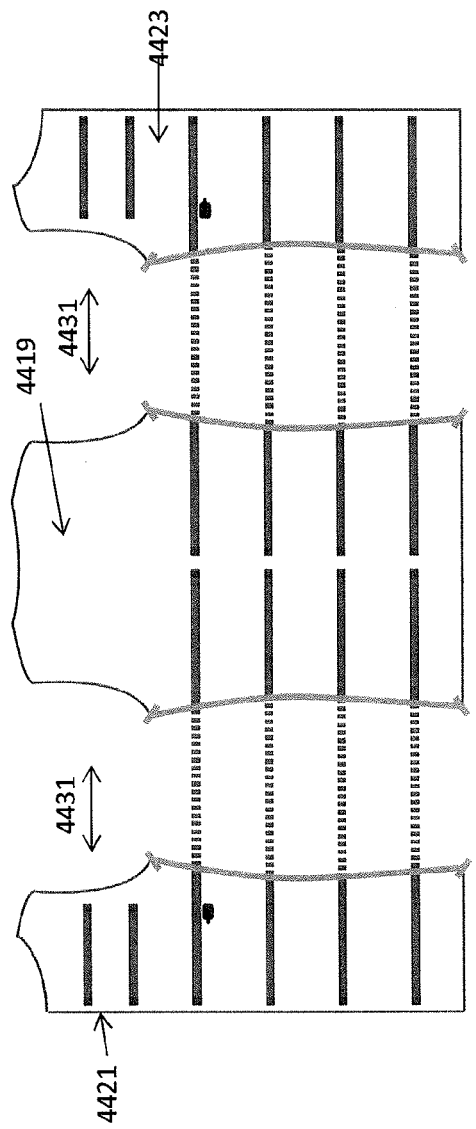

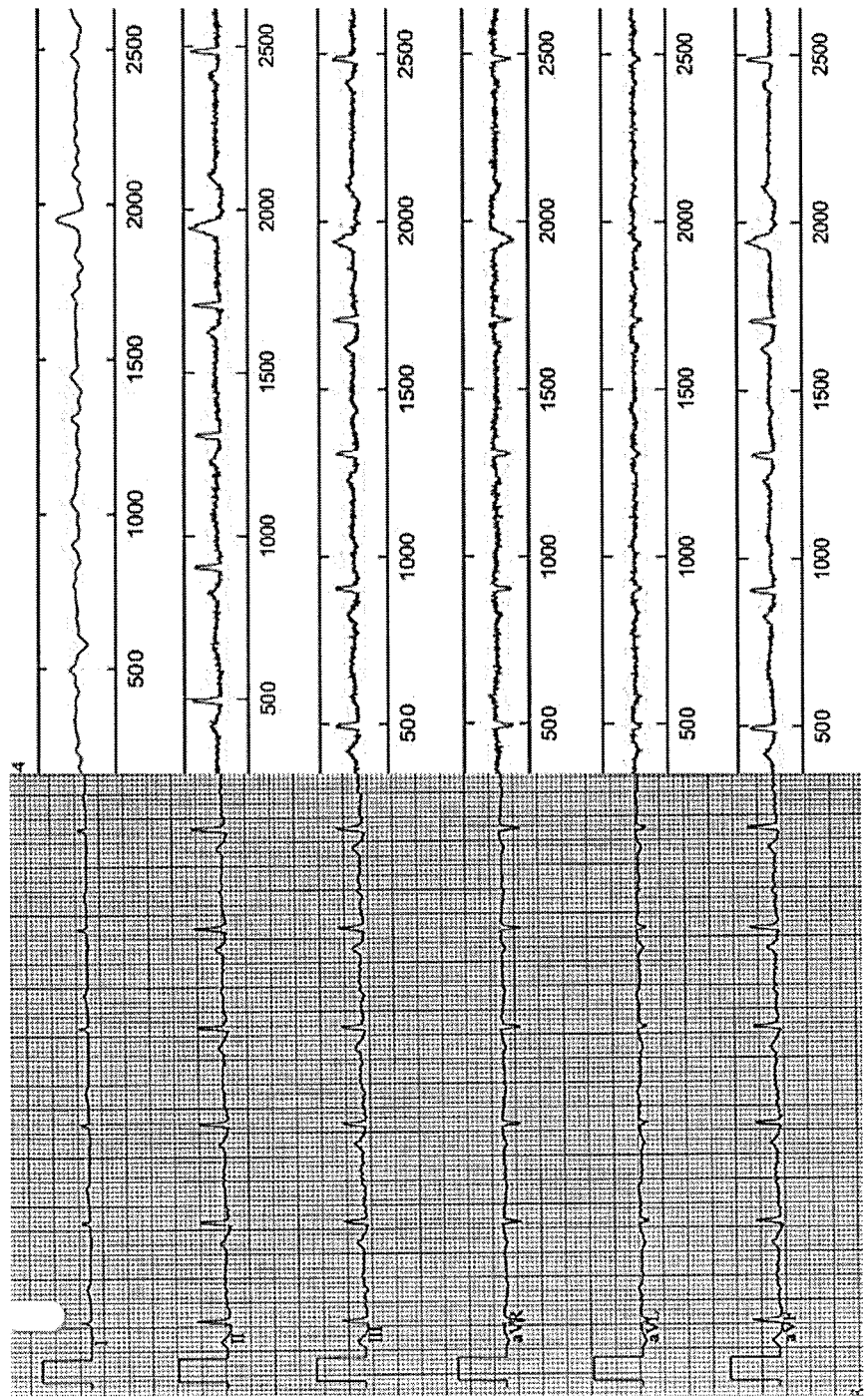

| Workload [W] | RR Reference System* [bpm] | RR Band System* [bpm] |
|---|---|---|
| 1 | 18 | 18.53 |
| 50 | 14 | 14.30 |
| 100 | 12 | 11.08 |
| 150 | 25 | 22.86 |
| 200 | 30 | 29.67 |

FIG. 47B

*Frequency values are calculated as an average on 20 seconds when a minute since the load increase has passed

PHYSIOLOGICAL MONITORING GARMENTS

CROSS REFERENCE TO RELATED APPLICATIONS

This application claims priority to U.S. Provisional Patent Application No. 61/950,782, filed Mar. 10, 2014, titled "PHYSIOLOGICAL MONITORING GARMENTS;" U.S. Provisional Patent Application No. 62/058,519, filed Oct. 1, 2014, titled "DEVICES AND METHODS OF RUSE WITH PHYSIOLOGICAL MONITORING GARMENTS;" U.S. Provisional Patent Application No. 62/080,966, filed Nov. 17, 2014, titled "PHYSIOLOGICAL MONITORING GARMENTS;" and U.S. Provisional Patent Application No. 62/097,560, filed Dec. 29, 2014, titled "STRETCHABLE, CONDUCTIVE TRACES AND METHODS OF MAKING AND USING SAME," each of which is herein incorporated by reference in its entirety.

This patent application also claims priority as a continuation-in-part to U.S. patent application Ser. No. 14/612,060, filed Feb. 2, 2015, titled "GARMENTS HAVING STRETCHABLE AND CONDUCTIVE INK", which is a continuation of U.S. patent application Ser. No. 14/331,185, filed Jul. 14, 2014, and titled "METHODS OF MAKING GARMENTS HAVING STRETCHABLE AND CONDUCTIVE INK," now U.S. Pat. No. 8,945,328 each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are wearable apparatuses (e.g., "garments") that can communicate with a user and others, receive both direct (user-selected) input and indirect (user monitoring) input, for example, detecting to signals from the user (e.g. from a wearable electronics based garment) and store or transmit this information. In particular, described herein are wearable monitoring and input systems that can monitor physiological parameters from the wearer.

BACKGROUND

In the last twenty years, the development of mobile telecommunications devices have has dramatically expanded and modified the ways in which people communicate. Computers with ever-faster computer processors enabled faster communication with increased processing speed and improved analysis of vast quantities of data. In addition, sensor technology has also rapidly expanded how patients have been monitored, even by non-professionals. The development of various sensors enabled a variety of measurements to be taken and analyzed by a computer to generate useful information. In recent years, the use of medical sensing technology in combination with various communications platforms has provided new and interesting ways for people, including patients, to be monitored or to monitor themselves and communicate the results of the monitoring with their physician or caregiver. For example, mobile devices such as smart phones have enabled mobile device users to communicate remotely and provided some ability to obtain, analyze, use, and control information and data. For example, a mobile device user may be able to use application software (an "app") for various individualized tasks, such as recording their medical history in a defined format, playing a game, reading a book, etc. An app may work with a sensor in a mobile device to provide information that a user wants. For example, an app may work with an accelerometer in a smart phone and determine how far someone walked and how many calories were burned during the walk.

The use of a mobile communications platform such as a smartphone with one or more such biometric sensors have been described in various contexts. For example, US2010/0029598 to Roschk et al. describes a "Device for Monitoring Physical Fitness" that is equipped with a heart rate monitor component for detecting heart rate data and an evaluation device for providing fitness information that can be displayed by a display device and is derived by a processing unit, embodied for reading in and including supplementary personal data. US2009/0157327 to Nissila describes an "Electronic Device, Arrangement, and Method of Estimating Fluid Loss" that is equipped with "an electronic device comprising: a processing unit configured to receive skin temperature data generated by a measuring unit, to receive performance data from a measuring unit, and to determine a theoretical fluid loss value on the basis of the received performance data."

Similarly, clothing that includes sensors have been previously suggested. See, e.g., US2007/0178716 to Glaser et al., which describes a "modular microelectronic-system" designed for use with wearable electronics. US2012/0071039 to Debock et al. describes interconnect and termination methodology fore-textiles that include a "conductive layer that includes conductors includes a terminal and a base separately provided from the terminal. The terminal has a mating end and a mounting end." US2005/0029680 to Jung et al. describes a method and apparatus for the integration of electronics in textiles.

For example, cardiovascular and other health-related problems, including respiratory problems may be detected by monitoring a patient. Monitoring may allow early and effective intervention, and medical assistance may be obtained based on monitored physiological characteristics before a particular health issue becomes fatal. Unfortunately, most currently available cardiovascular and other types of health monitoring systems are cumbersome and inconvenient (e.g., impractical for everyday use) and in particular, are difficult or impractical to use for long-term monitoring, particularly in an unobtrusive manner.

It has been proposed that patient health parameters, including vital signs (such as ECG, respiration, blood oxygenation, heart rate, etc.) could be actively monitoring using one or more wearable monitors, however, to date such monitors have proven difficult to use and relatively inaccurate. Ideally such monitors could be unobtrusively worn by the subject (e.g., as part of a garment, jewelry, or the like). Although such garments have been proposed, see, e.g., US 2012/0136231, these garments suffer from a number of deficits, including being uncomfortable, difficult to use, and providing inaccurate results. For example, in applications such as US 2012/0136231, a number of individual electrodes are positioned on the garment and connected to a processor by woven conductive fibers or the like; although such garments "require . . . consistent and firm conductive contact with the subject's skin," in order to provide accurate readings, such designs require that the garment be restrictive in order to prevent movement of the garment (and thus sensors) contacting these skin regions. Such a configuration rapidly becomes uncomfortable, particularly in a garment that would ideally be worn for many hours or even days. In addition, even such tightly worn garments often move relative to the wearer (e.g., slip or ride up). Further, devices/ garments such as those described in the prior art are difficult and expensive to manufacture, and are often rather "fragile", preventing robust usage and washing. Finally, such devices/ garments typically do not allow processing of manual user input directly on the garment, but either relay entirely on passive monitoring, or require an interface of some sort (including off-garment interfaces).

The use of garments including one or more sensors that may sense biometric data have not found widespread use. In part, this may be because such garments may be limited in the kinds and versatility of the inputs that they accept, as well as limits in the comfort, and form factor of the garment. For example, sensors, and the leads providing power to and receiving signals from the sensors have not been fully integrated with the garment in a way that allows the garment to be flexible, attractive, practical, and above all, comfortable. For example, most such proposed garments have not been sufficiently stretchable. Finally, such proposed garments are also limited in the kind of data that they can receive, and how they process the received information.

Thus, existing garments (e.g., devices and wearable sensing apparatuses) and processes for analyzing and communicating the physical and emotional status of an individual may be inaccurate, inadequate, limited in scope, unpleasant, and/or cumbersome.

What is needed are apparatuses (including garments) having one more sensors that may be comfortably worn, yet provide relatively accurate and movement-insensitive measurements over a sustained period of time. It would also be beneficial to provide garments that can be easily and inexpensively manufactured. Finally it may be beneficial to provide garments having a direct user interface that is on the garment, and particularly interfaces which are formed as part of the garment (including the fabric).

In particular, what is needed is a stretchable and conductive patterns (e.g., traces) that can be attached or applied onto a garment. These stretchable, conductive patterns may be used even with the most stretchable of fabrics (such as compression fabrics/compression garments) and moved through numerous stretch/relaxation cycles with the underlying fabric without breaking and while maintaining a stable set of electrical properties such as conductance over time and use. The apparatuses, including wearable devices (e.g., garments) and systems including them described herein may address some or all of the problems identified above.

SUMMARY OF THE DISCLOSURE

Described herein are physiological parameter monitoring garments having sensors formed of printed conductive ink on a compression garment that are arranged and configured for robust sensing and comfortable wear. In particular, the garments (e.g., shirts, pants, undergarments) described herein are configured to allow robust sensing of one or more physiological parameter using a conductive ink sensor printed directly onto the garment and connected by a conductive trace (which may or may not be reinforced on the garment) to an interface region of the garment which may connect to an analysis unit such as a microprocessor that is configured to measure, store, process and/or transmit the recorded parameter(s).

For example, described herein are shirts adapted to continuously monitor the regional respiration of a wearer. A shirt for monitoring respiration may include: a shirt body comprising a fabric, wherein the body is configured as a compression garment that expands and contracts to hold the shirt against the wearer's torso; a plurality of respiratory sensors arranged on different regions of the body, wherein each respiratory sensor comprises: a plurality of generally parallel conductive ink traces and/or conductive elastic printed and/or attached on an outer portion of the body; and a regional conductive connector, wherein each of the generally parallel conductive ink traces connect to the regional conductive connector; and an interface (e.g., module interface) located on the body, wherein the regional conductive connector for each respiratory sensor connects to the interface, further wherein the interface is configured to connect with a processor (e.g., sensor manager unit) to detect electrical resistance from each of the conductive connectors. Described herein are two types of respiration sensors. The first one is formed of a conductive ink trace that may be printed on the fabric forming the garment or transferred and/or attached to the garment. Any of the conductive ink materials described herein may be used (including in particular, those formed of a layer of adhesive and one or more layers of conductive ink with an intermediate/gradient region there between. The second type of respiration sensor is formed of a conductive elastic material, which is also described in greater detail below. Although there may be particular benefits to using one type of respiratory sensor compared to the other (e.g., lower electrical hysteresis), and except as made clear by the specific context, either respiratory sensor may be used interchangeably with the other.

In general, the respiratory sensors may be regional. Different regions (e.g., quadrants) of the shirt body may be covered by different sensors, permitting detection and monitoring of "regional" respiration. As the shirt (which is fit snugly to the body) expands and contracts with a wearer's respiratory effort, region respiration (movement) is detected by a variation in the resistance of the conductive ink traces and/or conductive elastic material in each of the different regions. The plurality of generally parallel conductive ink traces comprise between three and 50 parallel traces. Sensing by the respiratory sensors may be particularly robust by arranging multiple (e.g., 2, 3, 4, 5, 6, 7, 8, 9, 10, 11, 12, 13, 14, 15, 16, 17, 18, 19, 20, 25, 30, 35, etc.) conductive ink traces in an approximately parallel fashion across the region of the shirt body; each of these parallel traces is connected (in parallel) to the region conductive connector (and on the other end to a reference, e.g., reference line), effectively determining the overall resistance from the parallel resistance, e.g., $R_{total}$=(product of all resistance for each trace)/ (sum of each resistance for each trace).

In some variations the shirt is configured to detect the respiration off four regions (e.g., anterior/posterior and pectoral/abdominal regions; or pectoral/abdominal and left/ right regions, etc.). In some variations the respiratory sensors comprise eight respiratory sensors, sensing eight regions (anterior/posterior, pectoral/abdominal and left/right regions). In general, the plurality of respiratory sensors may be separately arranged in anterior or posterior, upper or lower, right or left regions of the body. More than eight regions may be determined as well (e.g., dividing the body into further subdivisions); the regions do not need to be the same size.

The plurality of generally parallel conductive ink traces are each stretchable traces; stretching of the conductive ink typically changes the resistance (detecting stretch, and thereby respiration). The plurality of generally parallel conductive ink traces may be printed on the outer portion of the body in any pattern. For example, the traces may be printed as parallel straight lines, zig-zag lines, curved lines, e.g., for example, the traces may be printed in an undulating pattern. In general, the plurality of generally parallel conductive ink traces may be configured create varying electrical resistance through the traces as the subject breathes; for example, the lines may extend in a direction that will be transverse to the patient's body (across the chest) when the shirt is worn.

As mentioned, the plurality of respiratory sensors may comprise a reference line to which each of the generally parallel conductive ink traces connect at an opposite end of the generally parallel conductive ink trace from the regional conductive connector. The reference line may be a "ground". The reference line typically also connects to the interface (and ultimately the processor that is detecting the change in resistance of the lines due to respiration).

Each respiratory sensor may be configured to average the variable electrical resistance in the plurality of generally parallel conductive ink traces forming the respiratory sensor. Thus a very small current or voltage may be applied across the conductive traces to determine the change in resistance with respiration. The conductive traces may generally be insulated (e.g., prevented from contacting the wearer's skin directly and/or shorting due to sweat, etc.).

Any of the shirts described herein may also include a user input, such as a touchpoint sensor at a touchpoint location on the body, configured to sense when the wearer touches the shirt at the touchpoint location. The touchpoint sensor may be used as an input and/or control for the device. For example, the user may "mark" a time when something occurs, such as a shortness of breath, or other respiratory episode, or to indicate when activity is increasing (e.g., exercising, etc.) or decreasing, or to start/stop/pause, etc. the recording and/or analysis of respiration, or to save, transmit, process, etc. detected regional respiration. Multiple touchpoint sensors may be used.

The shirt may also include one or more additional sensors, such as a heart rate sensor. For example, the shirt may include a conductive ink electrode on an inner surface of the body configured to contact the wearer's skin, and an electrode conductive connector extending from the conductive ink electrode to the module interface. The electrode may be used to detect heart rate, or the like. Multiple electrodes may be used (e.g., an electrode pair). For example, the conductive ink electrode may be located on a sleeve of the shirt (or sleeves).

The shirt may also include a holder (e.g., pocket) on the body configured to hold a sensor manager unit in connection with the module interface.

Other sensors that may be used include any other activity/motion sensor (e.g., an accelerometer). The other sensors may be on the shirt and/or connected to the shirt of directly to or part of the processor receiving the signals from the sensors.

The regional conductive connectors typically comprise a conductive material on a substrate that is attached to the body. The substrate may support the conductive material and may interface with the garment so that the conductive ink is electrically coupled with the conductive material forming the connector. For example, the substrate may be a polymeric material. In some variations (e.g., see Appendix A) the substrate is Kapton.

Also described herein are methods of sensing regional respiration using shirts configured as described above. For example, a method of detecting region respiration may include wearing any of the shirts described herein, and receiving/transmitting/storing/analyzing the variations in resistance through the conductive ink traces arranged in parallel in different (typically non-overlapping) regions on the body of the search.

Also described herein are garments (e.g., shirts and/or pants) that are configured to continuously monitor a wearer's electrocardiogram (ECG). For example, a shirt may include: a body comprising a fabric, wherein the body is configured as a compression garment that expands and contracts to hold the shirt against the wearer's torso; a first set of six electrical sensors arranged on the body in a first curve extending across the left pectoral region of the wearer's chest when the shirt is worn, wherein each electrical sensor comprises a conductive ink electrode printed on an inner surface of the body; a second (redundant) set of six electrical sensors arranged on the body in a second curve that is adjacent to the second curve; a support harness region of the body extending from a neck region and overlying the first and second sets of electrical sensors; a right arm electrode formed from conductive ink printed on an inner surface of the body; and a left arm electrode formed from conductive ink printed on an inner surface of the body; wherein each electrical sensor is connected to an interface on the body by a conductive extending from the electrical sensor to the interface and further wherein the interface is configured to connect with a sensor manager unit to detect electrical activity from each of the electrical sensors, the right arm electrode and the left arm electrode.

In general such shirts may provide multiple electrodes on the chest (pectoral region) that may be connected (e.g., in parallel) to act as individual leads (e.g., V1-V6) for the chest electrodes of a 12-lead ECG. The apparatus may be configured to robustly detect the signal even if there is a shifting or movement of the electrodes as the garment moves on the body of the wearer. Further, the garment may be comfortably held in position, and the position of the electrodes held relatively fixedly, even where the curvature of the wearer's body may otherwise prevent good contact between the wearer and the electrodes, by the additional support region of the body of the garment (e.g., the yoke/harness support).

Also disclosed herein are support garments configured to be worn over the garments, such as the shirts, disclosed herein. The support garment can include a support structure configured to push sensors/electrodes on the shirt into better engagement with the chest of the wearer. The support structure can be inflatable and configured based on the gender and chest anatomy of the wearer. In some cases the support structure is self-inflating.

The present invention also relates to stretchable conductive traces as well as methods of making them. In particular, described herein are conductive elastic ribbon materials that may be used as respiration sensors, and/or as conductive traces. These conductive elastic ribbons may be formed of these stretchable (e.g., elastic) material that is impregnated with a conductive ink, which is allowed to (at least partially or completely) dry, and can be connected, by adhesive, stitching, or the like, to a garment. Unlike other conductive materials, including conductive inks and wires, these conductive elastic ribbons may be mechanically loaded and unloaded repeatedly and exhibit little if any electrical hysteresis.

Specific examples of the kinds of apparatuses (e.g., devices and systems, including garments) that are described herein include physiological parameter monitoring garments having sensors formed of printed conductive ink on a compression garment that are arranged and configured for robust sensing and comfortable wear. In particular, the garments (e.g., shirts, pants, undergarments) described herein are configured to allow robust sensing of one or more physiological parameter using a respiration sensor connected directly, transferred onto or printed directly on the garment and connected by a conductive trace (which may or may not be reinforced on the garment, such as a wire ribbon material) to an interface region of the garment which may connect to an analysis unit such as a microprocessor that is configured to measure, store, process and/or transmit the recorded parameter(s).

For example, described herein are garments adapted to continuously monitor the regional respiration of a wearer. A shirt for monitoring respiration may include: a shirt body comprising a fabric, wherein the body is configured as a compression garment that expands and contracts to hold the shirt against the wearer's torso; a plurality of respiratory sensors arranged on different regions of the body, wherein each respiratory sensor comprises: either a conductive ink trace printed on an outer portion of the body or a conductive elastic strip, wherein the respiratory sensor(s) connect to the regional conductive connector; and an interface (e.g., module interface) located on the body, wherein the regional conductive connector for each respiratory sensor connects to the interface, further wherein the interface is configured to connect with a processor (e.g., sensor manager unit) to detect electrical resistance from each of the conductive connectors.

In general, the respiratory sensors may be regional. Different regions (e.g., quadrants) of the shirt body may be covered by different sensors, permitting detection and monitoring of "regional" respiration. As the garment (which is fit snugly to the body) expands and contracts with a wearer's respiratory effort, region respiration (movement) is detected by a variation in the resistance of the conductive ink traces in each of the different regions.

Any of the garments described herein may also be referred to as wearable electronics devices. As mentioned, these devices (garments) may typically include: a compression fabric and at least one stretchable and conductive ink pattern on the garment. The conductive ink pattern typically includes a layer of conductive ink (which may itself be formed by layering multiple layers of conductive ink to form the final thickness) and a layer of (insulating) adhesive, and an intermediate zone between the two where the conductive ink and the elastic adhesive are partially combined, for example in a gradient region. The intermediate zone may be thinner than, approximately as thick as, or thicker than the conductive ink layer, while the adhesive layer may be thicker.

For example, a conductive ink pattern may include: a layer of conductive ink having: between about 40-60% conductive particles, between about 30-50% binder; between about 3-7% solvent; and between about 3-7% thickener; a layer of an elastic adhesive on the garment; and a gradient region between the conductive ink and the adhesive, the gradient region comprising a nonhomogeneous mixture of the conductive ink and the adhesive wherein the concentration of conductive ink decreases from a region closer to the layer of conductive ink to the layer of elastic adhesive.

In general, the compression garments described herein may be configured to exert a pressure of between about 3 mm Hg and about 70 mmHg on a subject's body surface to allow a stable and continuous positioning of the garment onto the subject's body.

The composition of the conductive ink portion may typically include conductive particles in a binder, thickener and solvent, as mentioned. The conductive particles may comprise particles of carbon black, or of one or more of: carbon black, graphene, graphite, silver metal powder, copper metal powder, or iron metal powder, mica coated with an oxide (e.g., mica coated with antimony-doped tin dioxide), etc. The binder typically comprises formaldehyde-free binder, for example, acrylic binder. The solvent may be, for example, propylenyc glycol. An example of a thickener is polyurethanic thickener.

In general, any appropriate adhesive (e.g., elastic adhesive) may be used. For example, an elastic adhesive may include a thermo-adhesive water-based glue that is electrically insulative. In any of these variations, an insulating resin may be positioned at least partially over the layer of conductive ink.

The conductive ink pattern may include a plurality of layers of the conductive ink.

The thickness of the layer of the elastic adhesive may be greater than the thickness of the gradient region and the thickness of the gradient region may be approximately the same or greater than the thickness of the conductive ink. For example, the ratio of elastic adhesive to intermediate (gradient) region to conductive ink may be approximately 1.1 to 5 (adhesive): 0.8 to 1.2 (intermediate region): 0.5 to 1.2 (conductive ink). In one example, the thickness of the ink portion of the conductive ink pattern is between about 30-70 μm, the thickness of the transition zone (the gradient/intermediate region) is between about 30-90 μm, and the thickness of the adhesive (glue) region is between about 100 to 200 μm.

In general, the resistivity of the conductive trace may be less than about 10 Kohms/square. For example, the bulk resistivity may be between about 0.2 to about 20 ohms*cm, and the sheet resistivity may be between about 100 to 10,000 ohms/square (ohms per square). In one example the bulk resistivity was measured as 11.5 ohms*cm and sheet resistivity at 1913 ohms/square. The resistivity of the conductive pattern may vary with applied stretch.

In general, the resulting conductive ink patterns are extremely stretchable, while maintaining their electrical properties and without breaking. For example, the conductive ink pattern may be configured to stretch up to 500% of a resting length without breaking.

Any of the conductive ink patterns described herein may be formed as all or part of a sensor, a trace, and/or as an electrode. The conductive ink pattern may be connected to another (e.g., more rigid) conductive material. For example a conductive ink pattern may be connected to a sensor module or interface for a sensor module using a conductive ink pattern formed as a trace or by connecting to a conductive thread or wire that is also attached to the garment. For example, a device (garment) as described herein may include a conductive thread coupled to the garment and connected at one end to the conductive ink pattern.

A wearable electronics devices may include: a garment comprising a compression fabric; and at least one stretchable and conductive ink pattern on the garment having a sheet resistivity of less than about 10 Kohms/square, wherein the conductive ink pattern is stretchable up to at least about 200% without breaking, and comprises: a layer of conductive ink having: between about 40-60% conductive particles, between about 30-50% binder; between about 3-7% solvent; and between about 3-7% thickener; a layer of an elastic adhesive on the garment; a gradient region between the conductive ink and the adhesive, the gradient region comprising a nonhomogeneous mixture of the conductive ink and the adhesive wherein the concentration of conductive ink decreases from a region closer to the layer of conductive ink to the layer of elastic adhesive; and an insulating resin over at least a portion of the layer of conductive ink.

A wearable electronics device may include: a garment comprising a compression fabric; at least one stretchable and conductive ink pattern on the garment, wherein the conductive ink pattern comprises: a layer of conductive ink having: between about 40-60% conductive particles, between about 30-50% binder; between about 3-7% solvent; and between about 3-7% thickener; a layer of an elastic adhesive on the garment; and a gradient region between the conductive ink and the adhesive, the gradient region comprising a nonhomogeneous mixture of the conductive ink and the adhesive wherein the concentration of conductive ink decreases from a region closer to the layer of conductive ink to the layer of elastic adhesive; and a conductive thread coupled to the compression fabric and electrically connected at one end region to the conductive ink, wherein the conductive thread extends along garment in a sinusoidal or zig-zag pattern. The conductive thread may be stitched onto the compression fabric, and/or glued onto the compression fabric.

As mentioned above, methods of forming any of the apparatuses (e.g., devices and systems, such as garments) described herein may include forming the stretchable conductive ink pattern either directly onto a fabric, or indirectly by forming a transfer and then transferring it. For example, a method of making a wearable electronics garment may include: placing a transfer substrate comprising a stretchable conductive ink pattern against a compression fabric, wherein the conductive ink pattern comprises: a layer of conductive ink having: between about 40-60% conductive particles; a layer of an elastic adhesive; and a gradient region between the conductive ink and the adhesive, the gradient region comprising a nonhomogeneous mixture of the conductive ink and the adhesive wherein the concentration of conductive ink decreases from a region closer to the layer of conductive ink to the layer of elastic adhesive; and transferring the conductive ink pattern from the transfer substrate to the compression fabric.

As mentioned, the layer of conductive ink comprises between about 40-60% conductive particles, between about 30-50% binder; between about 3-7% solvent; and between about 3-7% thickener.

The method may also include peeling the transfer substrate off of the conductive ink pattern. The transfer substrate may comprises a paper or plastic (e.g., polyurethane) substrate. In variations using a conductive thread, the method may also include attaching a conductive thread to the compression fabric, wherein one end of the conductive thread is electrically connected to the conductive ink pattern. The transfer substrate may therefore include a conductive thread in electrical communication with the conductive ink pattern.

Transferring may be heat transferring, e.g., transferring may include applying heat to transfer the conductive ink pattern and/while placing it against the garment (e.g., ironing it on). Transferring may comprise applying heat from about 130° C. to about 300° C. to transfer the conductive ink pattern to the compression fabric. Transferring may include transferring the conductive ink pattern from the transfer substrate to the compression fabric.

Any of these methods may include printing the conductive ink pattern on the transfer substrate before placing on the compression fabric. The compression fabric may be in a relaxed (not stretched, e.g., flat/smooth but not stretched) before and/or during the transfer.

The conductive ink pattern may be printed on the transfer substrate by: printing the conductive ink onto the substrate in a first pattern; printing the adhesive onto the substrate over the first pattern; and forming the gradient region between the conductive ink and the adhesive.

A method of making a wearable electronics garment may include: printing a pattern of conductive ink and an elastic adhesive onto a substrate such that the conductive ink is substantially co-extensive with the adhesive, wherein the conductive ink comprises between about 40% and about 60% of conductive particles; and forming a gradient region between the conductive ink and the adhesive, the gradient region comprising a nonhomogeneous mixture of the conductive ink and the adhesive wherein the concentration of conductive ink in the gradient region decreases from a region closer to the layer of conductive ink to the layer of elastic adhesive. The substrate may comprise a transfer substrate (e.g., paper, plastic, etc.). The surface of the substrate may be 'non-stick' (e.g., waxed, sealed, etc.) or otherwise prepared to enhance the transfer (and removal) of the substrate. The substrate may comprise a compression fabric. As mentioned above, the conductive ink may comprise between about 40-60% conductive particles, between about 30-50% binder; between about 3-7% solvent; and between about 3-7% thickener.

In any of these variations, the pattern of adhesive and/or conductive ink may be screen printed. For example, printing may include placing a screen having openings configured as a first pattern onto the substrate and spreading the adhesive over the screen.

In general, the viscosity of the conductive ink and/or the adhesive may be selected so that it may be printed onto a substrate and/or the fabric. For example, the viscosity of the ink (uncured) may be between about 60 Poise and about 200 Poise, and the viscosity of the uncured adhesive may be similar. Viscosity decrease with temperature; in general the viscosity may be within the indicated range between a temperature of about 15° C. and about 38° C. (working range).

In some variations, printing comprises spraying the adhesive and/or conductive ink onto the compression fabric.

In general, the gradient (intermediate) region between the adhesive and the conductive ink may be formed during the printing process, either actively or passively. For example, forming the gradient region may include printing the conductive ink onto the adhesive while the adhesive is sufficiently fluid to allow diffusion of the conductive ink into an upper region of the adhesive. Diffusion of the ink and/or glue may be enhanced/inhibited by regulating the temperature (e.g., heating or cooling). In some variation a mixture of adhesive and conductive ink may be applied (e.g., mixture of 50/50 adhesive/ink, mixture of 60/40, mixture of 70/30, mixture of 40/60, mixture of 30/70, etc.).

A method of making a wearable electronics garment may include: printing an adhesive onto a compression fabric in a first pattern, wherein the adhesive is elastic when dry; printing a conductive ink onto the first pattern; and forming a gradient region between the conductive ink and the adhesive, the gradient region comprising a nonhomogeneous mixture of the conductive ink and the adhesive wherein the concentration of conductive ink in the gradient region decreases from a region closer to the layer of conductive ink to the layer of elastic adhesive.

In general, printing the conductive ink may include printing between 3 and 20 layers of conductive ink. The conductive ink may be printed so that the conductive ink does not directly contact the compression fabric. The method may also include printing an insulating resin over part of the conductive ink.

In any of the devices and methods described, the adhesive ("glue") may be a thermo-adhesive water-based glue that is electrically insulative and mechanically stretchable. For example, commercially available fabric adhesives that are water-based and electrically insulative may be used.

As mentioned above, printing the adhesive may comprises placing a screen having openings configured as the first pattern onto the compression fabric and spreading the adhesive over the screen. Similarly, printing the conductive ink may comprise placing a screen having openings matching at least a portion of the first pattern onto the compression fabric and spreading the conductive ink. As mentioned, printing the conductive ink may comprise printing a conductive ink having: between about 40-60% conductive particles, between about 30-50% binder; between about 3-7% solvent; and between about 3-7% thickener.

In general, printing the adhesive onto a compression fabric may comprise spraying the adhesive onto the compression fabric; printing the conductive ink may include spraying the conductive ink onto the first pattern. As also described above, forming the gradient region may include printing the conductive ink onto the adhesive while the adhesive is sufficiently fluid to allow diffusion of the conductive ink into an upper region of the adhesive.

Also described herein are wearable fabric strain gauge devices (e.g., the conductive elastic strip or ribbon sensors described herein). These device may include an elongate length of elastic fabric impregnated with a conductive material, wherein the conductive material comprises conductive particles at between about 85% and 99% of the conductive material and a binder, wherein the binder is between 0.1% and 15% of conductive material; a first conductive (e.g., metal) connector attached at a first end of the elongate length of elastic fabric impregnated with the conductive material; a second conductive (e.g., metal) connector attached at the second end of the elongate length of elastic fabric impregnated with the conductive material; and a covering over the elongate length of elastic fabric impregnated with the conductive material, wherein the covering comprises a compression fabric.

These devices, which may be configured as respiratory sensors or may otherwise be used to detect stretch (e.g., of the garment to which it is attached) may also include a conductive thread sewn into a length of compression fabric in a zig-zag or sinusoidal pattern and electrically coupled to the first metal connector. For example, the garment may include a first conductive thread sewn into a first length of compression fabric in a zig-zag or sinusoidal pattern and electrically coupled to the first metal connector and a second conductive thread sewn into a second length of compression fabric in a zig-zag or sinusoidal pattern and electrically coupled to the second metal connector. The lengths of compression fabric may be part of different pieces of compression fabric, or they may be part of the same compression fabric forming the covering.

The conductive material may be formed from a suspension of conductibe particles, such as particles of carbon black, graphene, graphite, and mica coated with oxide (or any of the other conductive particles described herein). In general, there is much more conductive particles than binder; in the dried state, the conductive particles may be between about 60% and 99.9% (or between about 70% and 99.9%, 80% and 99.9%, 85% and 99.9%, 90% and 99.9%, 70% and 99%, 80% and 99%, 85% and 99%, 90% and 99%, etc.) of the conductive material. The binder may be between 0.1% and 20% (or between 0.1% and 15%, between 0.1% and 12%, between 0.1% and 10%, between 0.1% and 7.5%, between 0.1% and 5%, between 0.1% and 2.5%, between 0.1% and 1%, etc., between 1% and 20%, between 2% and 20%, between 5% and 20%, between 7.5% and 20%, etc.). The binder may be acrylic or water based polyurethane.

In general, these devices may exhibit low electrical and mechanical hysteresis. For example, the devices may exhibit less than 5% (less than 4%, 3%, 2%, 1%, 0.9%, 0.5%, 0.2%, 0.1%, etc.) electrical hysteresis after elongating more than twice its lengths (e.g., more than 2.5× length, more than 3× length, more than 4× length, etc.). The elongate length of elastic fabric may returns to its original length in less than about 2 second (less than 1.5 sec, less than 1 sec, less than 0.8 sec, less than 0.6 sec, less than 0.5 sec, less than 0.4 sec, less than 0.3 sec, less than 0.2 sec, less than 0.1 sec, less than 0.05 sec, etc.) after elongating more than twice its length.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A shows a front view of a shirt configured as a respiration monitoring garment.

FIG. 1B is a partial view of the front and lateral regions of the shirt of FIG. 1A.

FIG. 1C shows a back view of the same garment of FIGS. 1A and 1B.

FIGS. 1D, 1E and 1F show front, front and lateral, and back views, respectively of another garment configured to measure regional respiration, similar to the garment shown in FIGS. 1A-1C.

FIG. 3A is a front view of another variation of a garment for measuring ECG in which the limb leads are positioned on the shirt, e.g., not requiring leg leads. For example, when exercise stress tests are performed, limb leads are often placed on the trunk to avoid artifacts while ambulatory (arm leads moved subclavicularly, and leg leads medial to and above the iliac crest).

FIG. 3B is a back view of the garment of FIG. 3A.

FIGS. 4A and 4B show front and back views, respectively, of a garment configured to detect ECGs.

FIGS. 13A and 13B show front and back views, respectively, of a garment.

FIGS. 14A and 14B illustrate front and back views, respectively of a garment with a support garment.

FIGS. 14C and 14D illustrate a front and back view, respectively of a support garment that can be used with the garments described herein.

FIGS. 15A and 15B illustrate an inflatable support device in accordance with some embodiments.

FIG. 15C illustrates the inflatable support device relative to a female chest.

FIGS. 16A and 16B illustrate a front and back view, respectively of a support garment that can be used with the garments described herein.

FIGS. 18A and 18B illustrate front and back views, respectively of a garment with a support garment.

FIG. 20 illustrates a wiring diagram for pants in accordance with some embodiments.

FIG. 21A illustrates a wiring diagram for the front of a garment in accordance with some embodiments.

FIGS. 22B and 22C show front and back views, respectively of another variation of a garment such as the one shown in FIG. 22A, having a IMUs arranged on the arms and legs, but also including EMG electrodes on the arm, legs and buttocks. Elastic fabric may be integrated into the compression fabric as shown, to further enhance the contact between the EMGs and the subject's skin. Five or more IMUs may be attached across the garment, including along the subject's back, corresponding to different spine regions, as shown in FIG. 22D. This may allow detection of posture for postural feedback, etc.

FIG. 23 shows one example of an elastic ribbon 2301.

In FIG. 24, a solution including a suspension of electrical conductor (carbon black dispersed in water in this example) is placed in a container and, in FIG. 25 an elastic material (e.g., a material formed of fabric and polymeric material) is dipped into the suspension material so that the conductive material may be absorbed in to the fabric of the elastic material. In FIG. 26, the elastic material is covered in at least a first uniform layer. Thereafter, the coated material may be dried, as shown in FIG. 27.

FIG. 40A-40D are micrographs illustrating the distribution of chemical components (e.g., carbon in FIG. 40A, sulfur in FIG. 40B, silicon in FIG. 40C and oxygen in FIG. 40D) of a stretchable conductive ink composite (pattern). Large arrows on each micrograph indicate the visual display of chemical composition.

FIG. 42A shows different patterns of stitches, having different pitches and widths (angles); FIG. 42B shows an example of five parallel conductive threads that may connect to five different sensors. FIG. 42C shows an example of a single conductive thread. These conductive threads may form wire ribbon material (e.g., stitched zig-zag connectors) as described herein.

FIGS. 44A-44B illustrate one variation of a garment (respiration sensing garment) including a plurality of conductive particle impregnated elastic strips configured as strain gauges for detecting respiration. FIG. 44A is a front view and FIG. 44B is a back view, respectively.

FIG. 45 illustrates one method of fabricating a garment for sensing respiration as described in FIG. 44A-44B.

FIGS. 46A and 46B shows side-by-side comparison of ECG measurements using a standard 12-lead ECG machine (FIG. 46A) and a garment as described herein (FIG. 46B), for each of leas I, II, III, aVR, aVL and aVF.

FIG. 47B is a comparison of the average breaths per minute calculated using a reference system (a standard plethysmography system including a face-mask through which breathing is monitoring), and a respiration monitoring garment as described here ("RR Band System"), showing excellent agreement between the two.

DETAILED DESCRIPTION

Figure 2B:
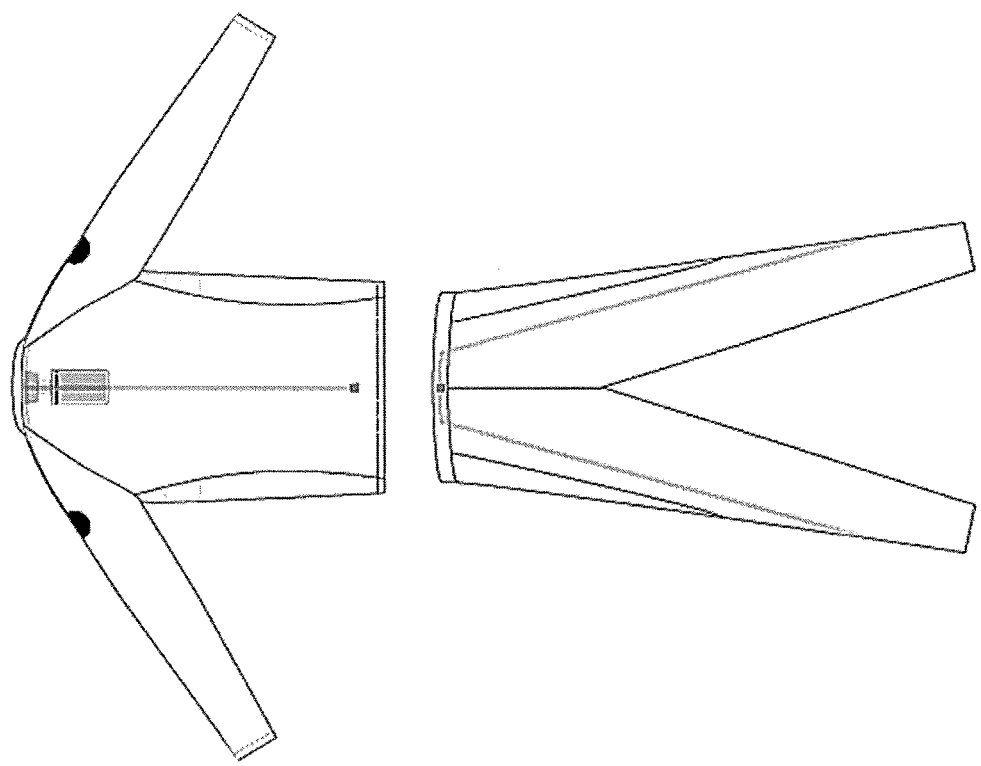
FIG. 2B is a back view of the garment (shirt and pants) of FIG. 2A.

In general, described herein are apparatuses (e.g., garments, including but not limited to shirts, pants, and the like) for detecting and monitoring physiological parameters, such as respiration, cardiac parameters, sleep, emotional state, and the like. In particular, described herein are stretchable, conductive sensors and connectors, which may include stretchable conductive inks, elastics, and traces that may be attached (e.g., sewn, glued, etc.) or in some variations printed onto garments, including in particular compression garments, to form sensors, conductive traces, and/or contacts.

U.S. patent application Ser. No. 14/023,830, titled "PHYSIOLOGICAL MONITORING GARMENTS," and filed on Sep. 11, 2013 (incorporated by reference herein) describes exemplary garments any of which may be modified as described herein.

Any of the garments described herein may include one or more Sensor Manager System (SMS) placed directly onto the garment (e.g., shirt, shorts or in any other component of the wearable device, i.e. balaclava, socks, gloves, etc.), or integrated into the garment, as described in greater detail below. The SMS may include an electronic board. Connections to the SMS may be made by connectors including wire ribbon material (e.g., a stitched zig-zag connector) that may be included as part of the garment. In some variations a length of rigid material (e.g., Kapton) onto which conductive traces are attached, may be used.

An SMS that is integrated into the garment (as opposed to being provided by a separate device such as a smartphone) may provide numerous advantages. For example, an integrated SMS can manage a larger number of connections with the different sensors, and may processes the signals and communicates with the phone by means of a single mini-USB cable (e.g., independently of the number of signals processed). No matter the number of sensors that will be included in future devices (e.g., shirt, thighs, gloves, socks, balaclava, etc.), the connection between SMS and sensor module (e.g., phone) may always be based on a single 5-pin USB connection, thus substantially reduce the size of the female and male connectors from the device to the phone module. In a typical configuration, an SMS connects to a male connector through a UART (Universal Asynchronous Receiver-Transmitter) module and the male connector communicates to the mobile through another UART and an UART-to-USB module (see attached schematic and drawings).

An integrated SMS can be placed in different locations on the garment. For example, it may be placed at the base of the neck between shoulder blades, on the lumbar region on the thighs, on the arms, chest, or even on the socks, gloves, balaclava, etc.

An SMS may also be configured to communicate with different phones for the device. As mentioned, an integrated SMS may also allow you to have more connections (pins) to connect to different sensors/outputs. For example, an accelerometer may need 5 pins if you have the SMS present in a sensor module (e.g., mobile phone); an SMS integrated into the shirt may need fewer connectors, for example, such an SMS may need only 2 pins. With more sensors, without an integrated SMS the number of connectors may become unfeasible.

In general, the SMS may be a module (chip) that manages the signals from and to the sensors, and may act as an interface between the communication system (sensor module configured from a phone, etc.) and sensors. The SMS may manage the connection and interfaces between them. For example, and integrated SMS may include physical connections to sensors and may manage the way in which the signals are processed and sent between sensors and a sensor module and/or other analysis or control components. The SMS may also include or may connect to a multiplexer to alternate readings between various sensors to which it is connected.

In some variations, a SMS may provide proper power supply to passive sensors or active sensors. An SMS may take power from the mobile systems through a port such as a USB port. An integrated SMS may communicate from one side to a sensor module (e.g., communications systems/phone, etc. configured as a sensor module) through a USB port. The SMS may act as an interface or a bridge between the sensors and the sensor module.

In addition, any of the integrated SMSs described may be configured to include on-board processing (e.g., preprocessing), including, but not limited to: amplification, filtering, sampling (control of the sampling rate), and the like; typically basic pre-processing. An integrated SMS may also encode signals from the one or more sensors. In some variations the SMS may include a microcontroller on board. Further, and integrated SMS may also generally manage communication protocols to/from any or all of the sensors, and may make an analog to digital conversion (if the signals are analog) and may also communicate with a comm port of a USB, before going to the USB. For example, an SMS may be configured to convert the signal into UART to the USB signal protocol.

In addition or alternatively, any of the integrated SMSs may be configured as a signal receiver/transmitter. For example, an SMS integrated into the garment may be adapted to convert parallel signals to serial signals (in the order of the data).

As mentioned, an integrated SMS may be placed in any position on a garment, e.g., on or near the neck region, or more peripherally. Although the SMSs describe herein are referred to as "integrated" SMSs, these SMSs may be included on or in the garment (e.g., in a pocket or enclosure, though in some variations it is not physically connected/coupled to the fabric, but is instead placed on the garment. Thus, any of these SMSs may instead be referred to as dedicated or specific SMSs rather than (or in addition to) integrated SMSs. For example, the SMS may be placed under the female connector (housed inside the female connector), as part of the garment. When you wash the garment the SMS may get washed with the connector and the chip; the pins and SMS are waterproofed.

In some variations, the connectors (e.g., pins/ports) of the SMS are adapted to water resistant/water proof. For example, the pins used may make connections that are waterproof, e.g., with connections that only open when you engage the male pin, but are otherwise closed and waterproofed.

In any of these integrated SMSs, the SMS is a part of the garment, and are worn with the garment; the SMS module may pre-process the signal(s) to prepare them for transfer.

Thus, in any of the garments described, an SMS (Sensor Management System) may be included that is positioned on each garment (onboard/dedicated), rather than separate from the garment, e.g., as part of a separate sensor module, such as a general-purpose smartphone that may be held in a pocket on the garment, as previously described. Each garment may have an SMS (chip/microchip) that allows the garment to have connectors (female and male) with a numbers of pins (inputs/outputs) so that data from all the sensors in the garment (shirts, tights and accessories, such as gloves, socks, balaclava, etc.) may be first processed by the SMS and then sent through a connection (e.g., as few as 1 or 2 pins, or more) to the phone/communication module. In general, some of the sensors and components of the garments described herein may individually require multiple connections and thus a dedicated SMS may be very useful. For example, an IMU may require 5 pins and as many as 20 IMUs (or more) may be included as part of a garment, in addition to other sensors. Thus, the use of a dedicated SMS may allow the garment to manage a large number of data connections/contacts.

Sensors

In addition to the sensors described in the Ser. No. 14/023,830 application included by reference in its entirety herein, such as touch point sensors, respiration sensors, bioelectrical sensors, etc., additional sensors may be included in any of the garments described herein. For example, a garment may include one or more skin conductance sensor. A sensor for measuring skin conductance can be made by two annular rings of the stretchable, conductive ink (see below) placed at the level of the third phalange of whatever couple of fingers (thumb, index, middle, ring and little finger). In some variations, the sleeve of the shirts has at the wrist level an integrated extension for this purpose. The skin conductance, depending on the sweating level, is measured as the inverse of the electrical resistance between the two considered 'electrodes' (annular rings).

Another integrated extension of the apparatuses described herein includes a full glove that, in addition or instead of a skin conductance sensor, incorporates a pulse-oximetry based on optical fibers. The use of optical fibers may also allow the incorporation other types of sensors. In addition, a full or partial glove may include additional sensors such as accelerometers, inertial measurement units (IMU), etc. Such glove-based sensors may allow applications in specific activities (e.g. playing a music instrument, type writing, etc.). A glove or pair of gloves may be configured to connect to other garments (e.g., shirts, etc.) or be formed as a sub-region of another garment (e.g., a shirt with finger regions/gloves, etc.).

Similarly to the gloves described above are socks or balaclava extensions, that incorporate other types of sensors, such as accelerometers, inertial measurement units (IMUs), EEG electrodes, etc. This allows applications in specific sports (e.g. football) and activities (e.g. playing chess).

Production Processes

In general, the production of any of the garments described herein may include constructing the garment such as the sensors are held close and in stable contact with the skin. Thus, the sizing of the garment may be very precise, particularly in the following areas: thorax (because of different sizes of pectorals and breasts despite same corporeal size), abdomen (same reason), armpits, forearms, etc. The garments may be therefore precisely fit/manufactured, in addition to being made from compression materials. The design process may also include garment cutting.

Thereafter, any of the garments described herein may then be printed by, e.g., printing and transferring of the conductive ink traces and/or insulation. The printing may be performed by cylinder-type machines (because the printing is more precise and faster) using a heat transfer technique. For example, transfer on both sides of the fabric is performed at 150° C. for 15 seconds. Alternatively, garments may be printed by 3D printing, as discussed briefly below.

Thereafter, insulation may be applied (e.g., when capacitive touch points are used, such points may be insulated). The internal regions (i.e., in contact with the skin) of electrodes of a capacitive touch point may be insulated by heat-welding a layer of high quality polyurethane film exactly reproducing the shape of the electrodes. The size of the insulation layer may be slightly larger than the size of the electrode to allow a complete covering thus to avoid 'lateral' contamination of biopotentials.

In variations in which higher conductive connections are used, the apparatus may include the addition of higher-conductive substrates and materials, such as wire ribbon material (e.g., stitched zig-zag connectors) as described herein. Thus, the formation process may then include the application of these wire ribbon material connectors, which may include connecting the ends of the wires (forming the wire ribbon material) to the sensor(s) and/or SMS components. The wire ribbon material may include a substrate of compression fabric that may be fused, glued, stitched, or otherwise connected to the body of the garment. For example, once positioned, the wire ribbon material (e.g., a stitched zig-zag connector) may be secured to the fabric through high quality polyurethane tapes for heat-welded applications. In some variations, rather than (or in addition to) the wire ribbon materials, a more rigid or semi-rigid substrate may be used, such as Kapton, onto which electrical traces, and/or circuitry, may be printed. In order to maximize comfort of movement, the electronics on the Kapton may be designed to have a single layer, thus minimizing its thickness.

The garment may then be sewed. The sewing may be performed by traditional processes, although in some variations, sewing over conductive ink, the wire ribbon material, or Kapton traces may be avoided.

At the same time or thereafter, soldering may be performed, e.g., to connect the wire ribbon materials, and/or regions including an additional (e.g., Kapton) substrate for higher-conductive traces, with printed conductive ink sensors, electrodes and/or traces. For example, soldering between ink traces and Kapton terminals may be performed by using conductive epoxy, successively covered by a high quality polyurethane film.

Thereafter, in some variations a semi-rigid collar region may be attached, e.g., to secure and cover an integrated SMS module and connectors. A collar may be made of a polyurethane material that takes the shape of the user's shoulders and may be applied by thermal welding through a transfer machine with plates custom-made to fit the body surface in the neck region.

In some variations, the method of forming the garments may also include the addition of 'stretching limiters' made, e.g., of stripes of polyurethane material with limited elongation. They may be positioned by thermal welding in the inner part of the garment, in proximity of long ink traces (e.g. respiration traces), in order to prevent overstretching (e.g. during wearing) that could either break a trace, or determine permanent elongation, that must be avoided for functional and aesthetic reasons. To enhance their strength, they may be positioned in a way to run between two seams.

In some variations the garment may be produced by installing a silicone cord. To avoid stretching of the garment and its sensors when the user is wearing the garment and putting the garment on, a cord made of silicon may be applied (e.g., by thermal welding) to the lower edge of the garment, running all around the edge. This may allow the wearer to easily pull the shirt down from the armpits to the waist after the collar and the sleeves have been inserted, without overstretching the garment.

As mentioned above, the garment described herein may be made entirely or in part by a 3D printing technique. For example, sensors and/or conductive traces and/or connectors may be produced by 3D printing. In some variations a fabric (e.g., compression garment fabric) may act as a substrate for the 3D printing. In some variations the fabric may itself be created or modified by 3D printing. Thus, a garment may be made by transfer and direct printing (3D printing). In, one example, a 3D printer for producing a garment including the integrated sensors described such as those described herein may include at least three nozzles: one nozzle may be adapted to print a compression garment fabric; one nozzle may be adapted to print/insert a stretchable conductive ink; and one nozzle may be adapted to print/insert sensors and/or electronics. In contrast with currently practiced methods, which may require weaving the fabric (e.g., from thread), printing the electronics and sensor on the fabric (or onto a substrate and then transferring to the fabric), then sewing the fabric, in 3D manufacturing, production can go directly to printing threads, ink and electronics based on precise personal measurements from a person, which may be both more accurate and faster.

Materials

In general, the garments described herein may include a compression fabric to secure that sensor are in good permanent contact with the skin. For example, the anterior part of the shirt may have a lower percentage of elastane (between 5 and 20%) than the rest of the body, which may include a higher percentage of elastane (between 15 and 40%). The fabric may be stretchable into two ways (one direction) and may be positioned with the least stretchable side placed horizontally to respect human body which dynamically stretches more horizontally than vertically. In general, a compression fabric may be any fabric having the material properties associated with compression fabrics as described herein. Examples including materials such as fabrics made of elastic polyurethane fibers (e.g., elastin fibers, Lycra, etc.).

As discussed in greater detail below, any of these garments may include a stretchable conductive ink and/or a stretchable insulator (over/surrounding) the conductive ink. Both the conductive ink and the insulator may be stretchable, up to some percentage, X% stretchable (e.g., up to 5% stretchable, up to 6% stretchable, up to 7% stretchable, up to 8% stretchable, up to 9% stretchable, up to 10% stretchable up to 11% stretchable, up to 12% stretchable, up to 13% stretchable, up to 14% stretchable, up to 15% stretchable, up to 16% stretchable, up to 17% stretchable, up to 18% stretchable, up to 19% stretchable, up to 20% stretchable, up to 21% stretchable, up to 22% stretchable, up to 23% stretchable, up to 24% stretchable, up to 25% stretchable, up to 30% stretchable, up to 35% stretchable, up to 40% stretchable, up to 45% stretchable, up to 50% stretchable, etc.). This may also be expressed as more than X% stretchable (e.g., more than 5% stretchable, more than 6% stretchable, more than 7% stretchable, more than 8% stretchable, more than 9% stretchable, more than 10% stretchable more than 11% stretchable, more than 12% stretchable, more than 13% stretchable, more than 14% stretchable, more than 15% stretchable, more than 16% stretchable, more than 17% stretchable, more than 18% stretchable, more than 19% stretchable, more than 20% stretchable, more than 21% stretchable, more than 22% stretchable, more than 23% stretchable, more than 24% stretchable, more than 25% stretchable, more than 30% stretchable, more than 35% stretchable, more than 40% stretchable, more than 45% stretchable, more than 50% stretchable, etc.). Stretchable typically mean capable of being stretched (e.g., by applying a force such as a pulling force) from a starting length/shape and returning to approximately the starting length/shape. In some variations may mean additionally or alternatively, resisting breaking when a deforming force (elongating or distorting from the original length/shape) is applied (and eventually released). Examples of stretchable conductive inks and characteristics of such inks are provided below.

As mentioned, any of the garments may also include a substrate attached or formed as part of the garment for higher-conductive paths, such as Kapton films. Other flexible, wearable substrates may also be included. Any of the garments may also include one or more polyurethane films and tapes for sewn and heat-welded applications (e.g., high-quality polyurethane films and tapes). In addition any of the garments may also include an electrical insulation material (e.g., polyimide materials, etc.) for covering/insulating a conductive trace, forming a part of a sensor, or the like.

A substrate such as Kapton may be fixed to on onto the garment. For example, the substrate may be sewn and/or attached by an adhesive, etc. The substrate may be held in a pocket or other region of the garment. As mentioned above, any of the garments may include a limiter (e.g., stretch limiter) of a second material (e.g., a cloth material that is less stretchable than a compression garment, etc.).

Any of these garments may also or additionally include silicone for sewn and heat-welded applications.

Stretchable Conductive Inks

In general, the stretchable conductive inks products described herein may be formed of an adhesive (e.g., glue, such as acrylic, polyamide and other adhesives) onto which a printable mixture of conductive solution is applied. The wet-applied conductive solution (which may be referred to for convenience as the conductive ink, even though the final conductive ink product includes the adhesive material layer) is typically applied as a layer onto the layer of adhesive, so that an intermediate region between the adhesive and the wet-applied conductive solution forms. This intermediate region may be important for the conductive and stretchable properties of the resulting conductive ink material. The intermediate region is a gradient region, because it defines the concentration gradients of the adhesive layer and the wet-applied conductive solution (conductive ink). This is illustrated and described below.

A stretchable, conductive ink (the we-applied conductive ink layered against the adhesive) typically includes a percentage of conductive material (e.g., around/approximately 20%, 25%, 30%, 35%, 40%, 45%, 50%, 55%, 60%, 65%, 70%), and a biocompatible binder (e.g., acrylic binder that is formaldehyde-free such as water-based acrylic binders, water-based polyurethanes, etc.), a thickener (e.g., polyurethanic thickener) and an optional humectant and/or solvent (e.g., propylene glycol). The stretchable conductive inks as described herein generally meet a minimum conductance as well as a minimum stretching property. The stretchable conductive ink may also optionally include a de-foamer to eliminate air/foam when processing (e.g., 1-butanol), a catalyst (e.g., to aid in crosslinking of the binder, e.g., amine compounds or metal complexes), and additional additives which may help with the printability and stability of the product.

In one example, a stretchable conductive ink (and particularly the wet-applied conductive ink portion) is formed of: 50% Carbon Black, 40% Acrylic Binder, totally formaldehyde-free, 5% propylene glycol, and 5% polyurethanic thickener. The conductive material (Carbon Black) may be particulate. Carbon Black may be preferred, particularly compared to other conductive materials such as silver or other metallic. Other conductive materials may include graphene, graphite, coated mica (e.g., mica coated with an oxide, such as antimony-doped tin dioxide, etc.), or the like.

The conductive inks described herein are not only conductive, but also stretchable and therefore can work properly on compression garments. In addition, the stretchable conductive inks appropriate for forming the garments described herein may be ecologically appropriate (e.g., having a formaldehyde concentration lower than 100 ppm), and resistant to washing (with preservation of electrical and elastic properties after multiple washes).

Figure 6:
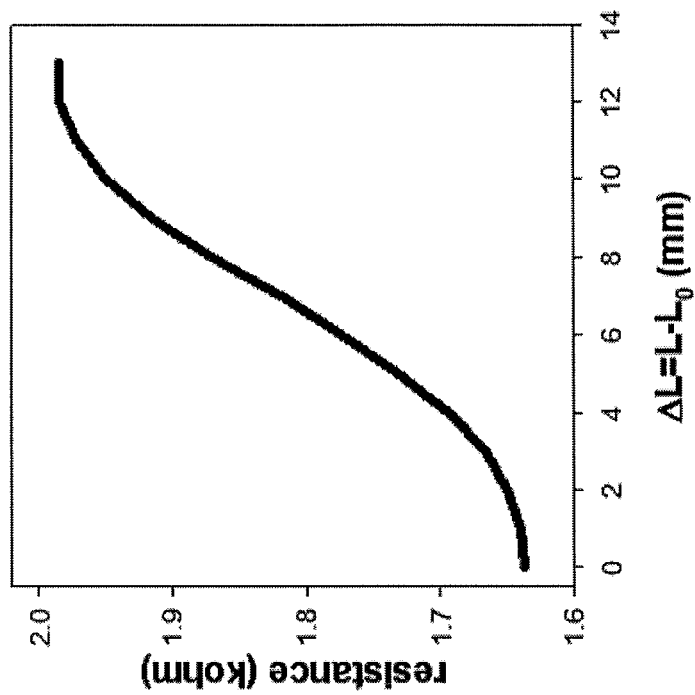
FIG. 6 is a graph characterizing the resistance for one variation of stretchable conductive ink.
Figure 5:
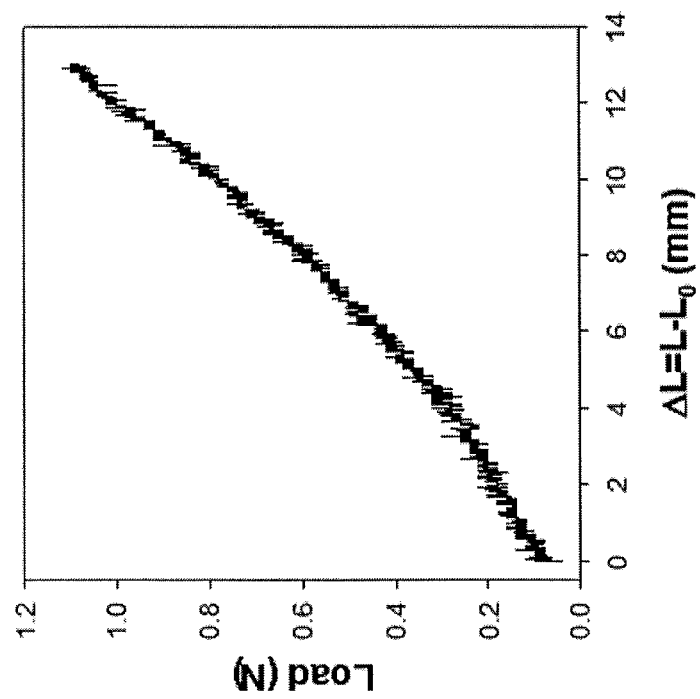
FIG. 5 is a graph characterizing the force vs. extension for one variation of stretchable conductive ink.

Experimental studies have confirmed that the stretchable conductive ink compositions (layered structures including the intermediate, gradient region between the adhesive and the wet-applied conductive ink) described herein are stretchable. FIGS. 5 and 6 illustrate preliminary results of testing conducted on a sample of conductive ink printed on a compression textile as described above. A video camera was used to demonstrate that no fractures developed in the ink during the extension (e.g., change in length of up to 13 mm was examined). The conductance (e.g., resistance) varied with applied force between approximately 1.6 kOhms to 2 kOhms, while a linear stretch was observed up to 1.1 N (e.g., stretch up to approximately 13 mm without breakage at approximately 1.1 N). In general, the stretchable conductive inks described herein may be within a performance range of being stretchable up to at least 1 N of force (e.g., up to at least 2 N, up to at least 3 N, up to at least 4 N, up to at least 5 N, up to at least 6 N, etc.) and/or stretchable (without breaking) up to at least 5 mm (e.g., up to at least 6 mm, up to at least 7 mm, up to at least 8 mm, up to at least 9 mm, up to at least 10 mm, up to at least 11 mm, etc.) and/or stretchable up to a ratio of applied stretching force (in N) to extension length (in mm), e.g., around about 1 N/mm without breaking. Surprisingly, in the experiment shown in FIG. 5, the conductive traces examined did not evidence any breakage up to almost 2 N, which is a reasonable near-maximal force that may be applied when applying/wearing a garment. Neither macro (visible to the naked eye) nor micro breakage was apparent.

In general, the resistance of the stretchable conducive ink may depend upon the size of the trace, including thickness, length, etc. (which may vary under stretch) and may be lower than about 5 kOhm (e.g., less than about 4 kOhm, less than about 3 kOhm, less than about 2 kOhm, etc.) at rest and under a predetermined stretch force (or force/stretch length). In general, the resistance may be within a range of a few hundred Ohms to a few hundred kOhms. In FIGS. 5 and 6, the tested stretchable conductive ink was printed on the compression garment fabric to a length of 60 mm and a width of about 10 mm; eight layers of ink were applied to form the final thickness (which was less than about 2 mm (e.g., approx. 1 mm or less).

Stretchable conductive inks that may be used to forms trace, connectors and/or sensor in any of these garments described herein are described in greater detail below.

Systems

Any of the garments described herein may be used as part of a system including multiple garments that connect (either or both directly connect or wirelessly connect). For example, and upper body garment/device may connect with lower body garment/device. Signals from sensors positioned on garments on the lower part of the body (e.g., shorts, thighs, socks, etc.) may be transmitted to one or more SMS, e.g., on an upper garment such as a shirt, etc. A connection may be made through a support substrate (e.g., Kapton) including traces that can connect through a connector positioned in an internal portion of the upper garment (e.g., the lower hem region of the upper garment).

In general, the garments described herein may include a body formed of a fabric. In particular, compression fabric materials are useful. The body may include a plurality of sensors positioned in predetermined locations on the garment. The sensors may be on the inside of the garment (e.g., facing the wearer), or they may be on the outside of the garment. Connectors may connect the sensors to one or more sensor manager/sensor module (SMS) that may include a processor. The SMS may either directly transmit or connect/couple to a sensor manager unit (SMU) for recording/analyzing/transmitting the sensed data, or it may itself perform some or all of these functions. In general, the sensors may be formed at least in part of the stretchable conductive ink structures described herein (e.g., as used herein, "stretchable conductive ink" structures may refers to the combination of the wet-applied conductive ink, adhesive and gradient/intermediate region between them described herein). A sensors including the stretchable conductive ink may include a touch point (e.g., capacitive) sensor, a skin electrode sensor, or the like. Also described herein are sensors formed at least in part of conductive elastic ribbon (e.g., elastic saturated with conductive particles in a base/binder, as described herein), which may form strain gauges or other sensors. The connectors may be formed of stretchable conductive ink and/or conductive elastic ribbon. In some variations the connector is formed of a wire ribbon material (e.g., stitched zig-zag connector) in which enameled wires are sewn onto strips of material (e.g., compression fabric) in a sinusoidal/zig-zag pattern, and the ribbon is applied to the body of the garment. In some variations the connector may be a rigid or semi-rigid substrate (such as Kapton) onto which electric traces and/or circuitry are applied; the substrate may be attached and/or covered in fabric such the compression fabric and attached to the body of the garment, or directly attached to the body of the garment.

Any type of garment may be formed as described. For example, described herein are garments configured as medical devices, or for use a medical device, including a monitoring device, therapeutic device, or aid. The body of these garments may be formed of a compression fabric (entirely or in part), and the garment may be fit to the body, to help adhere the sensor(s) against the subject's body securely. In some variations the garment (e.g., medical device) may include additional elements, such as straps, halters, bra, yoke, harness, etc., or the like to help secure a portion of the garment against the subject's body. In some variations the garment may include an expandable (e.g., inflatable) support structure on a portion of the garment to help hold or secure a sensor (or sensors) against the subject. An expandable support structure may be used with a harness. The harness may be separate, or it may be integrated into the garment.

For example, described herein are garments configured to sense electrocardiographic (ECG) signals for recording and/or analysis. Such garments may be configured to connect to the wearer's (subject's) upper body, and may be in the form of a shirt or may include a torso covering. These garments may include at 5 or more electrodes, e.g., six chest electrodes and three or more electrodes for each of the right arm, left arm and a leg. Additional electrodes may be used. In some variations, the chest electrodes are pairs of electrodes that may be redundant.

Any of these garments may also or alternatively include one or more respiration sensor(s). In general, these respiration sensors include a fabric and/or conductive ink-based strain gauge. For example, the strain gauge may be formed of the stretchable conducive inks described herein and/or the conductive elastic strips described herein. In one variation, the garment includes 10 ECG sensing electrodes, 2 respiration sensors (strain gauges). The ECG electrodes may be located on the chest of the garment so that they contact the skin of the user in the position where standard 12 leads would be placed. The respiration sensors may be positioned on garment so that the compression garment, when worn, holds them against the body near the Xyphoid and Umbilicus height on the subject's torso. The sensors may be connected to SMS units by traces, such as an elastic strip with a copper-wire ribbon and/or a stitched zig-zag connector. The garment may include both a shirt (and some variations, tights).

Also described herein are garments configured to measure respiration (including regional respiration). For example, a garment may be configured to include a shirt portion formed of compression fabric that detects respiration (e.g., to allow plethysmography of the sensed signals). The apparatus may also include electrodes as described above to detect a simple ECG signal (e.g., having 2 electrodes, or a single lead, or multiple leads, e.g., 3 leads, 5 leads, 12 leads). For example, 12 respiration sensors (e.g., conductive elastic strip strain gauges as described herein) may be included. The respiration sensors may be located for positioning on the wearer near the Louis angle, 3rd costal interspace, xyphoid, lower costal margin, above the umbilicus, and below the umbilicus. There may be duplicate (e.g., left side/right side of the wearer's trunk) sensors. The sensors may be connected to one or more SMS units via a connector such as a stitched zig-zag connector (e.g., in which a strip or tube or compression garment fabric is stitched in a sinusoidal pattern with an insulated/enameled copper wire). See, e.g., FIGS. 44A-44B, showing the 12 respiration sensors.

Garments as described herein may also be configured a garments to sense sleep disorders, and may include a head covering portion as well as a torso and/or pant portion. Such garments may include, e.g., EEG electrodes (e.g., one or more) and thus ECG electrodes, respiration sensors, and one or more Inertial Mass Unit (IMU) to detect activity level and basic movements. For example, a garment may include 21 EEG electrodes (formed of stretchable conductive ink, or alternatively standard medical electrodes may be used), two ECG electrodes (formed of stretchable conductive ink), and 2 respiration sensors (formed of conductive elastic strips), and five IMUs. The EEG electrodes may be positioned as a simplified 10-20 system on a head covering, while the ECG electrodes may be positioned on the right and left trunk portion of the garment. Respiration sensors may be positioned so that they are worn near the xyphoid and umbilicus. The IMUs may be positioned on the lower back and limbs (e.g., arms on the shirt, legs on the tights)

Garments for use as a fitness tool or aid are also described herein. For example, described herein are garments configured as a fitness device may include sensors for detecting body status and athletic performance. These garments may monitor body status (e.g., well-being) by sensing and/or measuring indicators of heart rate, respiration, body fat, movement, posture, and stress-level. For example one variation of a fitness garment may have a body formed of a compression fabric with two ECG sensors (electrodes, e.g., formed of stretchable conductive ink), one respiration sensor (e.g., formed of a conductive elastic strip), and four IMUs. The ECG electrodes may be positioned in the garment to be held against the right and left trunk regions, the respiration sensor may located on the garment to be held against the xyphoid region, and the IMUs may be positioned on the lower back, one in each forearm, and one in an SMS unit (e.g., near neck region). In some variations the apparatus may also include body fat sensors at the wrists, neck and umbilicus region. A body fat sensor may be an electrode (e.g. formed of a stretchable conductive ink).

Figure 22A:
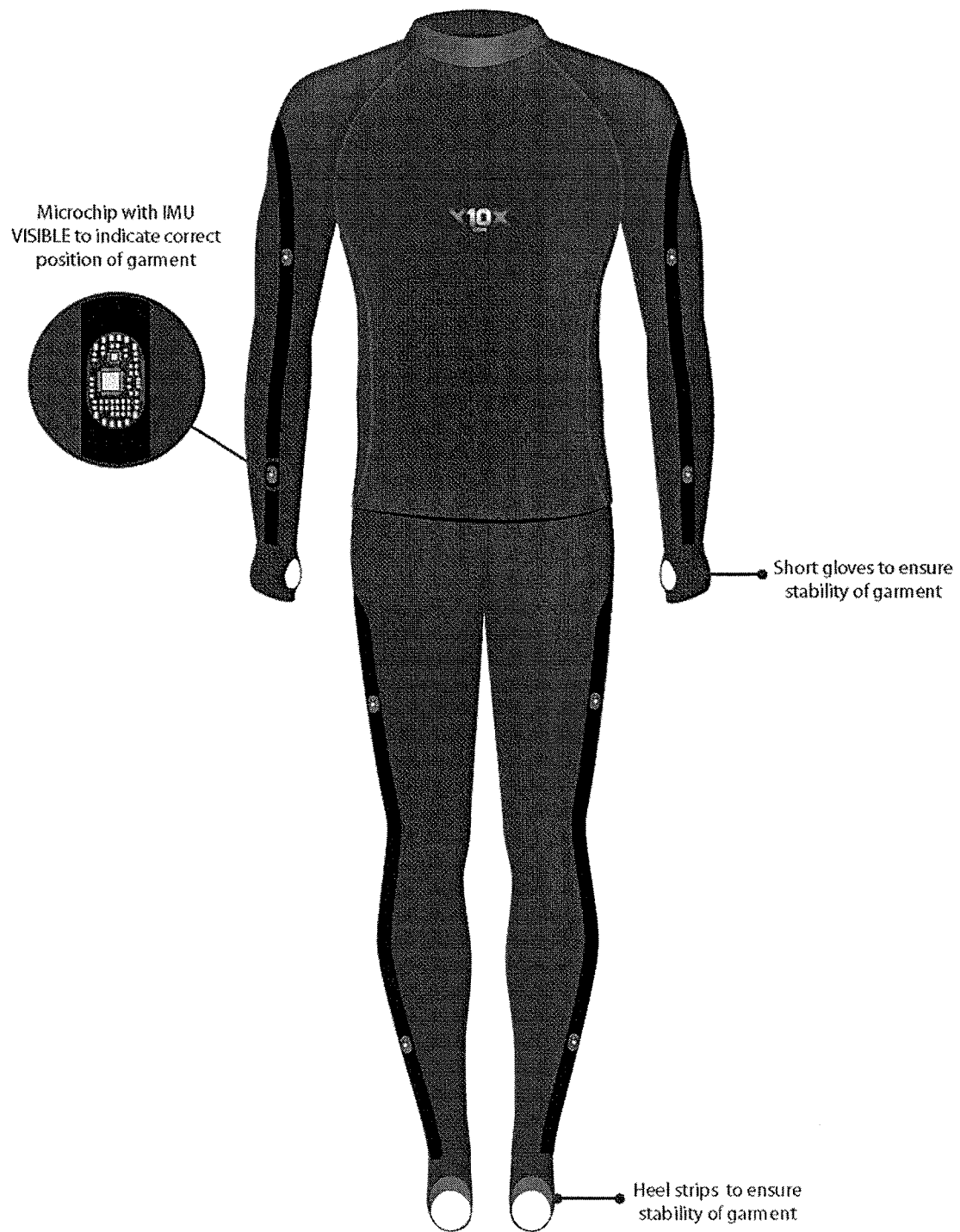
FIG. 22A illustrates another example of a garment as described herein, including sensors (not visible) and IMUs attached to the upper and lower legs, and upper and lower arms on both the right and left sides of the body.

Another variation of a fitness garment (e.g., general fitness garment) may be configured as a shirt to be worn on the upper body. As mentioned, these garments may be used to monitor general well-being, and may operate with a controller that compares data for references as well as evaluating basic fitness skills such as coordination, equilibrium, stamina, 'breath', strength, flexibility and reflexes. In some variations, the garments include at least three (e.g., 4) IMUs in the upper portion (the shirt, e.g., upper and lower arm, left/right) and at least three (e.g., 4) IMUS in the lower portion (e.g., pants/tights, upper and lower leg, left/right), a respiration sensor (in a region to be worn against the umbilicus region). See, e.g., FIG. 22A-22D. In the example shown in FIG. 22B, the system has two parts; a shirt for detecting posture and monitoring fitness; and a pair of pants that can connect to the shirt or separately connect to a processor. In FIG. 22B, the shirt 2204 and pants 2205 including EMG sensors 2221, shown as parallel lines of sensors. IMUs 2225 are also positioned at the upper and lower legs, upper and lower arms, and along the back, so as to detect postural changes. Bands of elastic material 2231 are integrated into the compression further help hold the electrodes (e.g., EMG 2221) against the skin, as shown by the darker regions.

In general, any of the garments may operate with/connect to a processor that can store, transmit, compress, and/or analyze the recorded data.

Examples of these various types of garments are described below.

Garments that Detect Respiration

Garments may be adapted to detect respiration, and in particular, regional respiration. Such devices may be used at the request of a medical professional, or by anyone who wishes to monitor respiration. A respiration-monitoring device may be adapted for the continuous and accurate monitoring of respiration, including monitoring of respiration in one or more regions. A complete and accurate measurement of several respiratory parameters (described below) may be made using a plurality of stretchable conductive ink traces arranged in a pattern (e.g., a 'zig-zag' pattern) arranged in different region of the garment so that they are positioned about a wearer's torso; alternatively in some variations a conductive elastic strip (e.g., an elastic strip that has been impregnated with a conductive material) may be used in addition to or in place of stretchable conductive ink traces. Regions including lengths of stretchable conductive respiration sensors may include: the anterior part of a shirt, the posterior part (back) of a shirt; each or either of the two lateral sides of a shirt, etc. Sub-regions within these regions may also be used. The stretchable conductive respiration sensors, as described above, may have a resistance that varies slightly with stretch; this property may be used to detect and/or measure body movement as the sensor is stretched while worn on the body.

As described below, in some variations, four or more respiratory signals may be measured to determine localized respiration. For example, twelve signal may be measured by grouping the variable resistances of the traces (or an average of numerous traces) that are placed in the following areas/regions: (1) anterior, upper right (e.g., 6 traces); (2) anterior, upper left (e.g., 6 traces); (3) anterior, lower right (e.g., 5 traces); (4) anterior, lower left (e.g., 5 traces); (5) posterior, upper right (e.g., 6 traces); (6) posterior, upper left (e.g., 6 traces); (7) posterior, lower right (e.g., 5 traces); (8) posterior, lower left (e.g., 5 traces); (9) lateral, upper right (e.g., 3 traces); (10) lateral, lower right (e.g., 5 traces); (11) lateral, upper left (e.g., 3 traces); (12) lateral, lower left (e.g., 5 traces). Based on the arrangement of stretch-sensitive conductive traces and/or elastic strips, parameters may be extracted by analysis of the different signals. For example, a measure of total tidal volume may be determined by adding the signals from all of the stretch sensors in each region (e.g., 1+2+3+4+5+6+7+8+9+10+11+12). A measure of rib cage tidal volume may be determined by adding the signals from the upper regions (e.g., 1+2+5+6+9+11). A measure of abdominal tidal volume may be determined by adding the signals from the lower (abdominal) regions (e.g., 3+4+7+8+10+12). A measure of the rib cage respiratory region may be determined by adding just the region associated with the right rib cage (e.g., 1+5+9); a measure of the left rib cage may be measured by adding just the regions associated with the left rib cage, (e.g., 2+6+11). A measure of the respiration in/at the right abdominal region may be determined by adding the signals from the right abdominal region (e.g., 3+7+10), and similarly a measure of the respiration in/at the left abdominal region may be determined by adding the signals from the left abdominal region (e.g., 4+8+12).

From the time course of the signals (e.g., the signal of the total tidal volume), temporal parameters of breathing, such as respiratory frequency (f), inspiratory time (Ti), expiratory time (Te), and/or duty cycle [Ti/(Ti+Te)] can be determined, recorded, measured and/or displayed (as can any of the signals detected on the garment).

For example, FIGS. 1A-1C illustrate one variation of a shirt for detecting and/or monitoring, including continuous monitoring, respiration. In any of these examples, the apparatus, which may be referred to interchangeably as a device or system, may be configure to continuously and accurately monitor respiration The shirt shown in FIGS. 1A-3A are compression garments (shirts) typically composed by four parts: (a1) 1903 anterior and lateral sides; (a2) 1905 posterior (back); (a3) 1907 right arm; (a4) 1909 left arm. These parts are sewn together after deposition of conductive ink, conductive connector (e.g., Kapton with conductive material and/or wires stitched in a zig-zag pattern) and layers of insulating material, e.g., by a transfer process.

In general, conductive ink traces may be used as sensor. In FIGS. 1A and 1B, the sensor is a plurality of conductive ink traces that are stretchable traces. Conductive ink (including the conductive ink, adhesive and gradient region) may be used to form the conductive traces 1919, as described herein.

Any of these devices may also include a sensor manager unit. The sensor management unit 1921 may be a processor that is placed on the garment (e.g., on the back) in connection with an interface for connecting the sensors to the processor. The processor may be, for example, a smartphone or other handheld device. The apparatus may have a communication unit; this communication unit may be separate or may be integrated with the processor (and/or may include its own dedicated processor). For example, a communication unit may also be placed on the back, and connect to the interface.

Additional sensors may also be used, including motion sensors. For example, a tri-axes accelerometer (alone or, e.g., embedded in the communication system), may be included.

In general, any of these devices may include one or more wearer inputs, such as 'touchpoint sensors'. For example, two capacitive touch points 1933, 1935, placed on the arms, may be used. A touchpoint sensor may include two electrodes (e.g., one on the inner, the other on the outer, surface of the garment in corresponding positions), made of conductive ink patterns, a separating layer of the textile between the two conductive electrode patterns; and an insulating layer deposited onto the internal conductive ink pattern layer. A connecting trace may be included between the external electrode and a terminal point placed close to the neck.

Additional sensors may include one or more electrodes, such as an electrode to detect hear rate. For example, two electrodes 1941, 1943 for heart rate (HR) measurements, made of conductive ink, may be placed on the inner surface of the right and left arms of the shirt. These electrodes may be connected by a conductive connector such as a conductive (Kapton) traces connecting the HR electrodes to the terminal point close to the neck, as shown in FIGS. 1A and 1C.

In general, the respiratory traces may be positioned in any region of the body of the shirt to detect movement (expansion/retraction) due to respiration in that portion of the body. A complete and accurate measurement of several respiratory parameters (see below) may be provided for individual regions of the wearer's body by positioning conductive ink stretchable traces, 'zig-zag' shaped, (e.g., by transfer process) in different regions of the body of the shirt. For example, conductive traces and/or conductive elastic strips may be positioned on the anterior and the two lateral sides of the shirt, on the posterior part (back) of the shirt, and in various sub-regions of these portions.

In FIGS. 1A-1C, eight signals are measured by the sensor manager unit (processor) as voltage variations determined measuring by the variable electrical resistance of the traces placed in parallel in the following areas:

1. Anterior+lateral, upper right (5 traces in parallel).
2. Anterior+lateral, upper left (5 traces in parallel).
3. Anterior+lateral, lower right (5 traces in parallel).
4. Anterior+lateral, lower left (5 traces in parallel).
5. Posterior, upper right (6 traces in parallel).
6. Posterior, upper left (6 traces in parallel).
7. Posterior, lower right (5 traces in parallel).
8. Posterior, lower left (5 traces in parallel).

The vertical traces shown are made of conductive ink and/or conductive elastic strips, and constitute the terminals of the total electrical resistance in these 8 areas. These respiration sensors (respiratory sensors) are connected to terminal points positioned close to the neck (at the interface region). A processor or other circuitry may be used to detect/monitor resistance. For example, in some variations a sensor manager (processor) may be used to obtain and/or store, transmit, analyze, process, etc. the 8 signals listed above. The processor may also incorporate and analyze, transmit, process and/or store additional signals, including the signals obtained by summing one or more combination of single signals. For example, as mentioned above:

Total=1+2+3+4+5+6+7+8
Rib cage signal=1+2+5+6
Abdominal signal=3+4+7+8
Right rib cage signal=1+5
Left rib cage signal=2+6
Right abdomen signal=3+7
Left abdomen signal=4+8

From the time course of the signal of total signal, the following temporal parameters of breathing can be obtained: respiratory frequency (f), inspiratory time (Ti), expiratory time (Te), duty cycle [Ti/(Ti+Te)], etc.

As mentioned above, these signals may be stored, transmitted, analyzed, etc. by the processor and/or communications unit.

FIGS. 1D, 1E and 1F show another compression garment including regional respiratory sensors similar to the garment shown in FIGS. 1A-1C.

As mentioned above, in some variations a respiration/respiratory sensor include a breathing sensor that is a conducive elastic strip that has be treated to have a resistance that varies with stretch, with a relatively small (or negligible) mechanical and very low electrical hysteresis in cyclic loading. Such sensors may be referred to herein as conductive elastic strip sensors, or conductive elastic strain gauges. FIGS. 23 to 38 illustrate the method of making and using one variation of a respiratory sensor configured as a conductive elastic strip. Described herein are conductive elastic materials, and method of making and using them. In particular, described herein are methods of forming conductive elastic materials that may be used as part of a sensor (e.g., stretch or respiratory sensor) on a wearable garment, including in particular wearable stretch (e.g., compression fabric) garments. The conductive elastic materials described herein may be used, for example, in any of the garments including respiration or other contact and/or stretch sensors.

The conductive elastic materials described herein may change resistance as they are stretched, and therefor act as a stretch sensor. Further, these materials may have superior mechanical and electrical properties when compared to other stretchable conductive materials, as they have a very high mechanical and electrical memory. This means that they may be stretched, e.g., to as much as 1.2× (or in some variations: 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 3×, 3.1×, etc.) the original, rest, length and return to the same resting length. The dimension of stretching (length, width, etc.) may be the same. In some variations the material maybe more stretchable in one dimension (e.g., length) than the other (e.g., width). Below this upper limit of stretch (e.g., 1.3× the original length, or in some variations: 1.5×, 1.6×, 1.7×, 1.8×, 1.9×, 2×, 2.1×, 2.2×, 2.3×, 2.4×, 2.5×, 2.6×, 2.7×, 2.8×, 3×, 3.1×, etc.) the material does not exhibit substantial hysteresis, and will return to the original resting length.

Similarly, the material may experience little, if any electrical hysteresis with stretch below a relatively high limit of stretch. For example, the material may have approximately the same conductance/resistance after being stretched up to 1.2× (or in some variations: 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 3×, 3.1×, etc.) their original, rest, length. Further, the change in resistance with stretch may linear over at least a portion of the range. Thus, the materials described herein exhibit very little electrical hysteresis with use. Further, these properties may be repeatable for a long period of time (e.g., over many hundreds, thousands or hundreds of thousands or cycles of stretch.

Finally, the response time in recovering from stretch may be extremely fast. For example, the material may return to the initial performance measurements (for length and resistance) within a less than 5 seconds (e.g., less than 4 seconds, less than 3 seconds, less than 2 second, less than 1 second, etc.). Thus, the electric return time is faster than 5 seconds over the entire stretch range (of less than the maximum stretch length, e.g., 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 3×, 3.1× the original length).

These properties, and particularly the electrical properties, of the material appear to result from a reduced molecular damage of the conductive material during even repeated stretch cycling. This may result in an increase in the length of the lifetime of the material. Further, the elastic properties (the return from stretch) appear to be drive by the core elastic material to which the conductive material (e.g., conductive coating) is coated. The core material appears to keep is elastic properties even when coated with a relatively thick coating of (dried) conductor.

Figure 23:
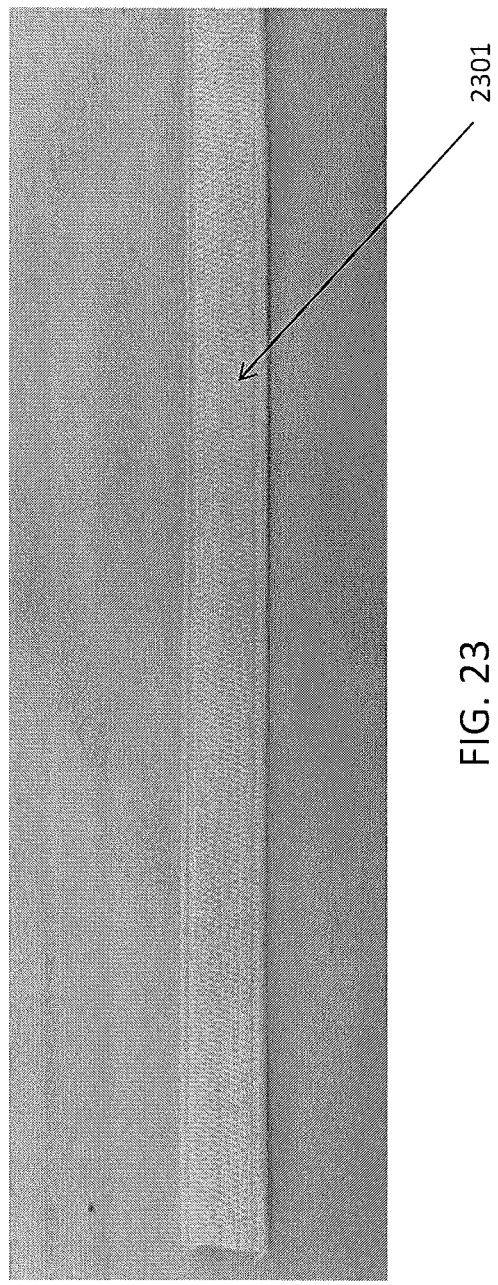
FIG. 23 shows one component of the conductive elastic strip or ribbon material that may be fabricated as a sensor and/or electric trace as described herein.

FIGS. 23-38 illustrate one method of making a conductive elastic material. In brief, as shown in reference to the figures, an elastic material, and particularly an elastic waistband type material may be coated as described herein. FIG. 23 shows one example of an elastic material. In general, the elastic material may (such as an elastic waistband) be formed form either a knitted or woven flat elastic material. The knitted elastic may be covered by fabric. The material forming the elastic and/or covering may be natural (e.g., cotton, wool, etc.) or synthetic (e.g., polyester) or any combination thereof. For example an elastic material such as the material shown in FIG. 23 may be formed of a porous/absorbing material such as cotton and may include additional (e.g. polymeric) material woven or stitched into the covering material.

The elastic material may, at the start, be a strip or band that is relatively narrow and thin. For example, the width of the band may be between about 0.1 and 3 cm (with a preferred thickness of about 1.5 cm). The material may include multiple sets of warp yarn (e.g., elastic yarn) that is woven onto or into a fabric.

Figure 24:
FIGS. 24, 25, 26 and 27 illustrate one method of making a conductive elastic ribbon as described herein.
Figure 25:
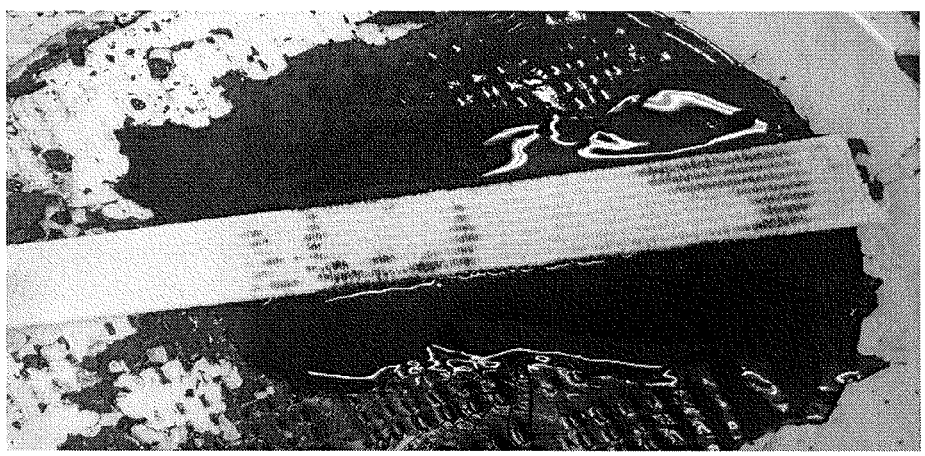
Figure 26:
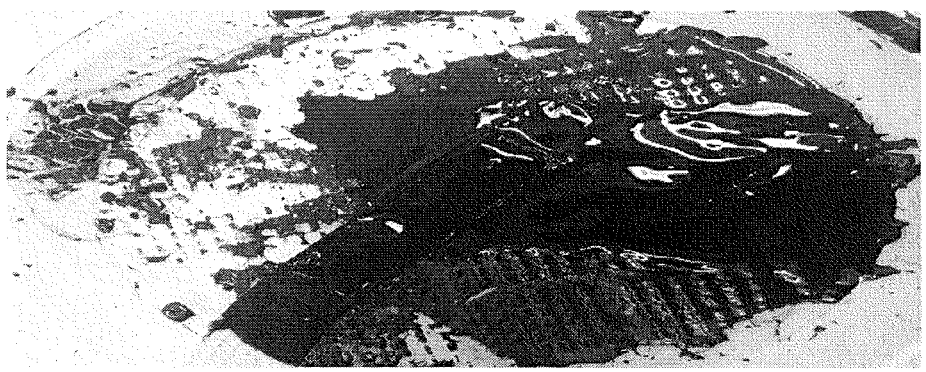

In general, the conductive elastic material is made by first coating (e.g., dipping, spraying, submerging, etc.) an elastic material, and particularly an absorbent or partially absorbent elastic material, into a suspension of electrically conductive particles in a solution. Any appropriate conductive material may be used, including, but not limited to carbon black (as shown in FIGS. 24-26), metallic conductive materials (e.g., gold, silver, silver/silver chloride, graphene, mica coated with oxide, etc.). The conductive material may be a mixture of conductive particles suspended in a solution (such as water or alcohol solutions). The solution may include a base or binder as well as the solution of conductive particles. For example, the solution may be between 0.1-25% binder (e.g., acrylic, water based polyurethane, etc.) and 99.9%-75% solution of conductive particles.

Figure 27:
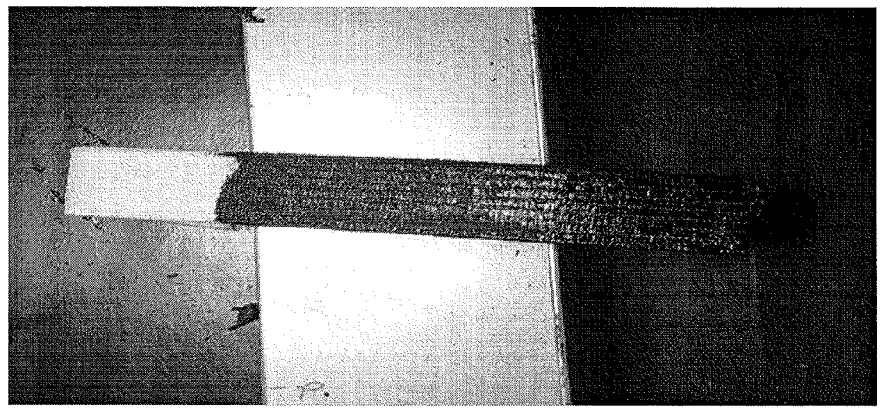
Figure 28:
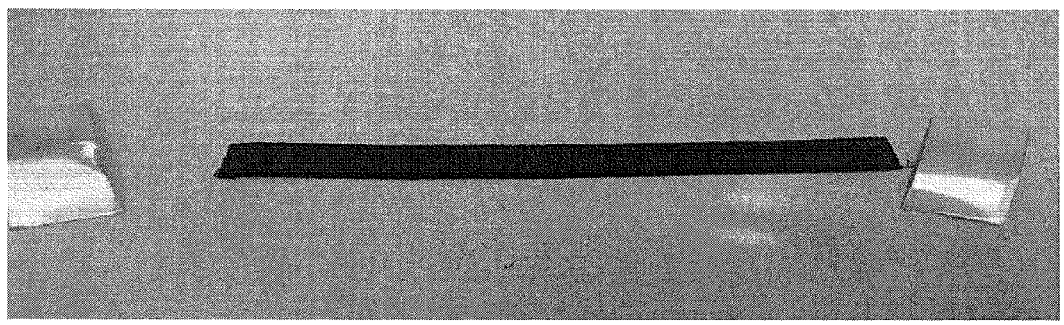
FIGS. 28, 29 and 30 illustrate attachment of conductive terminals at the ends of the conductive elastic material formed as described above.
Figure 29:
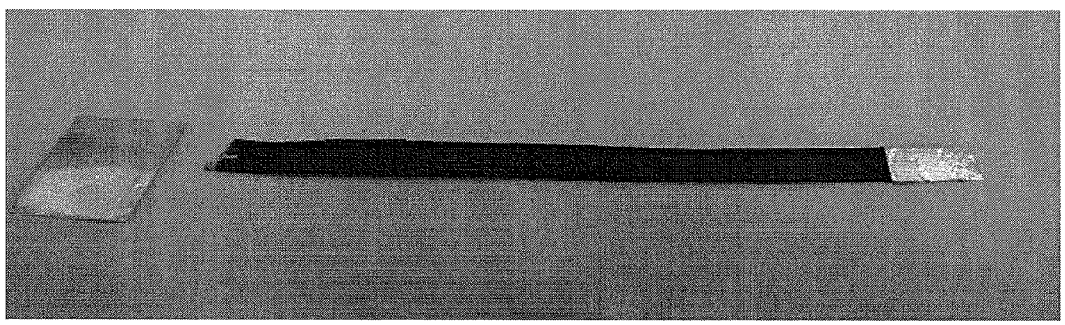

For example, in FIG. 24, a solution of carbon black suspended in water is poured into a plastic container. As shown in FIG. 25, the initially uncoated elastic material is then coated by dipping both side of the elastic ribbon into the solution and moving it from side to side (left to right) in the solution. In FIG. 26 a uniform coverage of the entire ribbon surface is obtained, as shown. The coated ribbon may then be dried, as illustrated in FIG. 27. For example, the ribbon may be dried by applying heat, and/or air (or vacuum). In FIG. 27, the coated ribbon is dried in a convection oven for 30 minutes.

Figure 30:
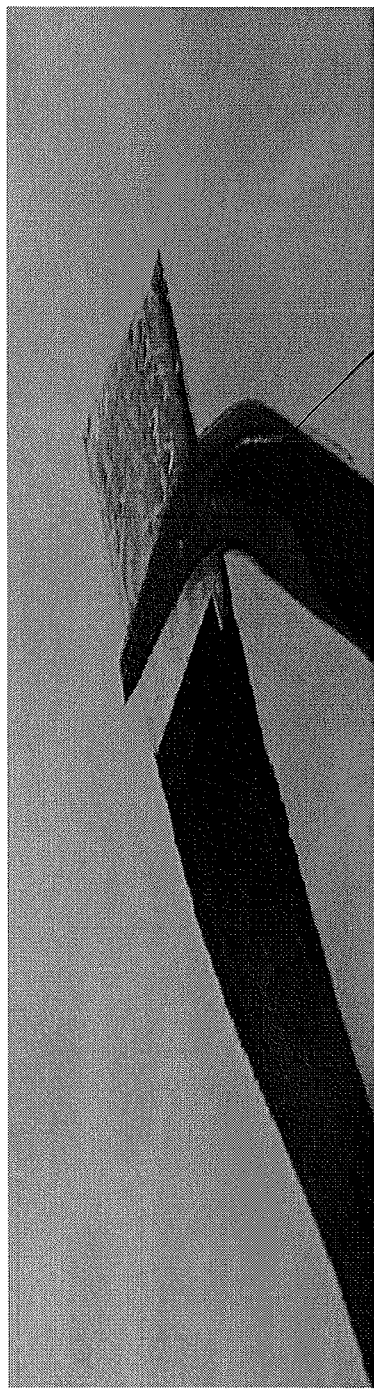

Once dried, this core elastic material may be connected to conductive ends and/or added to an outer material (typically formed of the same material onto which it will be applied) for attachment to a garment. For example, in FIG. 28, a pair of terminals (shown s copper terminals, though any conductive terminal may be used) are attached, also shown in FIGS. 29 and 30. For example, in FIG. 29, copper terminals are formed by cutting the copper material (e.g., into rectangles at length of about 20 mm) and wrapping the terminal material (which is not typically elastic) around the conductive elastic at the edge of the ribbon. The conductive terminal material (e.g. copper) may be elastic or may have an elastic applied (a conductive elastic material) to secure it to the conductive elastic ribbon, as shown. In FIG. 30, a tool 3001 (e.g., pliers) is used to confirm that the conductive terminal is attached to the adhesive and therefore the conductive elastic.

Figure 31:
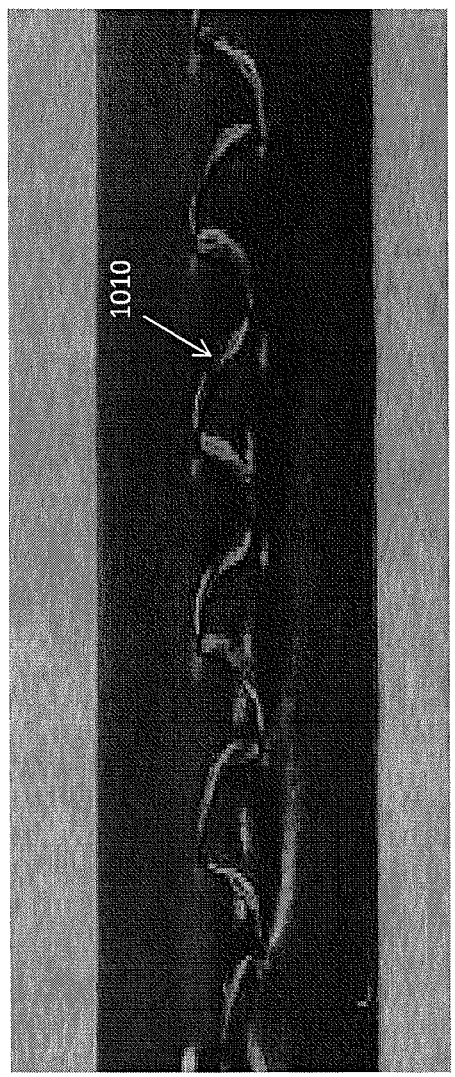
FIG. 31 illustrates one example of a wired ribbon that may be used to connect a stretchable fabric.

Once the terminals are attached, the elastic material maybe coupled to a wire connector, such as the pre-prepared wire ribbon material shown in FIG. 31. In FIG. 31, a wire ribbon material is sewn into a strip of fabric with a pair of twisted wires 1010 (though more than two wires may be used), shown as twisted, enameled (insulated) wires. The wires are sewn into the strip of fabric (e.g., compression fabric) in a zig-zag pattern and the fabric strip may include a fabric adhesive or may be configured for thermally applying to another fabric (e.g., garment), so that the conductive connectors can be applied directly to the fabric without having to sew directly onto the fabric, and providing a covering for the wires. The fabric onto which the wires are sewn is typically the same material to which they are to be applied (e.g., a compression garment fabric). In some variations one side of the fabric onto which the zig-zag pattern of insulated wires is sewn, which may be referred to as an applicator fabric, include or is treated for use with a fabric adhesive (including thermally active adhesive). In practice, long lengths of wire may be prepared ahead of time and cut to need for application to a garment. Note that in general, a wire ribbon material may be used as an electrical connector connecting one or more sensors to other portions of the garments described herein, including a data module, and/or an SMS component. This wire ribbon material may be referred to herein as a wire ribbon material or as a stitched zig-zag connector. This material may be advantageously prepared in long lengths and cut to the desired length for securing (e.g., adhesively securing) the garment and/or sensor.

Figure 32:
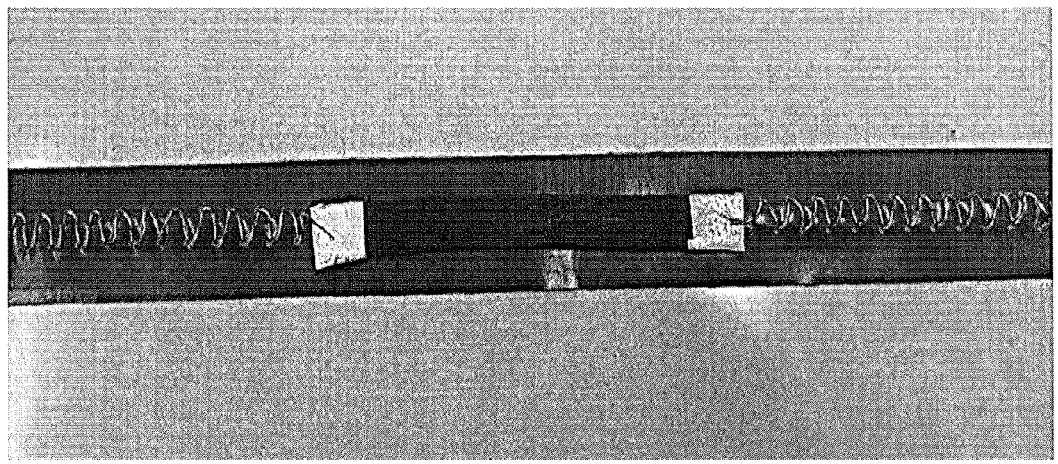
FIG. 32 illustrates the attachment of a conductive elastic ribbon formed as shown in FIGS. 24-30 above, to a ribbon pre-formed to include an attached wire such as shown in FIG. 32.
Figure 33:
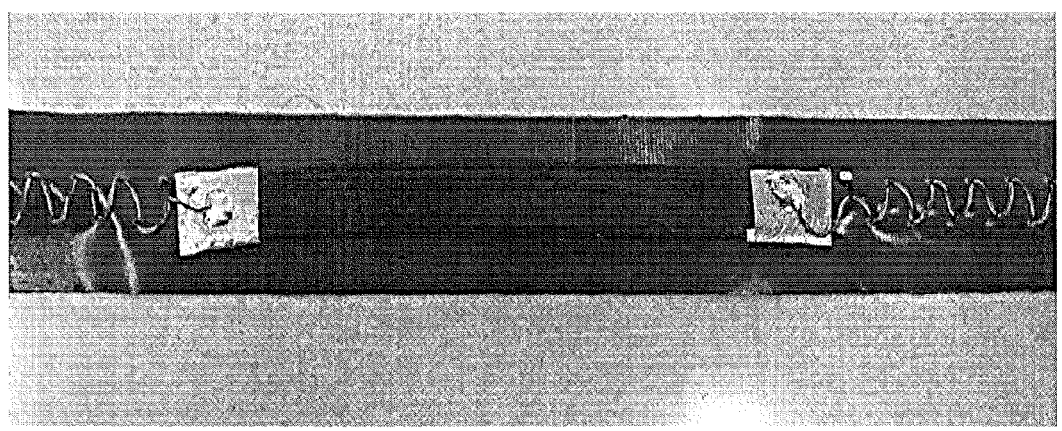
FIGS. 33 and 34 illustrate the formation of a sealed conductive ribbon.

For example, in FIG. 32, the conductive elastic ribbon is place on a thermo adhesive glued surface of the wired ribbon in a region that does not include wire, and connected to the conductive wire ends. For example, as shown in FIG. 33, the conductors (wires) are soldered to the copper terminals.

Figure 34:
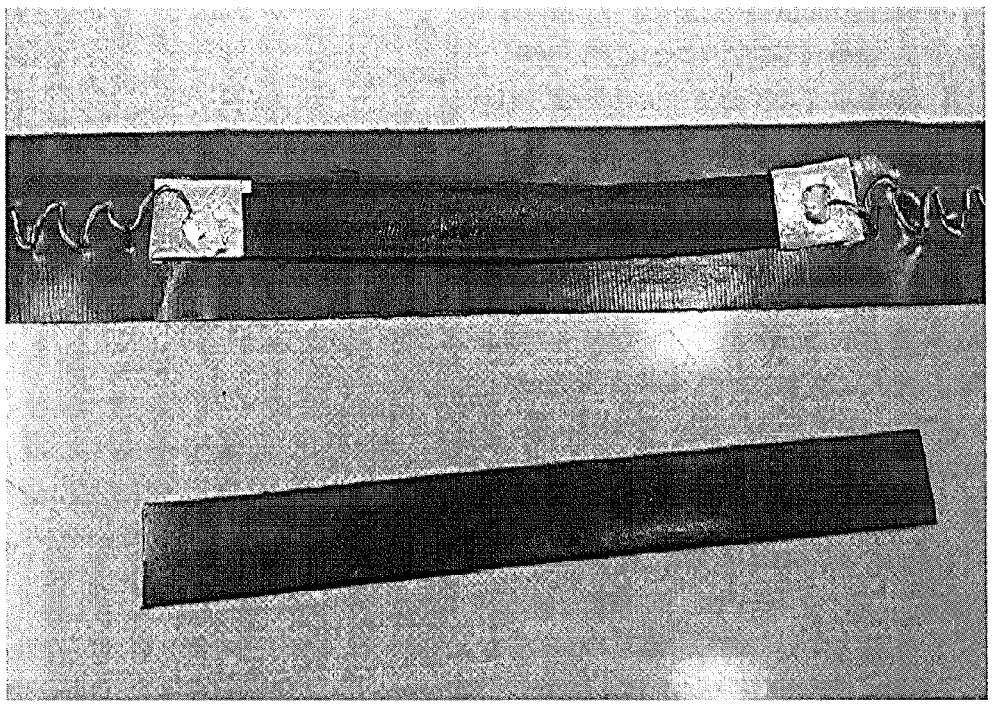
Figure 35:
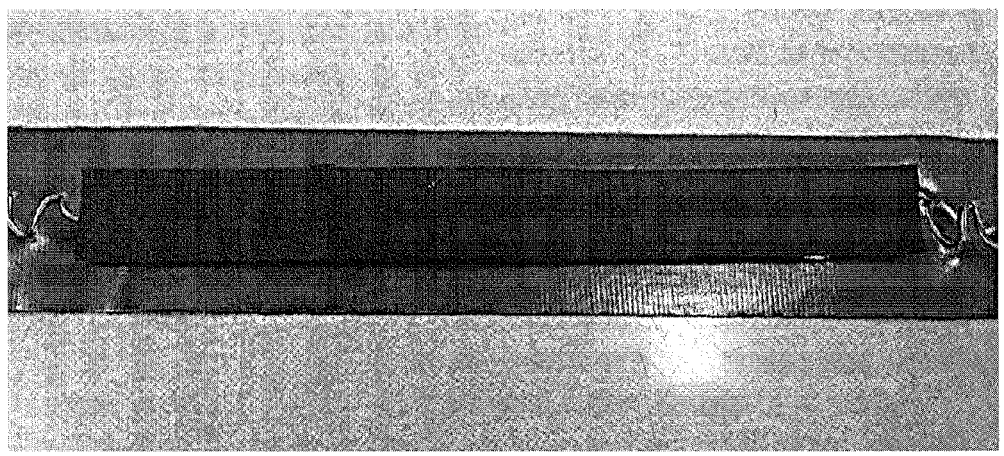
FIGS. 35 and 36 illustrate the attachment of the sealed conductive ribbon, including the electrically conductive elastic material, into a fabric such as a stretch fabric to form a garment (e.g., a respiration sensor/stretch sensor of a garment).

Once applied to the conductive wires, the elastic ribbon may be enclosed within a fabric (e.g., an insulating fabric, which may be the same as the fabric to which it's being applied). In some variations the elastic ribbon may be enclosed in an insulator material and/or coated with an insulator. In FIGS. 34 and 35 the external side of the conductive elastic ribbon (including the contacts) is sealed with an adhesive tissue ribbon to a width of approximately 33 mm). The tissue (covering) ribbon may be fixed over the elastic ribbon by, e.g., thermo press (when using a thermally activated adhesive) as shown in FIG. 35.

Figure 36:
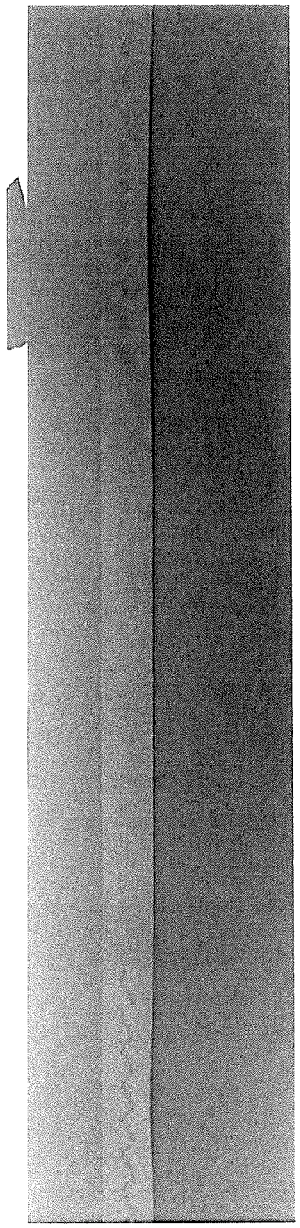
Figure 37:
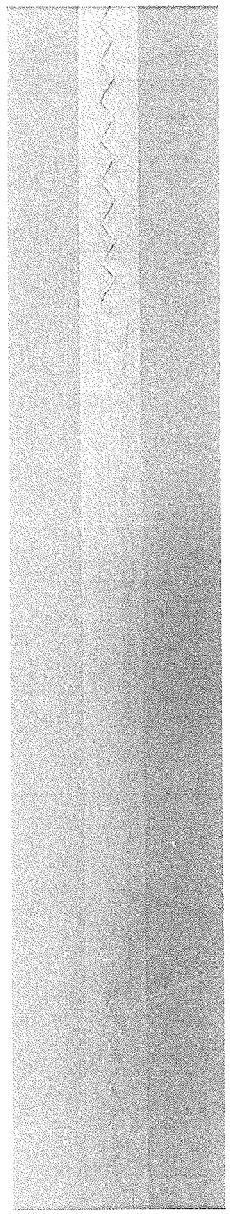
FIGS. 37 and 38 show one example of a final version of the conductive elastic material fixed into the garment.
Figure 38:
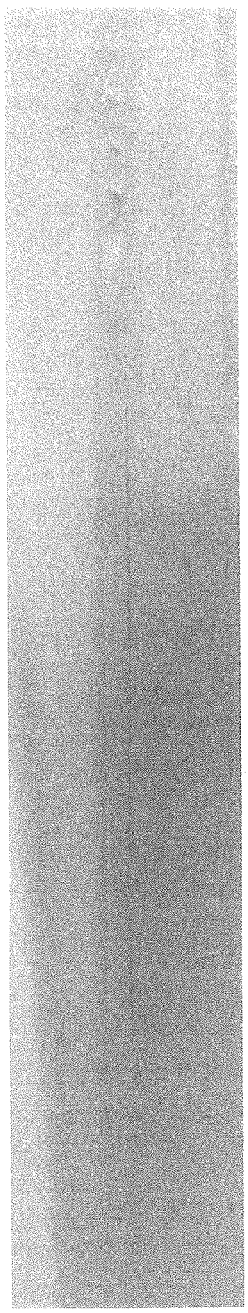

Thereafter, the resulting ribbon including the conductive elastic material and zig-zag wires may be attached to a garment, such as a zig-zag garment. For example, FIG. 36 shows a variation in which the resulting assembly of the conductive elastic is fixed to a garment to provide a breath (respiration) sensor. The assembly may be attached by thermo press (e.g., again using a thermally activated fabric adhesive, as shown in FIG. 36. The final result, in example, is shown in FIGS. 37 and 38. FIG. 37 shows a view of an internal side of the garment (the assembly may be attached in the internal side of the compression garment, as shown, or an external side). FIG. 38 shows an eternal view of the same garment. In FIGS. 37 and 38, the garment is configured as a respiration-sensing shirt (e.g., T-shirt).

Thus, the conductive elastics strips described above may be used as part of a compression garment. Described above are method of making and using conductive elastic material having very low mechanical and electrical hysteresis and may therefore be used as respiration sensors for wearable compression garments. This conductive elastic material may be used as a respiration/respiratory sensor, or as part of a connector. A respiratory sensor using a conductive elastic material may be formed of a strip of elastic material that has been impregnated with a solution of conductive particles (e.g., carbon black) and dried (or at least partially dried); conductive connectors may be attached to the ends of the strip of impregnated elastic material. In some variations the connector may be electrically connected to a wire ribbon material formed of enameled (e.g., insulated) metallic conductive wires that are stitched in a zig-zag pattern on a strip of fabric, such as compression fabric. The conductive-particle impregnated elastic material and/or the wire ribbon connector material may be enclosed within a fabric material (such as a compression fabric material). This enclosed sensor and connecting length(s) of wire ribbon may then be attached to a garment as described above (e.g., see FIGS. 1A-1F).

For example, FIGS. 44A-44B illustrate one variation of a garment configured to measure respiration using a plurality of conducive-particle impregnated elastic strip that is configured as a strain gauge. In FIG. 44A the garment is shown without sleeves, though sleeves may be included. The garment body may be made of a compression garment material, to which the strain gauge sensors are attached as shown. The respiration sensors are configured as strain gauges having an elongate length of elastic material that has been impregnated with a conductive material (e.g., a carbon black solution with a base/binding material, as described above). The impregnated and/or coated elastic material strip may then have conductive metal ends attached to the end regions and may be enclosed in a material, e.g., the same or a similar compression garment fabric material that the body of the garment is made of. In FIG. 44A, the six pairs of horizontally arranged respiration sensors 4403 formed of conductive elastic members are arranged at different heights along the torso region (e.g., near the Louis angle, 3rd costal interspace, xyphoid, lower costal margin, above the umbilicus, and below the umbilicus). A stitched zig-zag connector 4407 (formed from a separate strip of compression fabric onto which a wire, such as enameled copper wire, is sewn in a sinusoidal pattern, then applied to the body of the garment) is used to connect the twelve sensors to an SMS unit, as shown in FIG. 44B, showing the back of the garment of FIG. 44A. Each sensor may be connected at both ends to a different wire in the stitched zig-zag connector so that the change in electrical property of the conductive elastic strip maybe detected by the SMS. The garment may also include additional sensors. In FIG. 44A, a pair of ECG electrodes 4409, 4409' are shown, an each connected to the SMS via the stitched zig-zag connector(s) 4407.

These garments may be manufactured as shown in FIG. 45, showing three pieces of fabric forming the body of garment (e.g., a central back portion 4419, a right panel 4421 and a left panel 4423; because the respiration sensors are continuous on the right side and left side, the right and left panels may be stitched to the back first, before the sensors are applied (arrow 4431). As discussed above, these different respiration sensors may correspond to different zones that may be separately examined.

Electrocardiogram (ECG) Measuring Garments

Also described herein are garments that may be used to effectively and continuously monitor electrocardiogram (ECG) signals. For example, a garment may be adapted to measure signals by including pairs of redundant traces between which the apparatus (e.g., garment, control/sensing module, etc.) may switch. In some variations the SMS and/or a sensor module may determine which set of electrodes between the redundant multiple electrodes to use in detecting a particular lead for an ECG. FIGS. 2A-2B, 3A-3B, and 4A-4B illustrate garments configured to measure ECGs. Each of these garments includes redundant leads (two or more) where each of the redundant leads can detect a signal from an electrode that may be used to determine an ECG signal for that lead.

The electrodes used to detect ECG signals may be formed of the stretchable conductive ink described herein. In some variations, the electrodes are printed, applied or formed on one side of the garment (e.g., the inner surface) and adapted to be in continuous contact with the subject's skin so as to measure ECG signals. Electrodes may be connected via conductive traces (formed by, for example, stretchable conductive ink and/or combinations of stretchable conductive ink and substrates such as Kapton with higher-conductance traces) to an SMS and/or sensor module. The SMS and/or sensor module may determine, e.g., based on the quality of the signal, which of the redundant traces to use/present for the ECG signal.

For example, in FIGS. 3A-4B, the electrodes 2103 are formed as a series of electrodes constituted by ink circles positioned in the standard points of the 12-lead EKG. On a garment (to be worn on the torso), the electrodes may be placed so that when the garment is worn the redundant (pairs) of chest electrodes are positioned corresponding to the V1-V6 positions:

TABLE 1

| position of chest electrodes | |
|---|---|
| Electrode | Placement |
| V1 | 4th Intercostal space to the right of the sternum |
| V2 | 4th Intercostal space to the left of the sternum |
| V3 | Midway between V2 and V4 |
| V4 | 5th Intercostal space at the midclavicular line |
| V5 | Anterior axillary line at the same level as V4 |
| V6 | Midaxillary line at the same level as V4 and V5 |

Similarly leads may be placed at other locations on the shirt to measure the RL, RA, LL and LA leads (limb leads), corresponding to:

TABLE 2

| Limb lead positions | |
|---|---|
| Electrode | Placement |
| RL | Anywhere above the ankle and below the torso |
| RA | Anywhere between the shoulder and the elbow |
| LL | Anywhere above the ankle and below the torso |
| LA | Anywhere between the shoulder and the elbow |

FIGS. 3A-3B show the limb leads for the legs positioned at the lower edge of the torso garment, which may be used even not wearing a separate pant. The limb leads in the garments shown in FIGS. 3A-3B and 4A-4B do not include redundant electrodes, however they may.

In any of the ECG-sensing garments, the electrodes may be held against the body for consistent/constant measurement (even during motion) by the structure of the garment, including by an additional harness region 2144 (e.g., yolk region), as shown by the shaded region in FIGS. 3A and 4A. This harness may be formed as a region supporting the ECG chest electrodes that is relatively more supportive (e.g., applying pressure/force) to hold the chest electrodes on/against the body, even during respiration and other body movements. For example, the harness region may be formed as an elastic corset (e.g., width: 2 cm on the sternum, 4 cm on the xiphoid line) running along the sternal line, then separating on the right and left sides of the xiphoid line, then on the back, then converging on the spinal cord and running up to the neck, then again separating into right and left sides around the neck, to finally converging on the sternal line. The material of the corset has to be extremely extensible.

The electrodes, and/or the region peripheral to the (e.g., chest) electrodes may include a silicone surface that helps hold the electrode(s) against the chest, and may also prevent the electrodes from slipping. For example, silicone may be located in an inner surface of the shirt, corresponding to the harness/corset position, along the horizontal line on both sides up to 5 cm beyond the midaxillary lines. This silicone may help ensure that the ink electrodes are fixed to the chosen position and do not move with patient's motion.

As mentioned, it is particularly helpful that the electrode include adjacent redundant electrodes. All of the electrodes (including the redundant electrodes) may be connected to the SMS and/or control module to detect ECG signals and the SMS and/or control module may decide which of the redundant signals to use (or in some variations to use the redundant signals to improve the overall signal quality, e.g., by selective filtering, averaging, or the like). In some variations the non-selected redundant signal may be ignored; in other variations the apparatus may be configured to store it for later analysis. Both pairs (or more than 2) of electrodes may have signals that may be stored, transmitted and/or processed; decisions about which of the redundant electrodes to use to generate an ECG may be made later.

Sleep Monitoring Garment

Also described are garments configured to be worn to monitor a subject's sleep. Sleep monitoring may generally be used to measure sleep motion, respiration during sleep, body temperature (both core and regional), eye motion, and the like. Such indicators may be used to determine the sleep stage, sleep quality, sleep duration, etc. Any of the garments described herein may be adapted to determine sleep indicators and may therefore be worn while sleeping. Thus, these garments may be comfortable and adapted for use by a sleeping person.

Figures 7A, 7B:
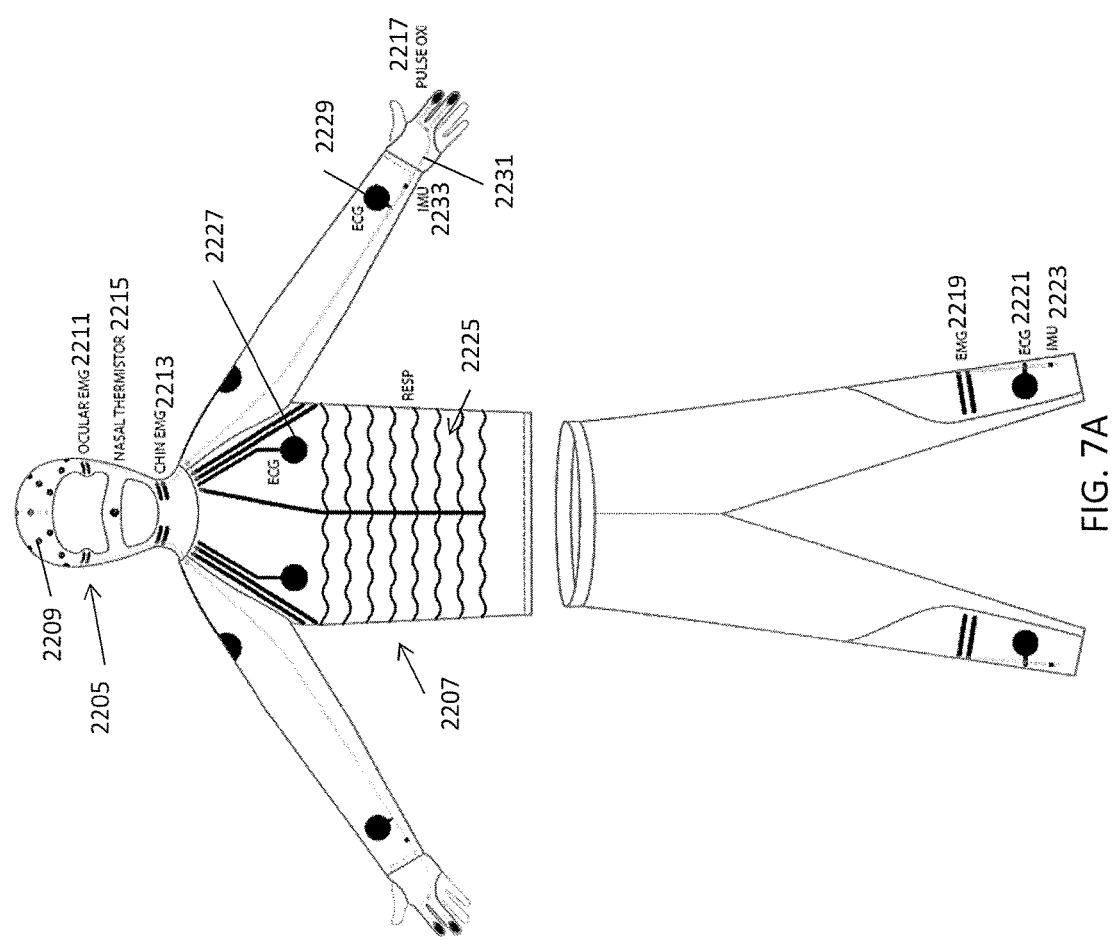
FIGS. 7A, 7B and 7C show front, side and back views, respectively of a garment configured to be worn during sleep to monitor a subject's sleep.

For example, in FIG. 7A, the front of the garment is shown, including a head cap/hood 2205 with sensors 2209 arranged to determine EEG (scalp electrodes on the inner surface of the hood), facial/ocular EMG (to detect eye movement), a nasal thermistor (detecting respiration) and chin EMG (detecting jaw motion, etc.). The hood may be integral with the shirt 2207 or it may be separately attached thereto. In any of the garments the various components (e.g., shirt, hood, gloves, pants, etc.) may be optional; individual garments or groups of garments may be used. The shirt may be similar or identical to the respiration and/or ECG sensing garments described above. In FIGS. 7A and 7B, the torso region includes regional respiration sensors 2225 (stretchable conductive traces) for the anterior and lateral regions of the body, as well as EGC electrodes 2227 (though not all of the V1-V6 lead electrodes are included). The garment may also include pants including limb leads 2229 (for ECG detection) and/or EMG sensors 2219 to detect leg movement/twitch. Full or partial gloves 2231 may also be included and may measure blood oxygenation 2217 (e.g., pulse oxygenation) at the extremities (e.g., fingers).

Figure 7C:
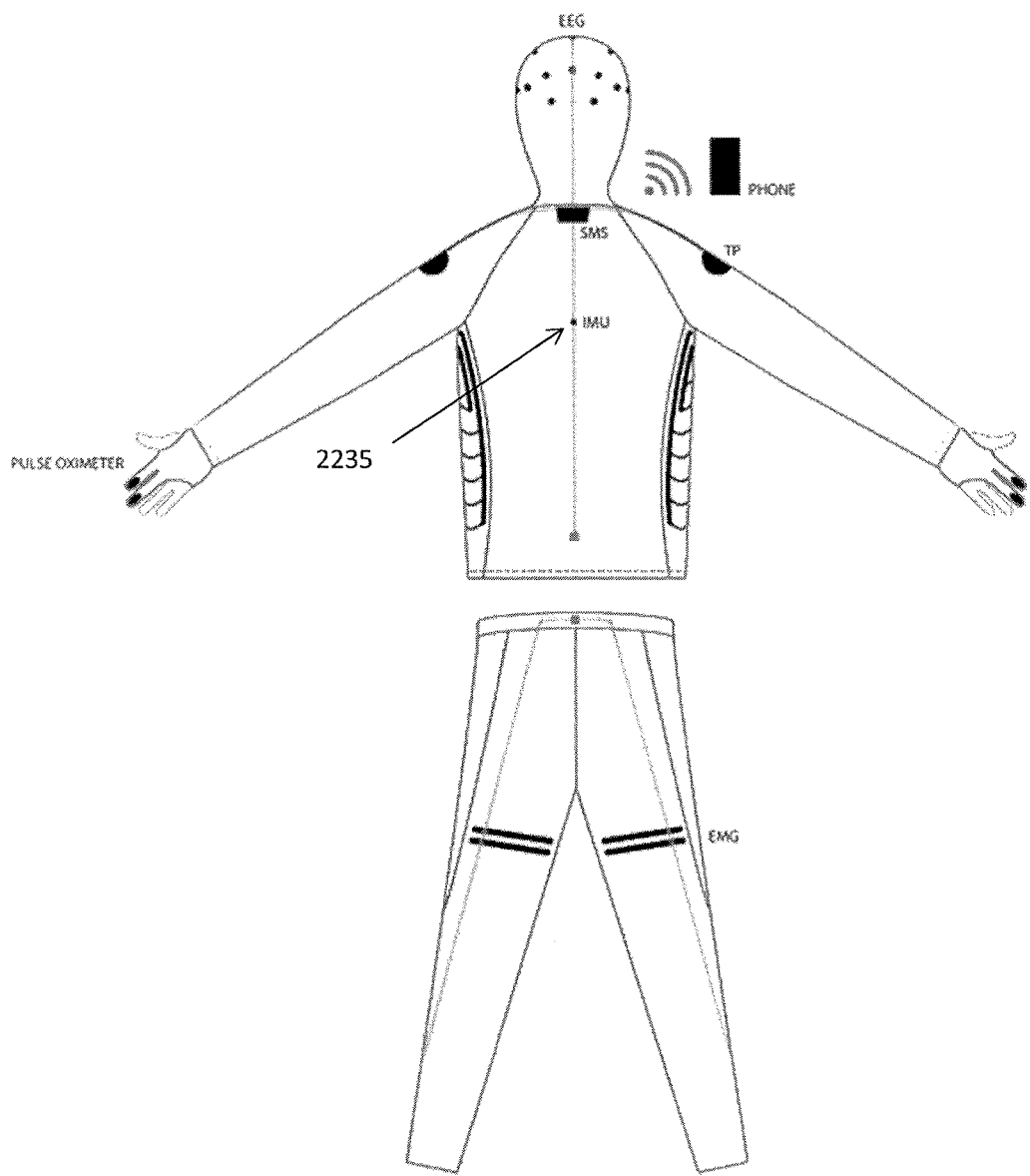

FIGS. 7A-7C illustrate one variation of a garment that may be formed as described herein and may include a plurality of sensors for determining sleep parameters. For example, in FIG. 7A, the front of the garment is shown, including a head cap/hood 2205 with sensors 2209 arranged to determine EEG (scalp electrodes on the inner surface of the hood), facial/ocular EMG (to detect eye movement), a nasal thermistor (detecting respiration) and chin EMG (detecting jaw motion, etc.). The hood may be integral with the shirt 2207 or it may be separately attached thereto. In any of the garments the various components (e.g., shirt, hood, gloves, pants, etc.) may be optional; individual garments or groups of garments may be used. The shirt may be similar or identical to the respiration and/or ECG sensing garments described above. In FIGS. 7A and 7B, the torso region includes regional respiration sensors 2225 (stretchable conductive traces) for the anterior and lateral regions of the body, as well as EGC electrodes 2227 (though not all of the V1-V6 lead electrodes are included). The garment may also include pants including limb leads 2229 (for ECG detection) and/or EMG sensors 2219 to detect leg movement/twitch. Full or partial gloves 2231 may also be included and may measure blood oxygenation 2217 (e.g., pulse oxygenation) at the extremities (e.g., fingers). Additional embodiments of garments that can be used for sleep monitoring are illustrated in FIGS. 13A-21B.

The SMS and/or sensor module may be adapted to process and/or analyze the sensor inputs and to provide a report on the sleep status (or status over time) for the individual wearing the garment.

In general, these devices may be useful for a sleep lab or home sleep lab. They can record all of the signals usually included in polysomnogrpahic analysis, including respiration, e.g., in a simplified way; only on the anterior and lateral part of the shirt; rib cage and abdominal part, 4 quadrants, may be needed to know when you have paradoxical motion. It is helpful that you have both upper and lower, but may also help to have right/left as well. The use of ECG in the upper part of the torso with a simplified (e.g., 2 electrodes and the wrists and legs) configuration is also helpful. The garment's sensors may again include redundancy as discussed above to have the best and most reliable ECG. In particular, heart rate is used, which may not require a full ECG. EMG recordings (electromyographic electrodes) may be formed of the stretchable conductive ink and may be located in different positions. For example, on the chin, the lower (muscle), which may be helpful for use in polysomnogrphic MG. In addition, ocular EMG may be helpful for detection of REM and other sleep stages. As mentioned a themister (temperature sensor at the level of the nose) may be used to detect airflow through the nose, similar to what is done with sleep lab. IMUs (inertial measurement units) may be used on the arms and legs to detect limb motion. Also, an IMU2235 may be located on the back of the garment, which is useful for detecting the patient's position (rolling over, supine, prone, on side, etc.), and may detect restlessness.

Garment Support Structures and Accessories

Any of the garments described herein may include additional support structures to help secure the sensor(s) against the body. Such support structures may be expandable, and may improve the contact between the physiological monitoring garments disclosed herein and the skin of the wearer. For example, the chest anatomy can prevent a sensor on the physiological monitoring garment from making good electrical contact with the chest of the patient as described herein. A support garment, which may be generally referred to as a harness, can be worn over the physiological monitoring garment to provide pressure to improve electrical contact between the electrodes on the garment and the chest of the wearer. These harnesses (support garments) may be particularly useful with male wearers having large pectoral muscles and female wearers having large breasts. The support garment can include a strap or tie, and may be sized to hold (and apply force to keep) a portion of the physiological monitoring garment (e.g. sensors/electrodes) against the body of the user. Also described are structures that are integrated with these devices to apply force to keep the sensor(s) on the garment pressed firmly against the subject. Such integrated device may be referred to as integrated support structures. In some embodiments the support structure is a self-expanding structure. In particular, integrated support structures may be expandable, including inflatable, elements. Examples of support garments and portions of support garments are shown in FIGS. 14-18.

A support garment (e.g., harness) can be separate from the compression garments described herein, or they may be completely or partially integrated into the garment. A support garment and/or integrated support structure (expandable support structure) can be sized and shaped to fit the anatomy of the user. For example, the support garment and/or support structure can be designed to fit with the chest anatomy of the wearer. The support garment can be sized and shaped based on the gender of the wearer. For female wearer's a support harness can be designed to hold the support structure between the breasts of the patient. Examples of combinations of support harnesses and support structures that can be used for the support garment are illustrated in FIGS. 14A-14D and 15A-15C. For male garment wearers a support strap can be used instead of a harness. Examples of male support straps and support structures are illustrated in FIGS. 16A-16C and 17A-17C.

FIGS. 14A-14B illustrate a support garment 1405 from FIGS. 14C-14D worn over the physiological monitoring garments 1401 illustrated in FIGS. 13A-13B. An additional support structure (integrated into either the monitoring garment 1401 or the support harness 1405 in this example) may also be used. In this example, the support garment is shaped as a harness or sports bra-type configuration to hold the second support structure 1403 securely against the chest and sternum of the wearer. FIGS. 15A-15B illustrates expandable (e.g., inflatable, including self-inflating) support structures that can be used for female wearers. The support structures are shown in FIGS. 15A-15B in a front view and side views in non-inflated and inflated configurations. FIG. 15C illustrates the support structure of FIG. 15A engaged with a female chest. The illustrated support structures are inflatable and shaped to engage with a female chest to securely hold sensors on a smart garment against the chest of the wearer.

Figure 17A:
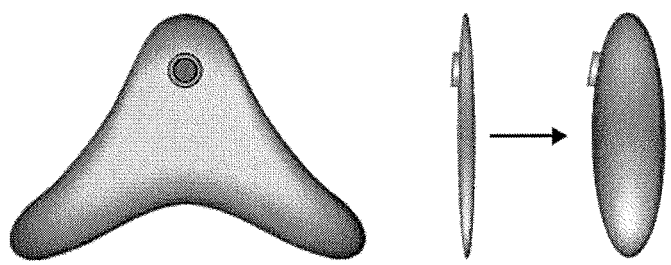
FIGS. 17A and 17B illustrate an inflatable support device in accordance with some embodiments.
Figure 17B:
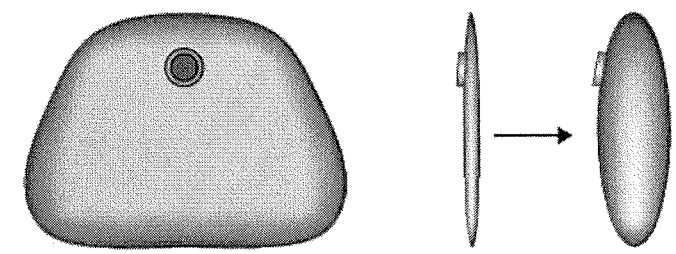
Figure 17C:
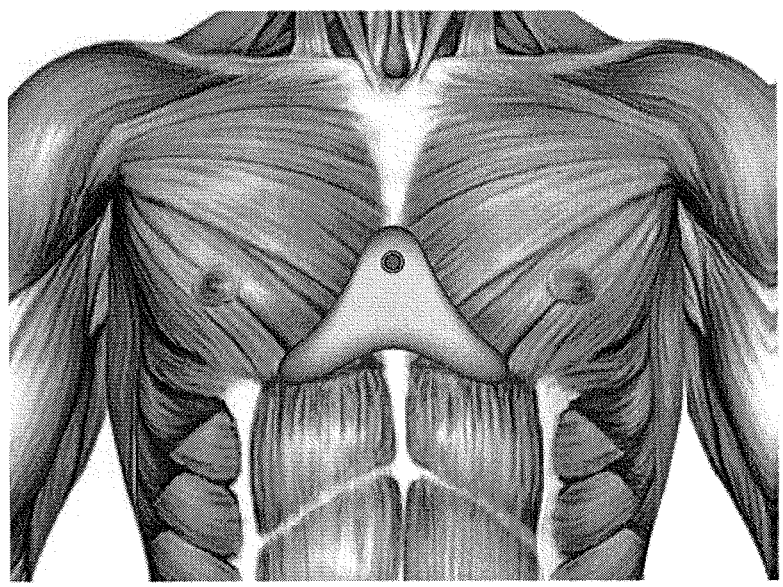
FIG. 17C illustrates the inflatable support device relative to a male chest.

FIGS. 18A-18B illustrate the support garment from FIGS. 16A-16B worn over the physiological monitoring garments illustrated in FIGS. 13A-13B. FIG. 16A-16B illustrate the support strap 1601 having an optional rigid material in the front and an adjustable back material that can be made out of a stretchable material and can include Velcro. FIGS. 17A-17B illustrates support structures that can be used for female wearers. The expandable support structures are shown in FIGS. 17A-17B in a front view and side views in non-inflated and inflated configurations. FIG. 17C illustrates the support structure of FIG. 17A engaged with a male chest.

The support structures shown in FIGS. 17A-17B and 15A-15B provide inward force to compress the sensors on the physiological monitoring garment against the chest of the body to improve the electrical contact between sensors and the chest. In some embodiments the support structure can be expandable (including, but not limited to inflatable) to provide the desired structure to contact the monitoring garment. The support structure can be self-inflating in some embodiments. A self-inflating material can be used within the support structure such that the support structure automatically inflates when activated. In some cases the self-inflating material can be done via a foam material within the support structure, and/or via a chemical reaction. In some cases the chemical reaction can produce a gas or other material that can expand the support structure to conform to the chest anatomy of the patient. In some variations the support structure is a local pad or compressible material that can be held in place by the compression garment and/or the support harness.

In some embodiments the pressure applied by the support structure can be selected by the user.

In some embodiments the support garment and support structure can include sensors and a control system to provide the desired pressure level to the physiological monitoring garment.

The support garment, e.g. harness, strap, bra, etc., can include Velcro, adjustable straps, and other adjustable parameters so that the wearer can tighten the harness such that it provides the desired fit and support to improve the electrical contact of the chest sensors/electrodes.

In some embodiments the support garment and support structure can communicate electronically with the physiological monitoring garment and/or an external computing device.

The support garment can be used with any of the physiological monitoring garments disclosed herein. In some embodiments the support garment is used with a compression shirt and pants having the wiring illustrated in FIGS. 20-21.

Figure 18C:
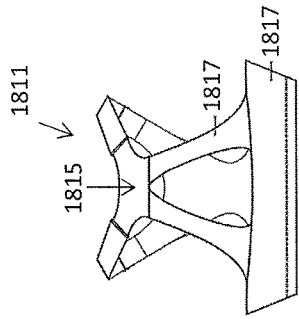
FIGS. 18C-18E illustrate one system including a garment for measuring physiological parameters (e.g., ECG), including a wearable support harness and a support structure for holding the electrodes in the garment against the skin.
Figure 18D:
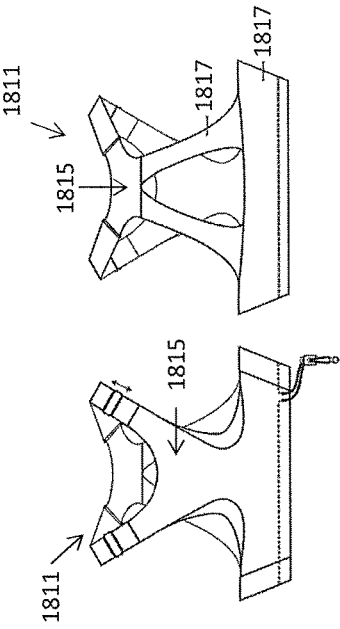
Figure 18E:
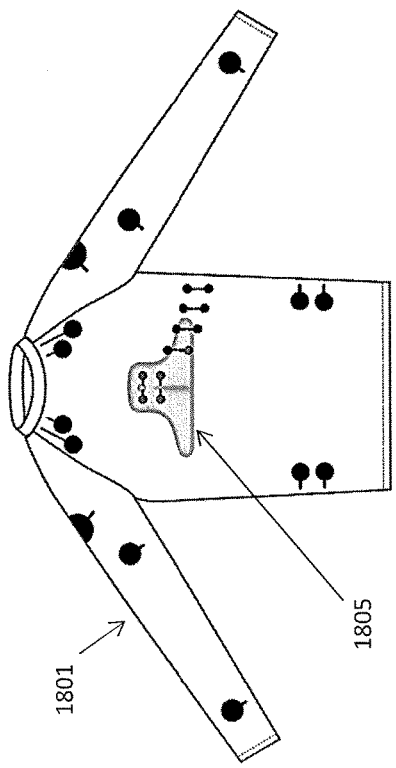
Figure 18F:
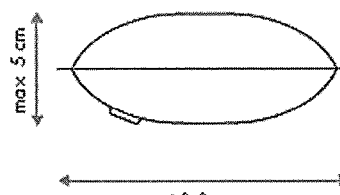
FIGS. 18F and 18G show front and side views, respectively, of the support structure (expandable support structure) of FIG. 18A.
Figure 18G:
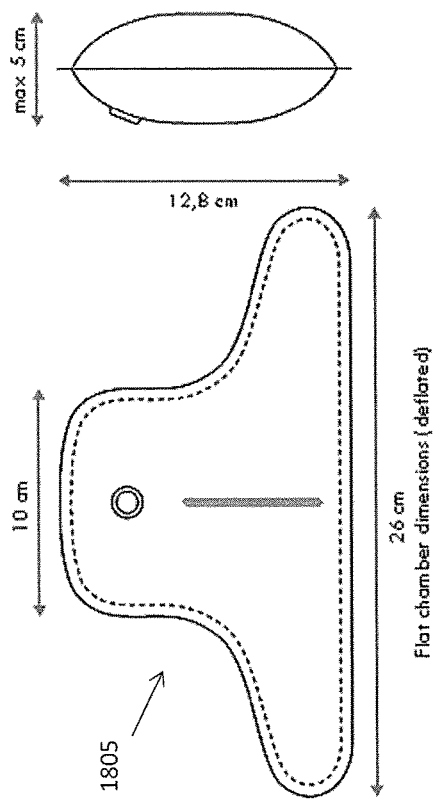

Returning now to FIGS. 18C-18E, a system including a sensing device configured as a compression garment 1801 as described above (e.g., for detecting ECG, as shown in FIGS. 2A-2B, 3A-3B and 4A-4B), may be worn directly against the patient's skin. A support structure (e.g., pad, expandable support member) 1805 may be used with the compression garment of the sensing device 1801. The support structure maybe located over the mid-pectoral region for applying pressure to hold the electrodes integrated onto the inner surface of the garment against the skin in the proper locations. The support structure may be expandable (e.g., inflatable) to allow comfortable and effective use with a variety of user body types. In some variations an additional support garment 1811 may be used to help secure the electrodes (and in some variations the support structure 1805) against the skin. The support garment 1811 in this example, shown in FIGS. 18D (front) and 18E (back), is a harness having a pair of straps that fit over the shoulders, and a central region that can push against the electrodes of the sensing device. The support garment may include relative rigid regions 1815 connected by relatively elastic regions 1817. FIGS. 18F (front view) and 18G (side view, inflated) show a larger view of the support structure 1805, with exemplary dimensions. The support structure may be attached to an outer or inner region of the sensing garment, so that it does not interfere with the measurements from the electrodes, but helps keep them pressed against the subject's chest. In some variations the support structure is integrated into the harness (support garment) such as the one shown in FIGS. 18D-18E.

Garment Wiring Arrangements

Various wiring arrangements can be used with the garments disclosed herein. Examples of wiring arrangements are illustrated in FIGS. 19-21.

Figure 19B:
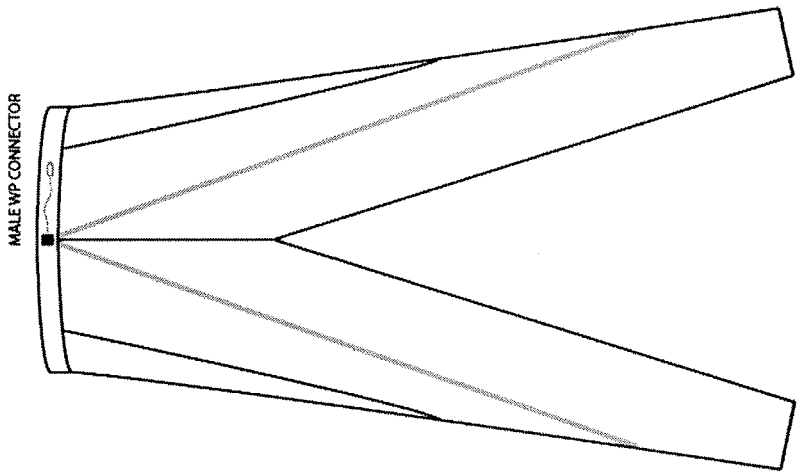
FIGS. 19A and 19B illustrate front and back views of pants.
Figure 19C:
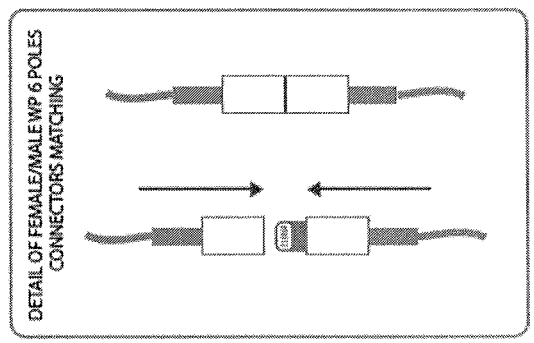
FIG. 19C illustrates an exemplary connection between the garments disclosed herein.
Figure 19A:
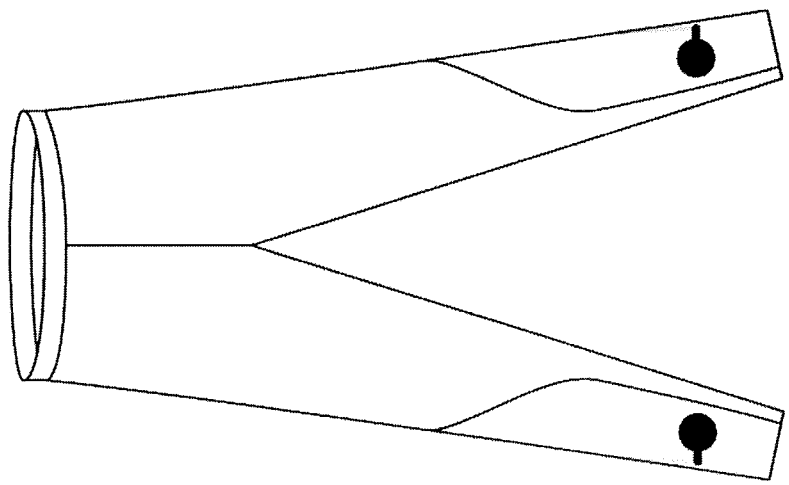

FIGS. 19A and 19B illustrate front and back views of pants. FIG. 19C illustrates an exemplary connection between the garments disclosed herein, for example between a shirt and pants. For example, the pants and shirt can each include a connector with six or more poles. One connector can have a male configuration and the other connector can include a female connector. The male and female connectors are arranged to engage with each other. The illustrated pants in FIG. 19B include a male connector and the shirt illustrated in FIG. 13B includes a female connector. In some embodiments the male/female connectors can be reversed.

FIG. 20 illustrates a wiring diagram for pants in accordance with some embodiments. The pants include a sensor for measuring the heartbeat reading of the wearer on the left leg and a sensor for measuring the heartbeat reading of the wearer on the right leg. The illustrated pants include wiring from the sensors along the pants legs to the male connector.

Figure 21B:
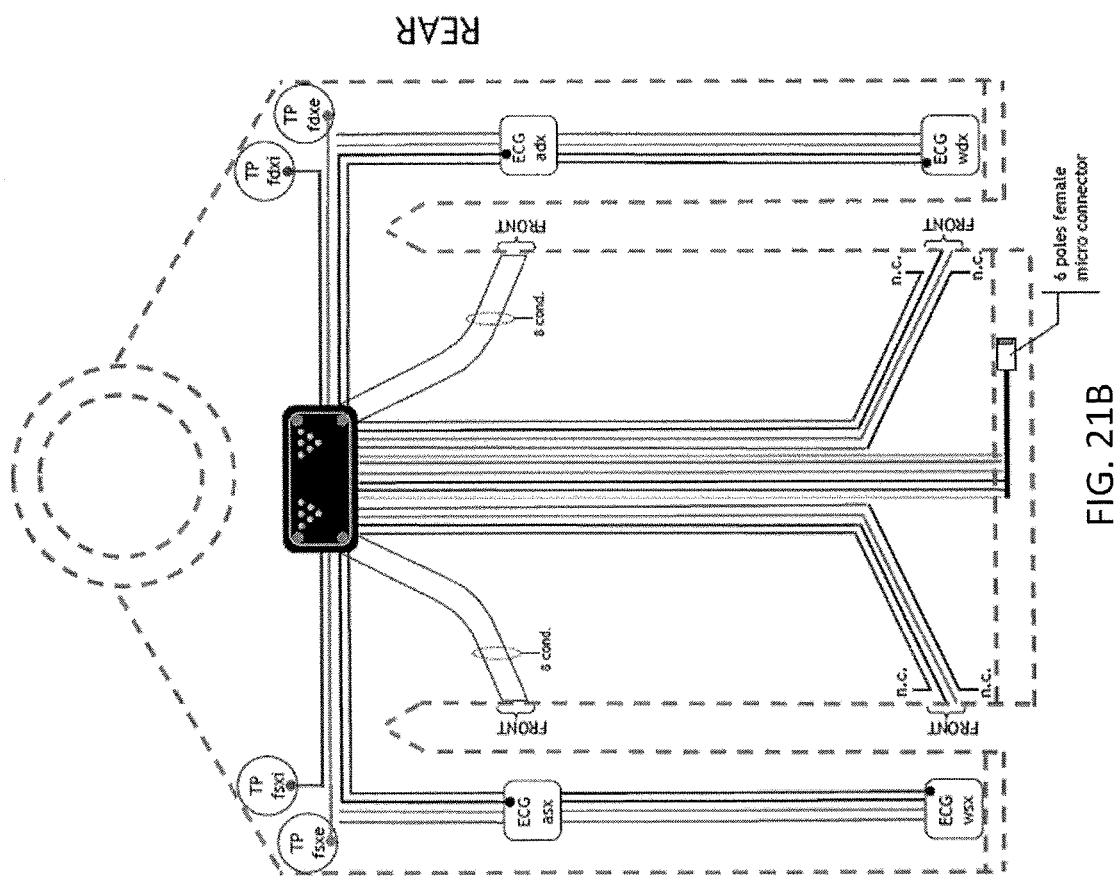
FIG. 21B illustrates a wiring diagram for the back of a garment in accordance with some embodiments.

FIG. 21A illustrates a wiring diagram for the front of a garment in accordance with some embodiments. FIG. 21B illustrates a wiring diagram for the back of a garment in accordance with some embodiments. The illustrated ECG wsx is a sensor for heartbeat reading, wrist, left side. The illustrated ECG wrx is a sensor for heartbeat reading, wrist, right side. The illustrated ECG asx is a sensor for heartbeat reading, arm, left side. The illustrated ECG asx is a sensor for heartbeat reading, arm, right side. The illustrated TP fsxi is a touch point, front position, left side, internal. The illustrated TP fsxe is a touch point, front position, left side, external. The illustrated TP fdxi is a touch point, front position, right side, internal. The illustrated TP fdxe is a touch point, front position, right side, external. The illustrated Microconn6$p$ has 6 poles WP female connector for Compression Pants CP connection. The illustrated ECG ndx1 is a sensor for heartbeat reading, neck, right side, n.1. The illustrated ECG ndx2 is a sensor for heartbeat reading, neck, right side, n.2. The illustrated ECG nsx1 is a sensor for heartbeat reading, neck, left side, n.1. The illustrated ECG nsx2 is a sensor for heartbeat reading, neck, left side, n.2. The illustrated E1$s$ is a sensor for heartbeat reading, chest, upper, n.1. The illustrated E1$i$ is a sensor for heartbeat reading, chest, lower, n.1. The illustrated E2$s$ is a sensor for heartbeat reading, chest, upper, n.2. The illustrated E2$i$ is a sensor for heartbeat reading, chest, lower, n.2. The illustrated E3$s$ is a sensor for heartbeat reading, chest, upper, n.3. The illustrated E3$i$ is a sensor for heartbeat reading, chest, lower, n.3. The illustrated E4s is a sensor for heartbeat reading, chest, upper, n.4. The illustrated E4i is a sensor for heartbeat reading, chest, lower, n.4. The illustrated E5s is a sensor for heartbeat reading, chest, upper, n.5. The illustrated E5i is a sensor for heartbeat reading, chest, lower, n.5. The illustrated E6s is a sensor for heartbeat reading, chest, upper, n.6. The illustrated E6i is a sensor for heartbeat reading, chest, lower, n.6.

Wearable System for Detection of Emotion

Also described are garments configured to determine a wearer's emotional state. Self-reported emotional state tends to be inaccurate, subjective, and therefore limited in use. Garments that may include sensors detecting various parameters (both voluntary and involuntary parameters) may be used to determine a subject's objective emotional state.

Figure 8A:
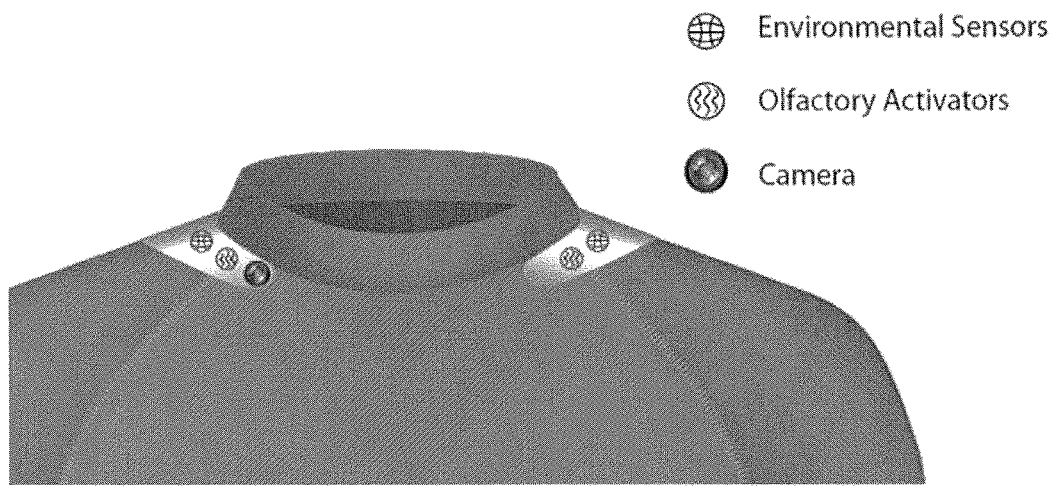
FIGS. 8A and 8B show a front and back view of a collar that may be included.
Figure 8B:
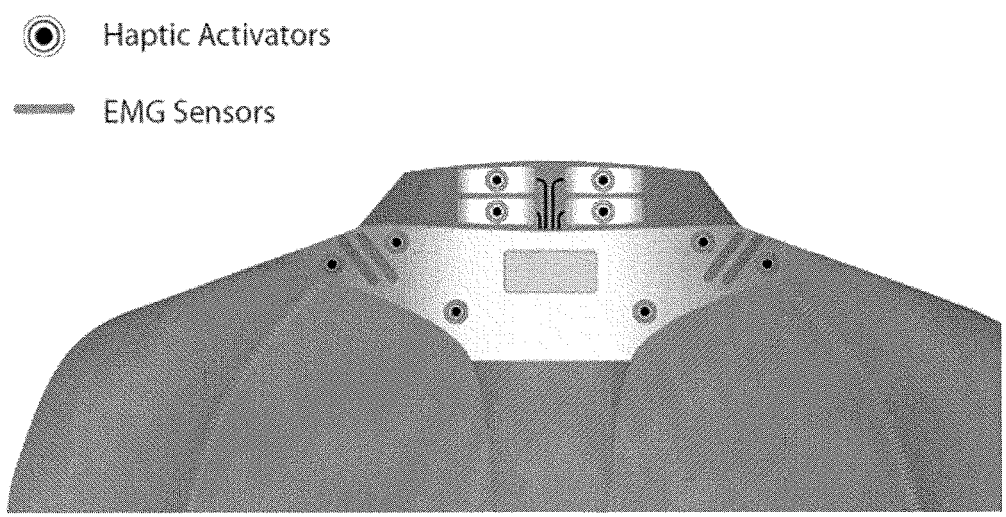

A garment may include a plurality of sensors (as described below and illustrated in FIGS. 8A-8B illustrate a collar that may be included as part of the garment and includes a plurality of sensors (any of which may be included or omitted) to detect parameters indicative of a wearer's emotional state. Sensors may include, for example: environmental sensors (detecting environmental temperature, humidity, etc.), camera(s) for visual detection, including light levels/intensity, audio detectors (e.g., detecting user voice volume, tenor, etc.). The collar may also include any of the other sensors mentioned herein and incorporated by reference (motion sensors, position sensors, acceleration sensors, etc.). In addition, the collar may include one or more outputs (haptic outputs) to provide output, including feedback, to the wearer. Haptic outputs may include olfactory (scent emitting) outputs, tactile output (vibration, pinch, etc.), and the like. The collars described and shown in FIGS. 8A-8B may be configured as an emotion communication receiver (ECR).

Any of the garments for detecting/monitoring emotion may include an ECR. An ECR may sits around the neck. In FIGS. 8A-8B the ECR is a collar that extends from the back, spreading above left and right trapeziuses, extending to the front lateral left and right sides of the neck without reconnecting on the front to facilitate the 'sliding' of the head through the collar of the 'device'. The receptor in the ECR (collar) may house a communications/analysis module (sensor module) and may include connectors (e.g., female and male connectors) as well as sensors, haptic activators and mechanisms generating pressure, vibration, temperature-changes, tensing & relaxing inputs, olfactory-inputs, etc. The front side of the activator also houses smell and taste inducing activators as well as environmental sensors to determine the quality of the environment.

The ECR may transduce received communication of physiological measurements into physically embodied messages. As an example, a friend may send to the user (wearer) of the device her emotional state as measure by her device: the user's ECR may transduce the communication into a sensorial message such as a salute by applying pressure to his shoulders. Users may exchange sensorial messages such as salute touching the shoulder, hug, push, caress, cheer up, relax, etc. and have the option to respond, including: i) Ignore; ii) accept and salute back (with their own message); iii) reject (electrical discharge). Users can choose how to receive the messages between a) pressure (wide), b) pressure (narrow-puncture), c) pressure-message (Morse-like), d) vibration, e) temperature change, or the like (including combinations). Users may also choose not accept the "emotional" valence messages to preserve her/his privacy and/or may provide a feedback to improve the accuracy of the emotions-interpretation language.

Systems for Detection, Interpretation, Transduction, Communication, and Perception of Emotions ("DITCRE")

Figure 9:
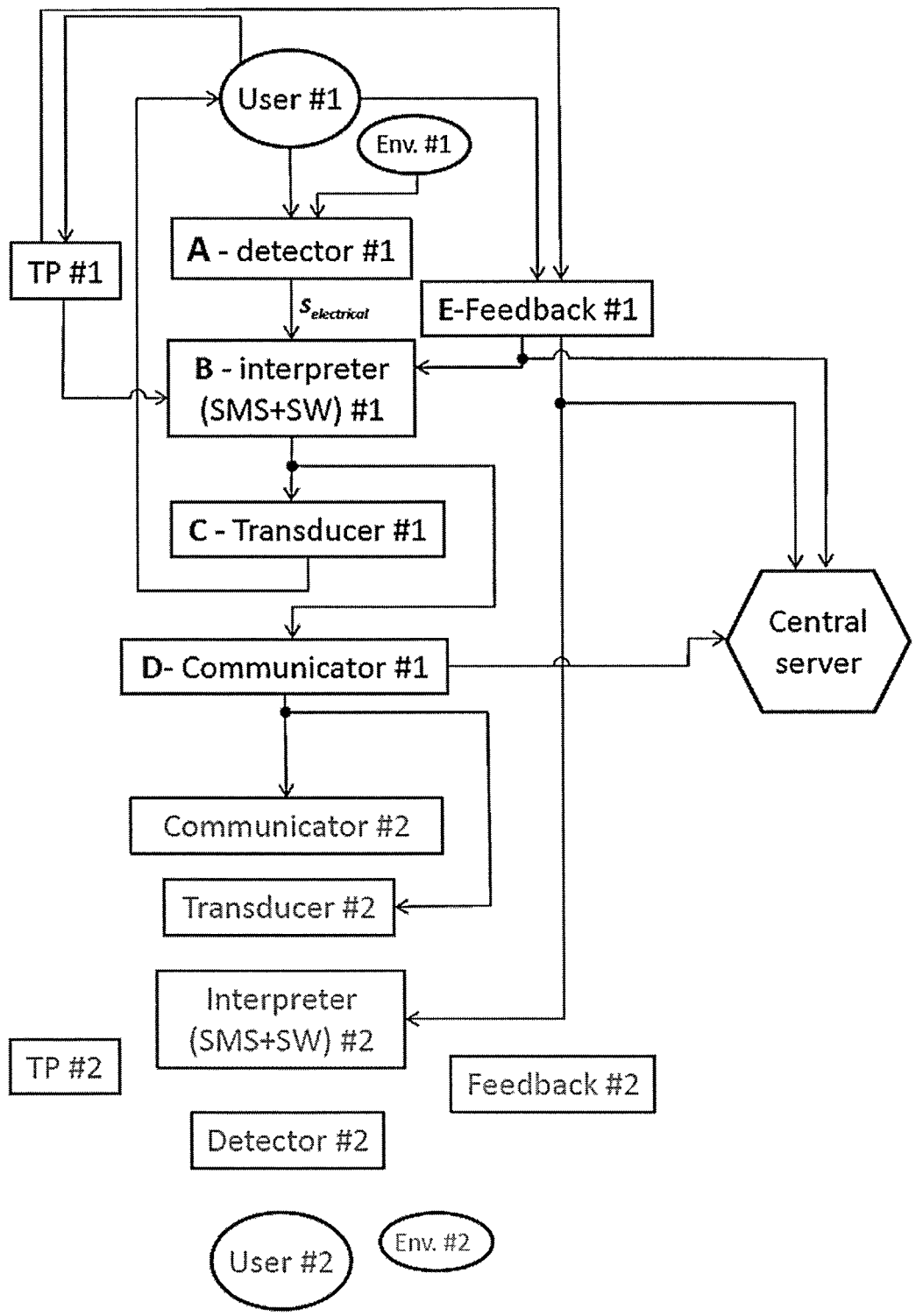
FIG. 9 shows a schematic view of operation of a garment (or multiple garments) adapted for determining emotional valence.
Figure 10A:
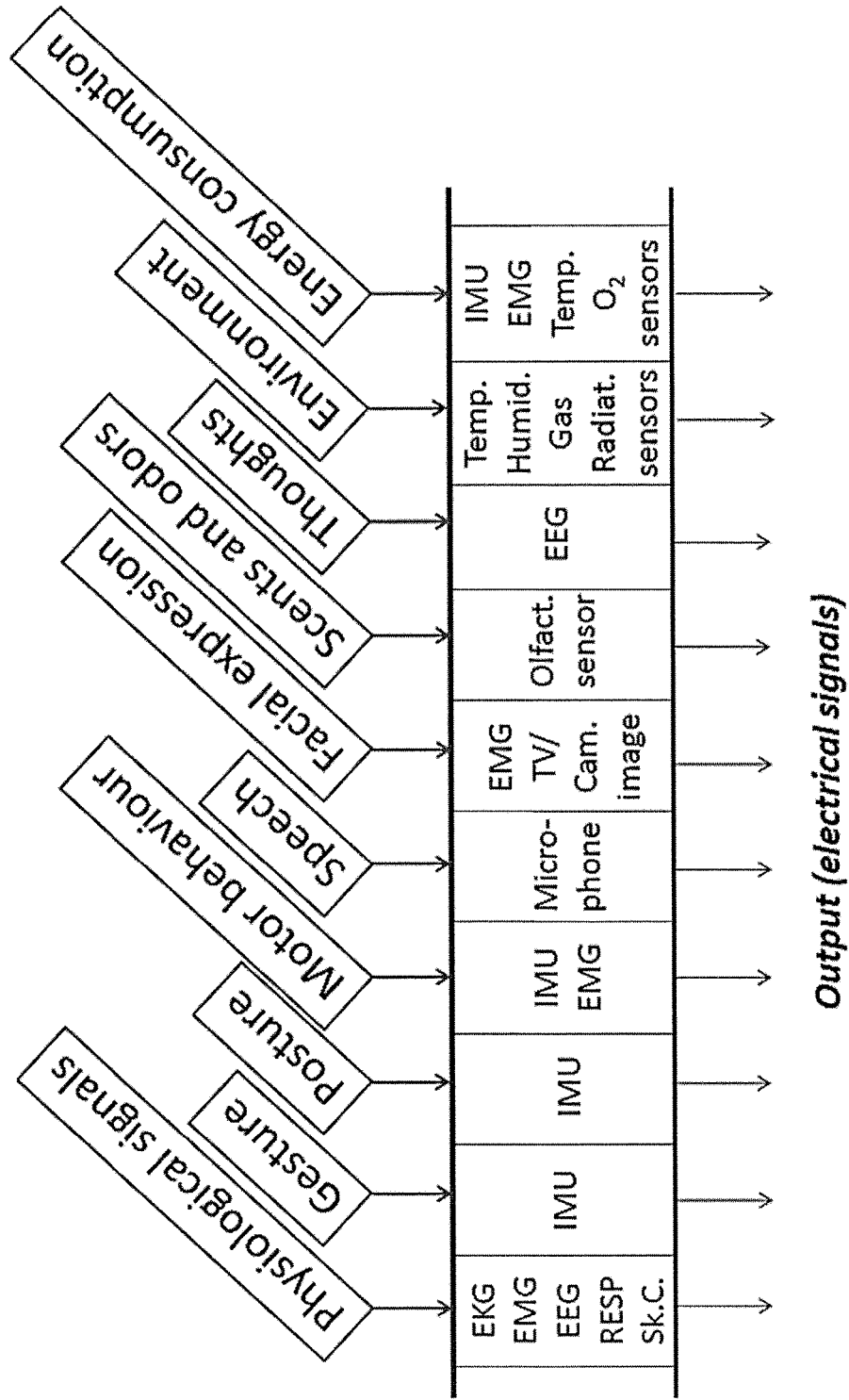
FIGS. 10A-10E are schematics providing further detail from the schematic shown in FIG. 9.
Figure 10B:
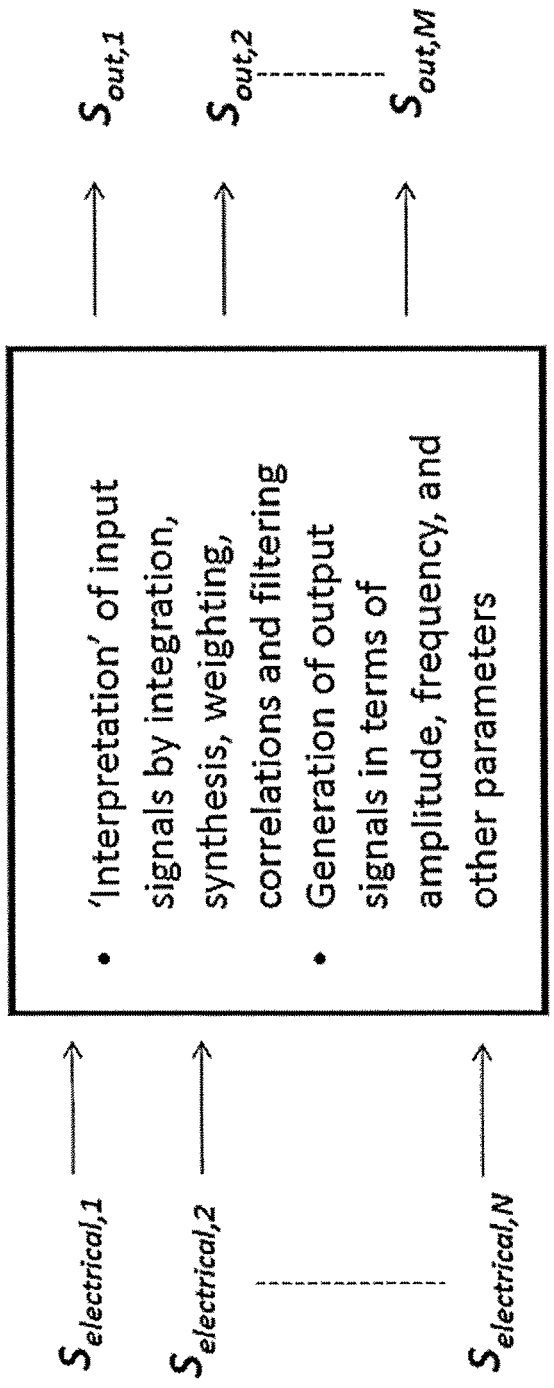
Figure 10C:
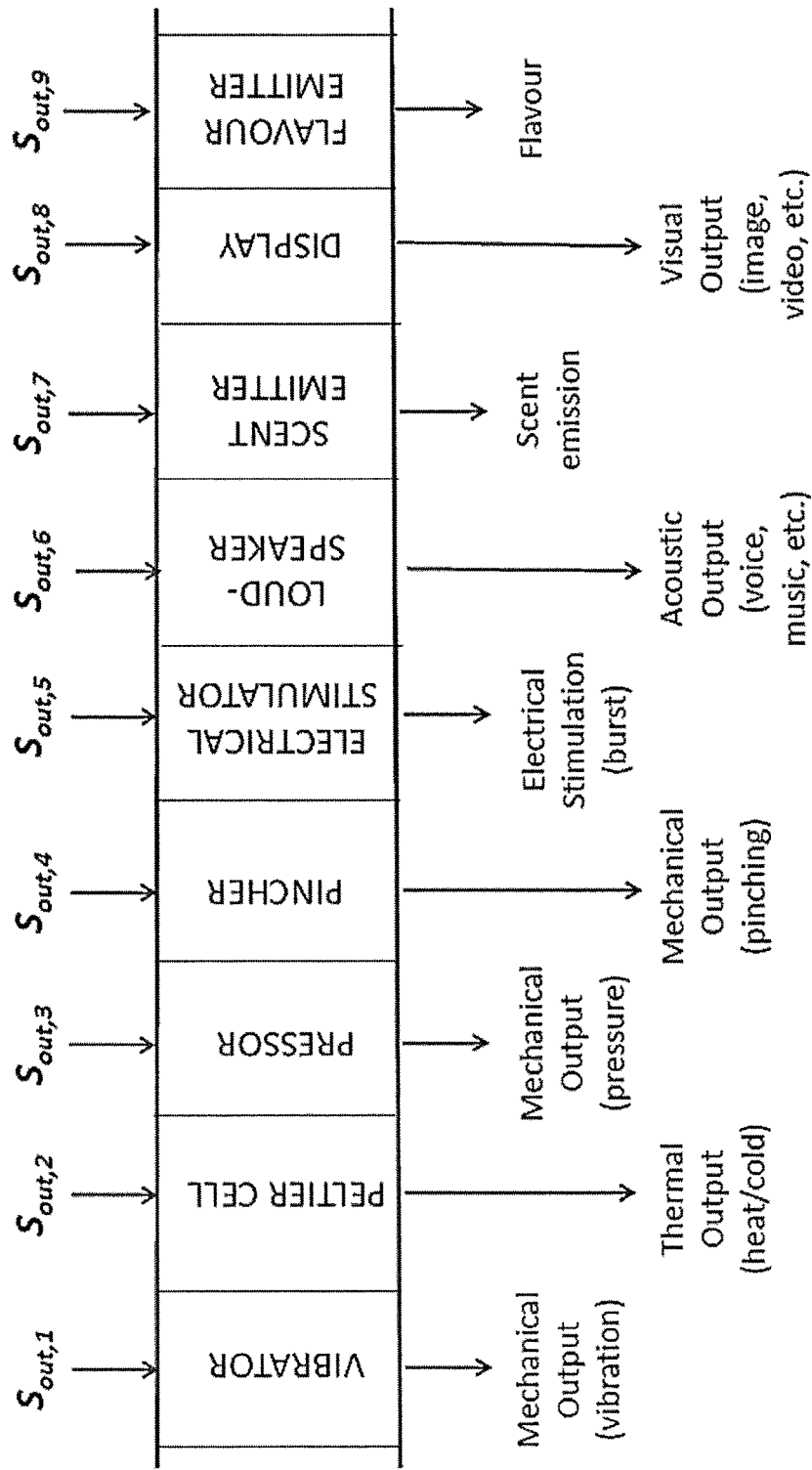
Figure 10D:
Figure 10E:
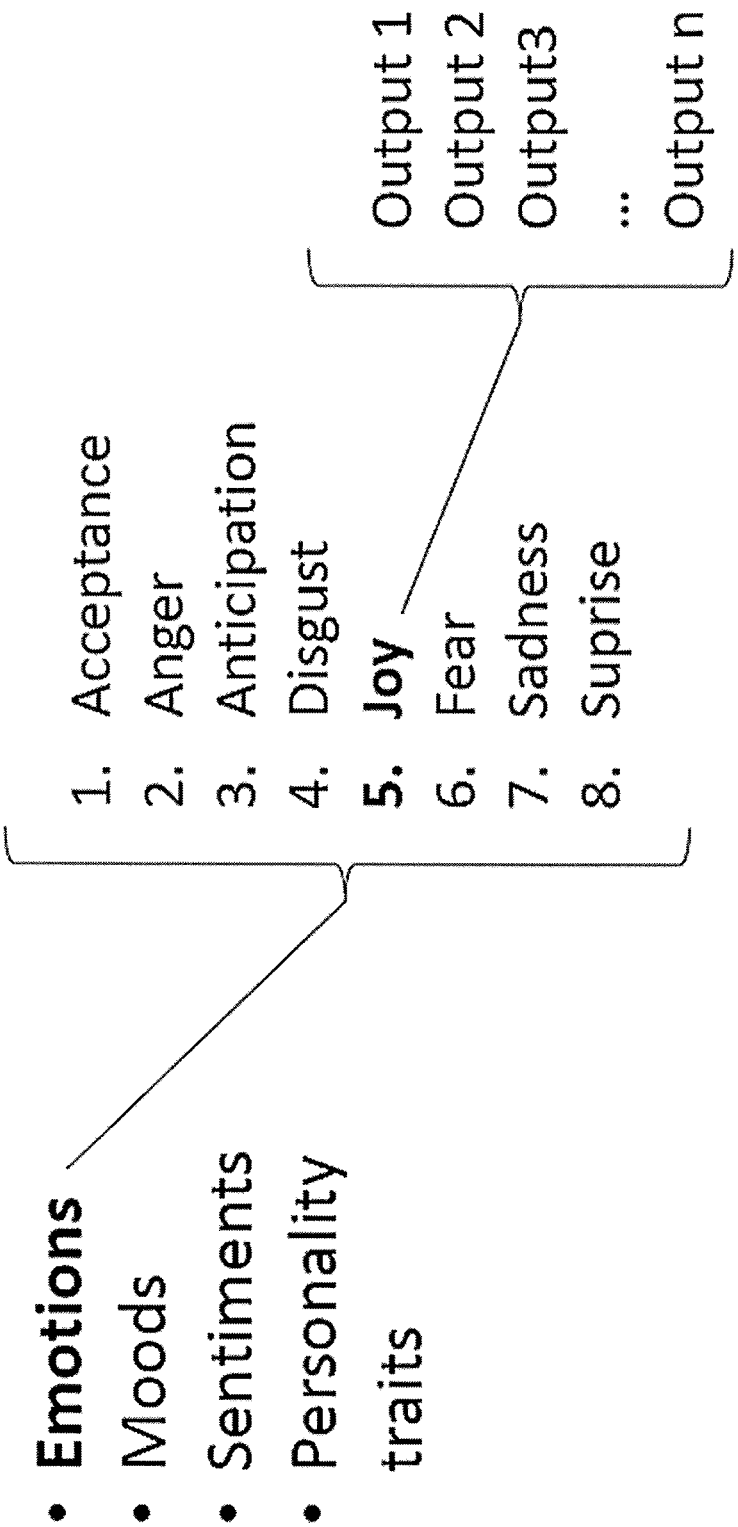

For example, a garment (including the collars, shirts and the like) described herein may be configured as a DITCRE garment. The schematic diagrams shown in FIGS. 9-10E illustrate how the DITCRE may be implemented in a garment, including a collar as shown in FIGS. 8A-8B.

The garments adapted to detect, deduce, and/or determine (derive) emotional state, and allow actions based on the derived emotional state may be used to control feedback, which may be useful in training, meditation, or learning tasks, and it may also be useful in communication with others. Thus the derived emotional state, which may be derived generally from analysis of multiple sensors worn by the user, over time, may be used to provide output. Such communication may generally be more truthful and intimate, in part because the interpretation of the emotional state is based on detected, rather than exclusively self-reported, parameters, as well as the use of different sensing modalities. A wearer may choose when and/or which emotional status they would like to communicate, and particularly with whom they wish to communicate. Any of the garments may include an output or outputs (e.g., haptic outputs) detected by the wearer, as described above. For example, haptic coding may be used to communicate even without verbal/written communication. For example, the haptic coding may be transmitted to/between wearers using a Morse-type code. In general, the haptic activators may be positioned in body regions/locations where sensitivity and emotional response is greatest (empirically determine for a specific user, or generally determined from a population of users), to optimize the location of the haptic activators.

Thus, the garments described herein may add an additional dimension when communicating, including in particular communicating between wearers. For example, body "language" may be interpreted by the sensor module and may color output from the garment or communications from the garment. The garments may also be adapted to provide feedback, comments that may have therapeutic impact on the wearer, including identifying and treating depression and the like.

In use, these garments may also provide interpretation of a subject's emotional as well as expressive output. For example, the garments may aid in interpreting across cultures/languages. Just as there are spoken languages, non-overt communication (gestures, body language, etc.) may also provide cues that he apparatus can use and express as part of a subject's output or to be received by another user.

As mentioned above, in FIGS. 8A and 8B, the collar sits around the neck, extending from the back, above left and right trapeziuses, and extending to the front lateral left and right sides of the neck without necessarily reconnecting on the front, to facilitate the 'sliding' of the head through the collar. The receptor may house a Sensors Management System (SMS), female and/or male connectors as well as: sensors (e.g., EMG sensors over left & right trapezius as additional parameter to evaluate user's emotions, such as levels of stress or relaxation; olfactory sensors as additional parameter to evaluate user's emotions; environmental sensors to determine the quality of the surrounding environment, toxicity, etc.); haptic activators and mechanisms generating pressure, vibration, temperature-changes, and the like. These sensors may communicate a user's or other user's emotions, may convey relaxing and tensing inputs as 'massages', or relaxing therapy to the user.

In some variations the garment also includes one or more olfactory activators (e.g., scent & odor reproducing activators) and taste activators placed on the front left and front right side of the ECR as an additional means to communicate user's or other users' emotional states; one or more camera (e.g., placed on the right- or left-front side of the ECR) which may be adapted to determine facial expressions as an additional parameter to evaluate other people emotions, and/or evaluate environment. The collar may also include speakers to share music and messages with surrounding people.

An ECR may be connected and can be activated and managed through the Touch Points previously descried (intentional touch regions on the garment). An ECR may receive input from the Sensor Management System, including evaluations of the user state translated into two or more emotional valences or states (e.g., 8 emotional states). The number and the classification of such states may vary in the future). Examples of emotional valences may include: acceptance, anger, anticipation, disgust, joy, fear, sadness and surprise. Emotional valences may be communicated back to the user and/or to third parties (as controlled by the user). Emotional valences may help a user to better understand their own emotions and may help communicate their emotions in a commonly shared classification to their friends.

The ECR may generally help transduce physiological measurements (e.g., ECG, Skin Conductance, EMG, respiration, etc.) and 'evaluations' (e.g., facial expression, posture, gesticulations, motor behaviors, voice tones, eyes-sleepiness or alertness, movements, actions, etc.) into intelligibly qualified emotions. The EMG may also help communicate those emotions through voice, physically embodied messages or visual displays. As an example, a friend may send her emotional state as measured by her garment: the user's may transduce the communication into a sensorial message (such as a salute, by applying pressure to his shoulders; a scent or a taste emitted a haptic describing her emotional state, a color describing her emotional state, or an audio or visual description of her emotional state. Users may exchange sensorial messages such as salute touching the shoulder, hug, push, caress, cheer up, relax, etc. and may have the option to respond. For example, a user may ignore, accept and salute back (with their own messages), and/or reject (electrical discharge). A user may also choose how to receive the messages between a) pressure (wide), b) pressure (narrow-puncture), c) pressure-message (Morse-like), d) vibration, e) temperature change, f) audio description, g) visual description, etc. A user may control the communication exchange and can choose not to accept the emotional messages to preserve her/his privacy. This communication modality (including the use of the haptics) recognizes that other, not limited to aural or visual (spoken/written) modalities such as touch may be more effective (or differently effective) when communicating emotional content/context. Thus, any of the garments described may transduce a user's physiological measurements into intelligible communication, including communication of the user's emotional valence. A user may choose the format (e.g., different forms of touch, audio, graphs, drawings, numbers, . . . ) of communication data. For example, the garments may allow a user to transduce the users' physiological measurements (emotional valence) into voice, physically embodied messages or visual displays (display or touch screen on forearms, on glasses or on smartphone) to other users. Further, the garments, and particularly those with ECR may allow a user to improve the accuracy of the emotions-interpretation language by enabling them to provide feedback on data evaluation, representation and communication.

An ECR system may also act as a self-improving system (much like voice-recognition most advanced systems): the more users will express and communicate their emotions the more accurate emotions qualification, description and communication will be. In addition, the user may activate and interact with the system through touch points on the garment.

ECR may be used in a variety of contexts. For example, ECR may be used as a lie detector. Typically, lie detectors detect changes in body functions that are not easily controlled by the conscious mind and may include bodily reactions like skin conductivity and heart rate; they also may consider respiration rate, blood pressure, capillary dilation, and muscular movement. These measures may indicate a short-term stress response which can be from lying or significance to the subject. Problems arise because they are also associated with mental effort, and emotional state; so they can be influenced by fear, anger, and surprise for example. The EDR systems described herein, which may be used for long-term monitoring and training/conditioning of a user, may be better at distinguishing such responses from artifact responses.

ECR may also be used for safety evaluation, such as environmental safety, examining air (level of pollution, toxicity, etc.), water (no drinking, no swimming, etc.), soil; examining locations, e.g., searching risk in surrounding areas, such as crime reports in the area, avalanches, flooding, trees falling, toxic area; indicating functions based on time of the day, time of the year, etc., such as recurring events like parades, etc. The ECR may also monitor user behavior and provide data/feedback on such behaviors (e.g., eating, drinking, substance abuse, etc.). A garment with ECR may also assist and/or provide feedback on traveling, such as driving (driver behavior, driver's track record, surrounding traffic, type of road, weather conditions), flying, sailing, or otherwise operating machinery/vehicles.

Finally, a garment with or without ECR may be helpful for safety actions: a) emergency calls: 911, doctor, GPS tracking, family member monitoring/tracking, coaching; b) provide relevant information: type of danger, location, user's physiological data, user's medical and relevant data, user's emotional data, health insurance, financial profile, and the like. The garment (with our without ECR) may also be more interactive, providing suggestions on health, including activity level, eating, and the like, or on emotional wellness.

As described in FIGS. 10A-10E, the ECR may perform measurements and evaluations based on one or more of: physiologic (measured through sensors) information, gestures (e.g., IMUs and accelerometers on wrists), posture (e.g., IMUs on module, each shoulder, mid spine, lower spine), motor behavior (e.g., IMUs on each ankle and each wrist), speech evaluation (e.g., recording voice), facial Expressions (e.g., sensors on ears, forehead and neck for self, video camera for other persons), scents or odors (e.g., chemical sensors), EMG, and/or EEG sensors, and/or evaluation of the environment (e.g., temperature sensors, pollution sensors, etc.).

For example, FIG. 9 outlines a pair of users that may interact, each with a garment adapted for detection, interpretation, transduction, communication, and perception of emotions. Each of these areas (labeled A-D) are described in greater detail in FIGS. 10A (detectors, including sensing devices), 10B (interpretation of the sensor data to determine an emotional valence), 10C (actuators and communication, including output of valence information from the user or another person using a similar device), and 10D (feedback).

Such apparatuses may find use with the general population, including people interested in monitoring their well-being status during their daily regular activities (walking, eating, working, seating in front of their computer . . . ), and also for athletes who want to monitor their fitness level during their training or specific sports. Participants (users) may be required to register and fill a list similar to the one filled in hospitals or by professional athletes: the more questions the participant responds the more accurate their evaluation will be.

Figure 11:
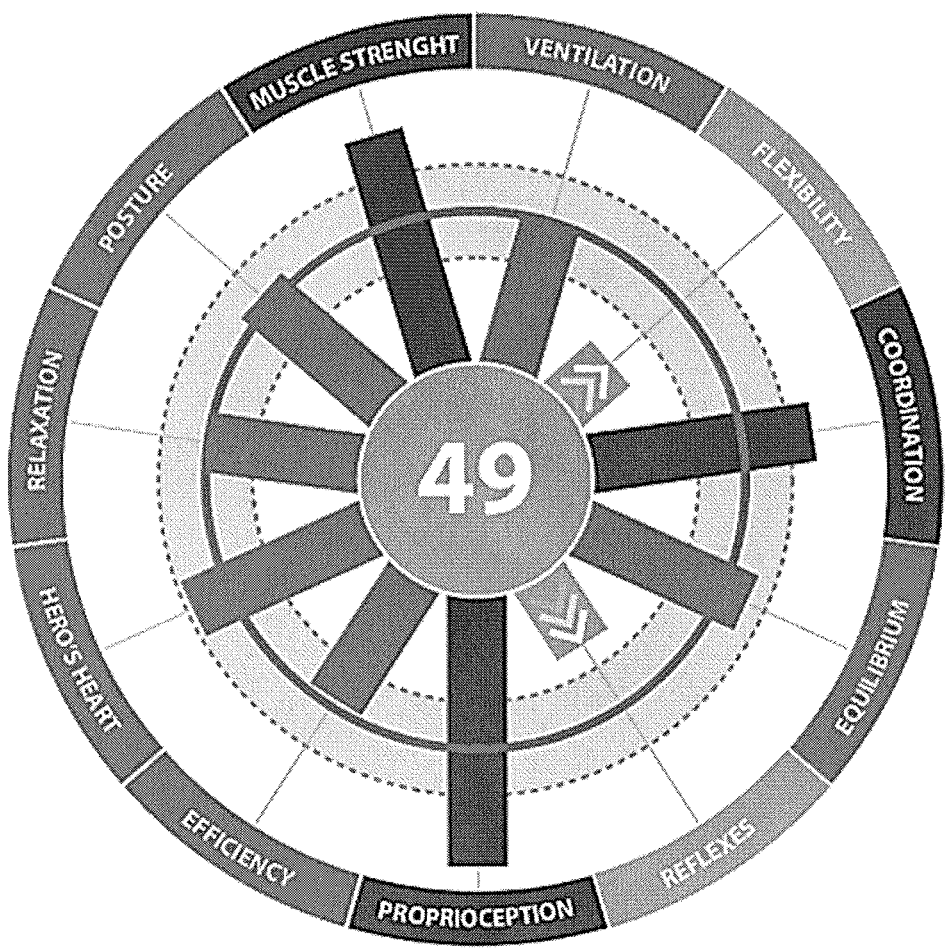
FIG. 11 is a graphical illustration of a determination of well-being that may be made from a user wearing a garment as described herein.
Figure 12:
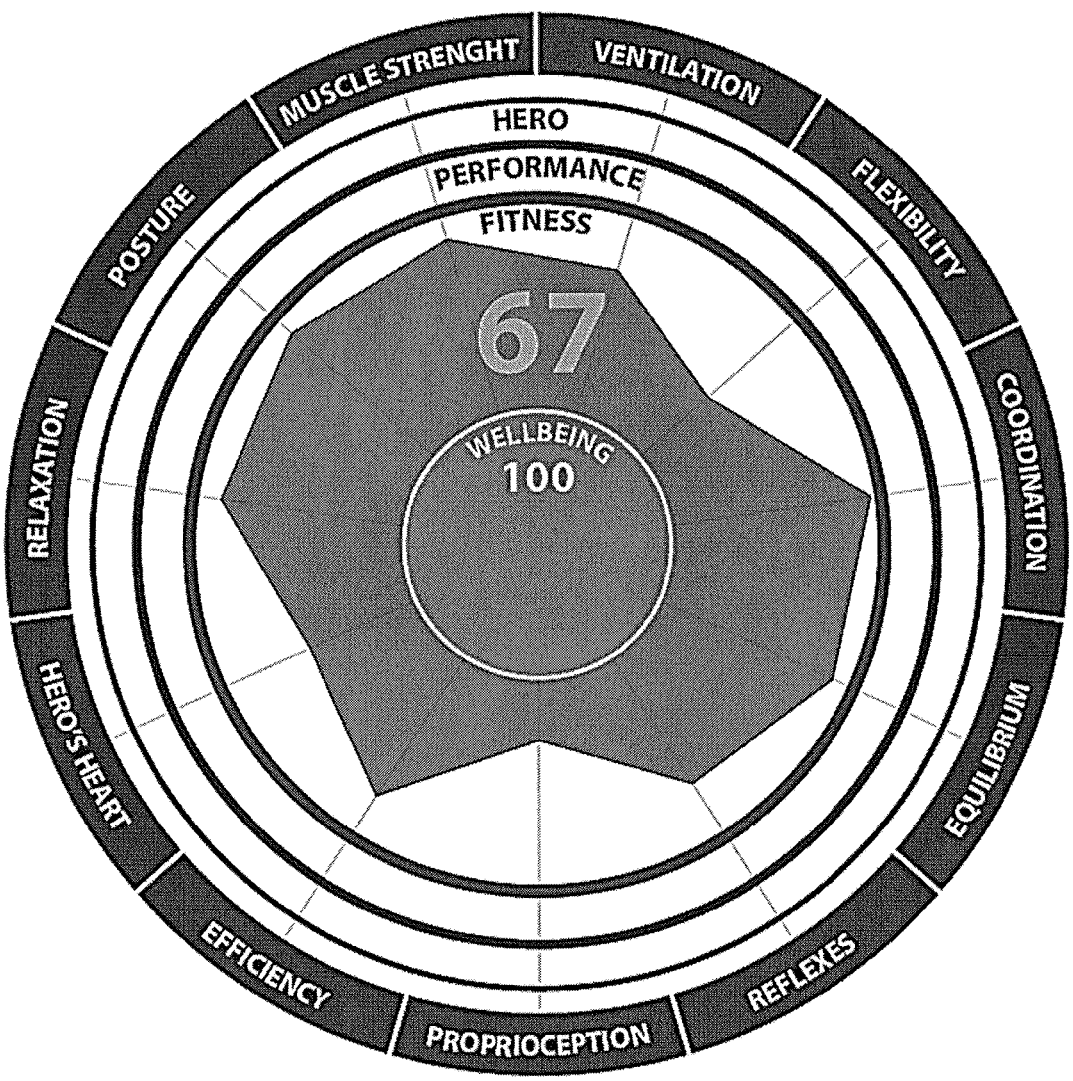
FIG. 12 is a graphical illustration of a fitness ranking/analysis that may be made from a user wearing a garment as described herein.

FIG. 10E illustrates one method in which an emotional valence may be determine for a particular user, based on the inputs of various sensors, and may also include feedback specific to a particular user. In addition, FIGS. 11 and 12 illustrate graphically how an ECR may operate to determine from the subject their actual emotional valence or an overall estimate of "well-being" (FIG. 11). Similarly, the sensors may be used to provide the user an indicator of overall fitness (FIG. 12). These charts may provide an evaluation that can be presented graphically, as shown in FIGS. 11 and 12, providing a snapshot of the wellbeing of a person or the fitness level of an athlete. The evaluation may be based on a number of parameters (e.g., that can vary in number, such as from 8 to 20 or more depending on the number of sensors in a given device). Each graph may provide: (1) a value that synthesizes the well-being or the fitness level of the user based on an adjusted synthesis of all the parameters; (2) a value that synthesizes the well-being of the fitness level of the entire population (given in absolute number and % of the number) so that the users will immediately know if she is above or below average. This value increases in accuracy with the number of users; (3) the value may be adjusted to the person specific needs. For example, since 30% of people above 65 fall and get injured for lack of equilibrium, a 70 year old person's equilibrium may be given a higher relevance then for a 40 year old person. Similarly, a self-identified weight lifter's strength may be given a higher relevance then for a tennis players, or endurance a higher relevance for a super triathlon athlete then for a slalom skier. A user can thus use this sort of graphical output to see her value and the total population value for each one of the parameters. A user can further go into the details for each parameter. For example, the efficiency score, compared to the population's efficiency score; how efficiency is calculated; the biometrics involved into the calculation; the accuracy of the calculation considered the state of the technology on hand; the medical accuracy, etc.

A user who chooses to improve a given parameter (say equilibrium for a 70 year old) may be given a list of exercises to do it (jump rope, one leg stand, etc. . . . ). A haptic feed-back may be used to tell the user when her equilibrium is below or above average, and/or an improvement indication, and/or a session's performance versus best personal performance.

The many sensors and haptic actuators in an apparatus maybe adapted to allow a user to communicate (e.g., through audio, haptic or visual messages) to other users while they are exercising in order to maximize their efficiency, improve their execution. For example: a) communicate if athlete is not wormed up when starting exercising; b) if temperature is too cold when finishing the exercise; c) if the posture or body position is not appropriate when performing the exercise; d) if the user his overloading his muscles; e) if the athlete is not pushing enough during the training session.

Stretchable Conductive Ink Patterns

Any of the apparatuses described herein may include a stretchable conductive ink pattern. In general, the stretchable conducive ink may have a stretchability ranging from 5% to 200%, e.g., it may be stretched more than 2 times (200%) of its at rest length without breaking. In some examples the stretchable conductive in can be stretched to more than 3 time (300%), more than 4 time (400%), or more than 5 time (500%) of its neutral, at rest length. The stretchable conductive ink patterns are conductive, having a low resistivity. For example, the bulk resistivity may be between 0.2 and 20 ohms*cm (and the sheet resistivity between about 100 to 10,000 ohms per square). The conductivity may be dependent upon the stretch, although it may stay within the ranges described above (e.g., between 0.2 and 20 ohms*cm).

Structurally, any of the stretchable conductive ink patterns described herein are typically made from a specified combination of an insulative adhesive and a conductive ink. In general, a stretchable conductive ink pattern includes a first (or base) layer of insulative and elastic adhesive and a layer of conductive ink, where the conductive ink includes between about 40% and about 60% of conductive particles (e.g., carbon black, graphene, graphite, silver metal powder, copper metal powder, or iron metal powder, etc.), and a gradient region or zone between the insulative, elastic adhesive and the layer of conductive ink. The gradient region is a combination of the conductive ink (e.g., conductive particles of the conductive ink) and the adhesive, in which the concentration of the ink (e.g., conductive particles) may vary with depth. In general, the gradient region may be a mixture of the conductive ink (e.g., conductive particles) and the adhesive wherein the concentration of conductive ink in the gradient region may be less than the concentration of the conductive ink in the conductive ink layer. The gradient region may be a continuous gradient of conductive ink (particles), e.g., it may be nonhomogeneous, or it may be a step gradient.

Typical conductive inks, such as those used for printed circuits and even flexible circuits, are not sufficiently stretchable to be used for garments, including in particular not for compression garments and may break or form discontinuities when used. Surprisingly, the combination of conductive ink, gradient region and insulative adhesive provides a conductive ink composite that is both conductive and highly stretchable/extensible. The composition of the conductive ink that may be used in as described herein generally includes: between about 40-60% conductive particles, between about 30-50% binder; between about 3-7% solvent; and between about 3-7% thickener. Further, the use of an intermediate, "gradient" region between the insulating adhesive and the conductive ink layer(s) has also been found to be important.

The conductive ink used and combined with the adhesive to form the conductive ink pattern typically has a low toxicity and hypo-allergenicity (e.g., a formaldehyde concentration lower than 100 ppm), and a resistance to damage from washing, including preservation of electrical and elastic properties following repeated washing cycles.

Figure 39A:
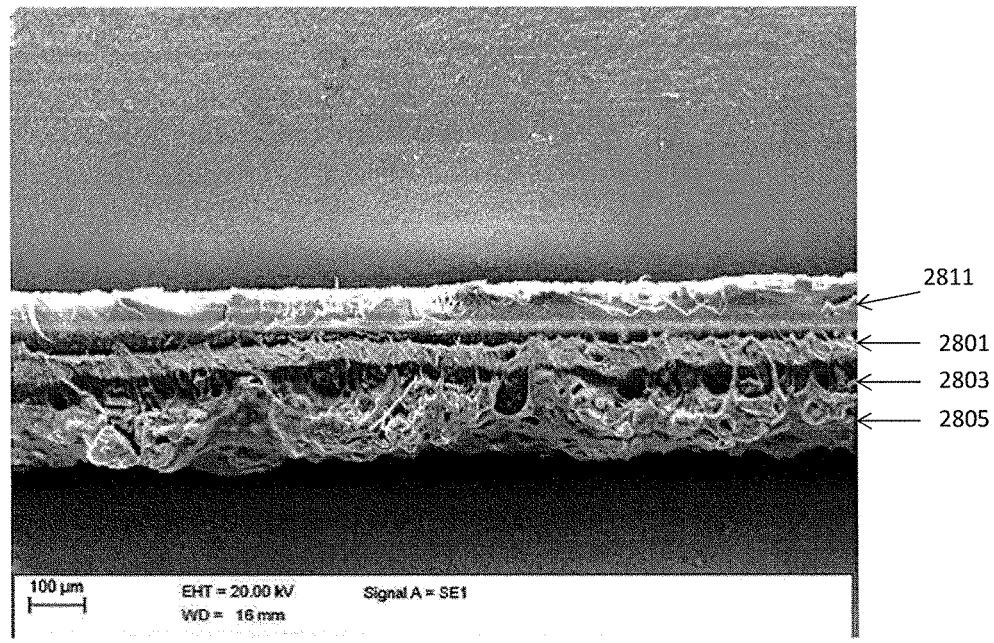
FIG. 39A is a scanning electron micrograph (SEM) of a section through one example of a stretchable conductive ink pattern, illustrating the conductive ink layer and an elastic adhesive layer with an intermediate gradient region between the two.
Figure 39B:
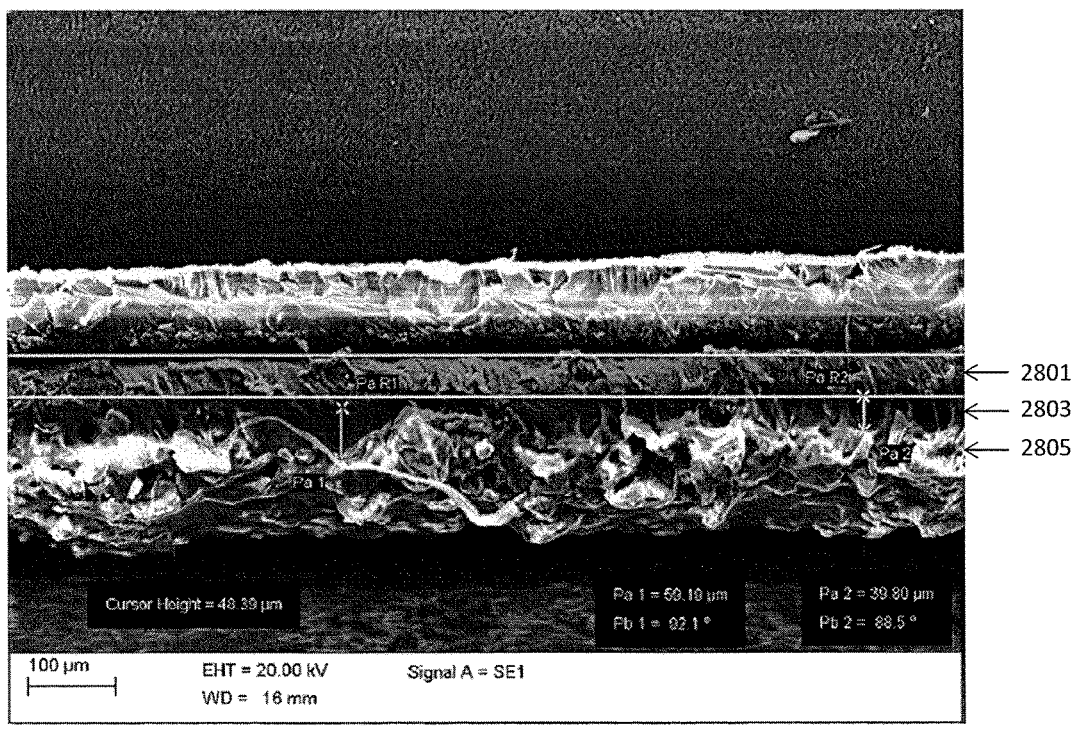
FIG. 39B is another SEM of a section through an example of a stretchable conductive ink pattern, showing the thicknesses of each region/layer.
Figure 39C:
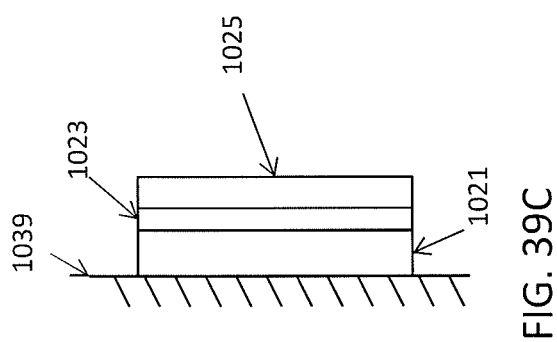
FIG. 39C is another variation of a conductive ink pattern, including an adhesive, gradient region, and conductive ink, as described herein.

FIG. 39C illustrates one variation of a conductive ink pattern (a conductive ink composite) that has a high degree of extensibility or stretchability. In this example, the conductive ink pattern is applied on a substrate 1039 (which may be a fabric, including a compression fabric forming a compression garment or a transfer substrate), and includes a first layer of electrically insulative elastic adhesive 1021. An outer layer 1025 of conductive ink is separated from the adhesive layer 1021 by an intermediate gradient region 1023 which is a mixture of the conductive ink and the adhesive wherein the concentration of conductive ink decreases from a region closer to the layer of conductive ink 1025 to the layer of elastic adhesive 1025. This gradient region may be referred to as an intermediate layer and may be have a nonhomogeneous mixture/distribution of the electrically conductive ink with the adhesive. An optional outer insulator (e.g., insulating resin, not shown) may also be included over the conductive ink layer. The outer conductive ink may be formed from multiple layers of conductive ink.

For example, FIGS. 39A and 39B show electron micrographs (scanning electron micrograph, SEM) of a sample of a conductive ink pattern placed between two supports of aluminum. In FIG. 39A, the lowest layer 2805 is the adhesive, the layer adjacent and above that is the gradient region 2803, and the layer adjacent to and above that is the conductive ink 2801. In this example an additional insulative layer (resin 2811) is placed on top of the conductive ink. In general, the conductive ink may be formed of multiple layers of applied conductive ink. In FIG. 39A the conductive ink layer was formed by sequential application of 5 layers; these layers are not visible in the micrograph.

In FIG. 39B, an electron micrograph was used to quantify the thickness of the layer. In this example, the conductive ink layer 2801 (region) has a thickness of about 50 the gradient (transition) zone 2803 has a thickness of between about 40-80 µm, and the glue 2805 has a thickness of about 150 µm.

The gradient region may be functioning both to enhance the stretchability of the conductive ink, as well as enhancing the stability of the conductivity. Electrical conductivity is allowed by the upper region, while the high degree of mechanical stretching allowed (due to the adhesive) is enhanced by the lower layers. The incomplete mixing of the conducive ink and the adhesive found in the gradient region appears to result in a structure and composition that can be repeatedly stretched and released, while retaining the conductivity. Note that the resistivity of the composite may change with stretch (generally increasing resistivity with stretch), and this property may be used to detect stretch.

In general, the gradient region may be formed by combining the conductive ink and the adhesive before either one is completely dried, allowing them to combine to form the transition zone having the appropriate thickness. The composition of the ink (e.g., between about 40-60% conductive particles, between about 30-50% binder; between about 3-7% solvent; and between about 3-7% thickener) may determine the formation parameters of this overlapping (gradient) region. FIG. 40A-40D shows an example of the compositional distribution of an example of a stretchable conductive ink pattern (composite). In FIG. 40A, carbon is shown, and is ubiquitous throughout the layers, as expected for organic materials. In FIG. 40C, the distribution of silicon is concentrated on the surfaces of the substrate (a plastic substrate onto which the conductive ink pattern is made), and diffuse in the conductive ink pattern. Similarly in FIG. 40D the oxygen is diffused everywhere. In contrast, as shown in FIG. 40B, sulfur is concentrated in the ink but not the glue. The gradient of sulfur therefore indicates a gradual transition from the ink to the glue in the area morphologically similar to the glue. This region is the gradient zone or region, where non-homogenous mixing has occurred.

In FIGS. 39A-39B and 40A-40C, the stretchable conductive ink pattern is formed on a substrate of polyester paper onto which the ink and adhesive are printed (along with an outer insulating resin). This pattern may then be applied to the garment so that it sticks to the garment and the substrate (paper) can be peeled off that that the ink remains. The adhesive is highly elastic, and allows stretching. The conductive ink, alone, may be somewhat stretchable, but is not nearly as stretchable as the adhesive, perhaps because of the rigid metallic particles. The intermediate region (where the adhesive and the conductive ink are overlapping) is important. Complete mixing in this zone would homogenize this region, and likely reduce the conductivity (as the adhesive is insulative); the partial mixing may preserve the stretchability while preserving conductivity.

Figure 41:
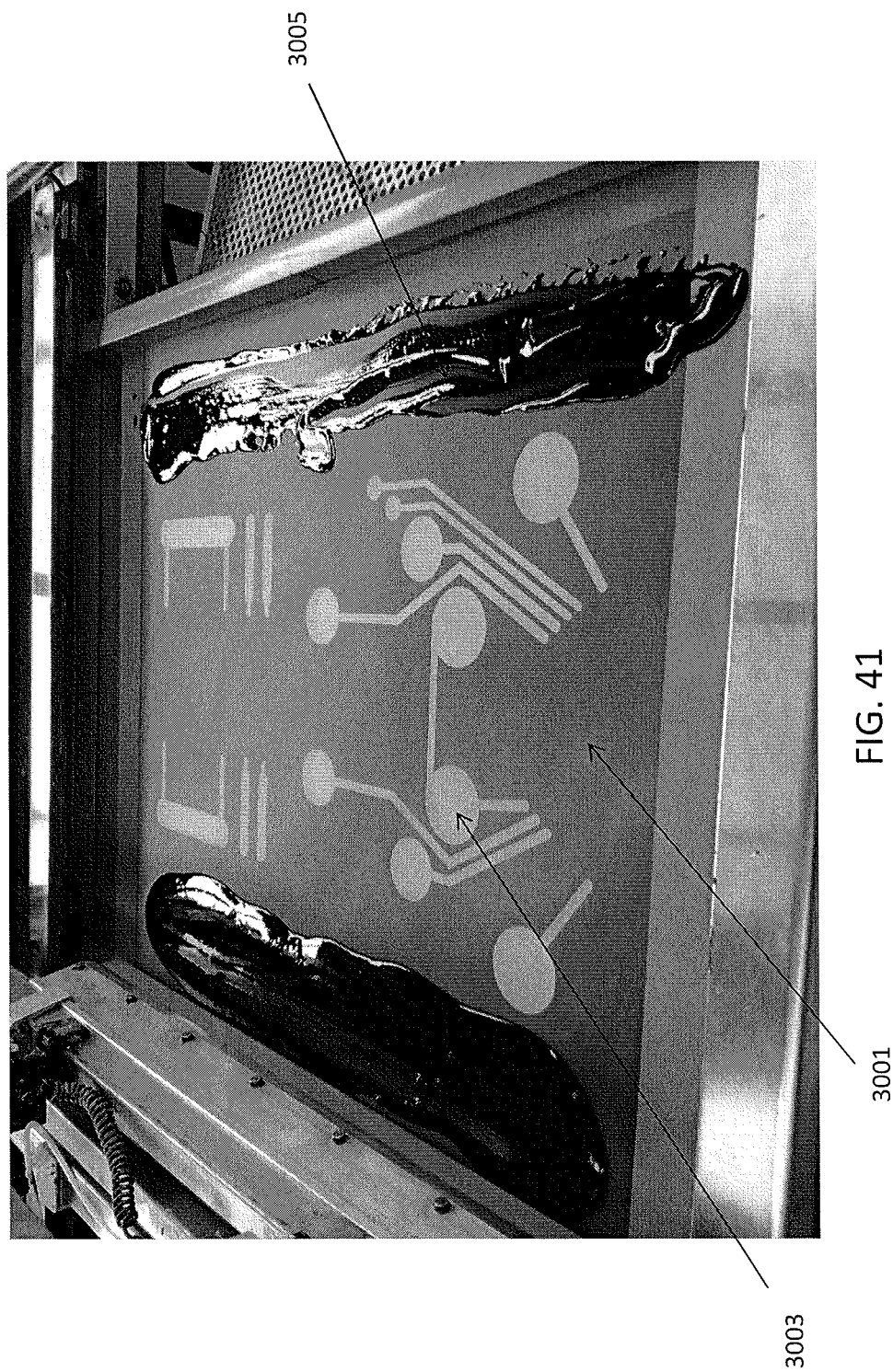
FIG. 41 illustrates on method of printing a stretchable conductive ink pattern onto a substrate.

An outer protective layer that insulates the conductive ink may be included when desired, e.g., when forming conductive traces, or patterning a sensor or electrode, though it may be left off contract regions of an electrode, for example. The resin ("primer") may be one or more layers of insulating material that does not link with or mix with the conductive ink. For example, the resin material may be insulating and may also help protect from detergents and fluids (water) used for washing, as well as protecting from scratching, etc. In some variations the resin is an acrylate (e.g., acrylic resin). Aldehyde or acrylic (synthetic resins) may also be used. Any of the components (e.g., conductive ink, adhesive, and resin) may be applied by printing. For example, FIG. 41 illustrates one example of method used to print the stretchable conductive ink pattern onto a substrate. In FIG. 41, a first mask ("screen") 3001 is used to form the pattern of adhesive (electrically insulative glue) to be applied to the substrate, beneath the screen 3001 (not visible). For example, when applying directly onto a fabric, the adhesive may be applied in a screening process by pulling the 'wet' adhesive 3005 across the screen so that it forms the pattern shown. Multiple applications of adhesive may be applied, or the thickness may otherwise be adjusted (e.g., by the application force, viscosity and/or screen opening size). Thereafter a second screen (or the same screen) may be used to apply the pattern of electrically conductive ink. Multiple applications of conductive ink may be applied to achieve the desired thickness (typically less than the thickness of the adhesive. The second screen may have openings that are slightly smaller than the pattern used for the adhesive, or they may be the same size (or in some variations, larger). The adhesive and the conductive ink may be co-extensive. When applying to a transfer substrate the order may be reversed, so that the conductive ink is applied to the substrate before the adhesive. As mentioned an insulating resin (e.g., protective layer) may be applied adjacent to the conductive ink layer.

In some variations of the conductive ink structures described herein (e.g., traces, sensors, etc. formed of conductive ink, e.g., by printing directly and/or transferring to a fabric), the conductive ink comprises conductive particles, such as carbon black, coated mica (e.g., mica coated with antimony-doped tin dioxide), graphene, graphite, etc. The material may also include a base/binding material that functions to permanently bind to the fabric all the solid components contained in the ink. This binding material (binder) may be an acrylic water base, e.g., water-based polyurethane. The conductive ink material may also include a primer, that increases adhesion and compatibility between the various products applied and increase the resistance to washing process. The conductive ink may include an adhesive (e.g., glue, such as an acrylic, polyamide, etc.), that ensures the transfer of the conductive product to the fabric. Any of these conductive inks may also include a de-foamer to eliminate air and foam contained in the product, and a catalyst to allow the complete crosslinking of the binder. Additional additives may be included to increase the printability and the stability of the product. A thickener that thickens the liquid components contained in the product may also be included. Transfer of the resulting ink material may be obtained by a silkscreen print process as illustrated above. For example, a silk screening process may include a serigraphy frame type (from 24 wires up to 120 wires), and transfer supports films such a paper, cardboard, polyester, acetate, reflector, etc. The number of layers screened/applied may be from 1 up to 50 or more. The order of the layers applied may be sequential (and inverted when the material is to be transferred). For example, the primer may be applied as the next to last layer, with the adhesive being the last layer formed. The conductive ink may be dried, e.g., by IR oven, hot air blower or cold air blower. As mentioned above, this ink material (including the adhesive base) may be applied to any appropriate material, including, e.g., cotton, woolen, nylon, polyester, polyamide, Lycra, leather (natural or synthetic), plastic films, ESD fabric, etc.

The ink may be transferred to apply to a garment using a thermo press machine, e.g., by applying an application pressure from 2 bar up to 90 bar at an application temperature from 100° C. up to 250° C. for an application time from 5 sec up to 50 sec. The final polymerization may be performed by IR oven at a temperature from 50° C. up to 180° C. (e.g., using a conveyor belt speed from 0.1 m/sec up to 5 m/sec).

As mentioned above, the conductive ink patterns described herein may be any appropriate pattern, including traces (e.g., connecting various elements on the garment), sensors (e.g., touch point sensors, stretch/respiration sensors) or electrodes (EEG sensors, ECG sensors, EMG sensors, etc.). When used as a connector it may be combined with additional conductive connector elements, including, but not limited to conductive threads, stitched zig-zag connectors, conductive traces formed on a substrate such as Kapton, etc. Such combinations of conductive ink patterns and additional highly conductive materials may be particularly useful over longer lengths. In some variations the stretchable conductive ink material may be used as a trace or connector in regions where the garment will be stretched a lot.

Figure 42A:
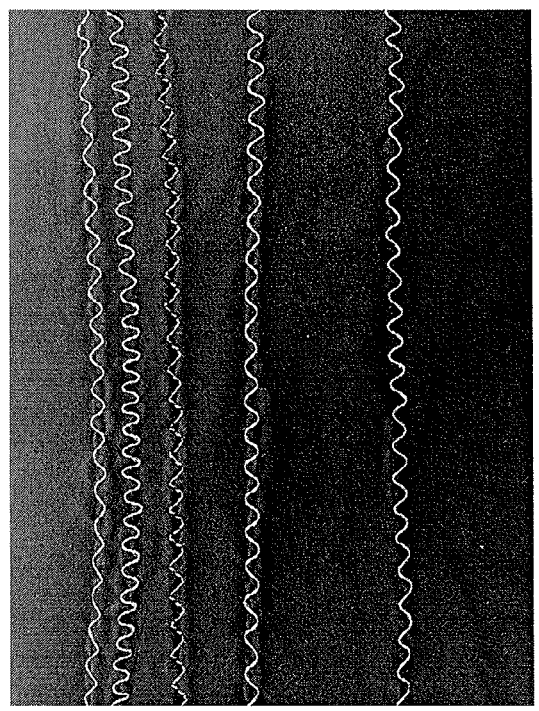
FIGS. 42A-42C illustrate examples of conductive thread sewn into a substrate (e.g., fabric)
Figure 42C:
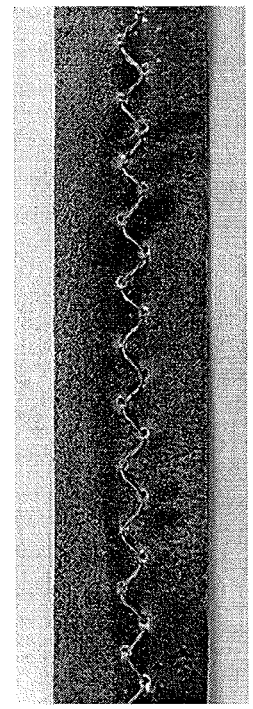
Figure 42B:
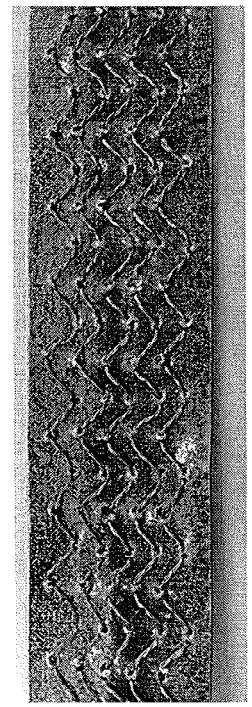

For example, FIGS. 42A-42C show example of conductive threads that are stitched onto a fabric forming a garment that may be used to connect an electrode, sensor or trace formed of a stretchable conductive ink pattern (having an adhesive, gradient region and conductive ink) to a power supply and/or sensing module.

For example in FIGS. 1A-AF, 2A-2B, 3A-3B, etc., the touchpoints and the traces connecting them to a sensor module (sensor manager) may be formed of a stretchable conducive ink composite including a layer of adhesive, an intermediate gradient region and a layer of conductive ink; the trace portion may be insulated, e.g., using a protective resin. The electrode forming the touchpoint portion may be relatively large with the connecting trace being smaller. The trace only needs to extend a short distance. Touchpoint sensors are also somewhat insensitive to stretch of the garment/trace that might change the resistivity of the trace, because the signal from the sensor is a binary signal—e.g., touch or no touch. Similarly, a stretchable conductive ink trace (composite formed into a trace) may be used to connect to EKG electrodes. Typically a conductive ink pattern used as a trace may extend up to 30 cm or less (e.g., 25 cm or less, etc.), although longer traces may be used. Thus, for example, a conductive trace formed of a stretchable conductive ink pattern may be as long as or longer than 25 cm, with a width between 2 mm and up to 10 mm (an average of between about 0.6 to 0.5 mm). The length could be extended while remaining within a target conductivity/resistivity by increasing the thickness of the conductive ink pattern. In some variations it may be desirable to keep the length short. Respiratory sensors may be substantially longer, however, and may up to 22 mm wide, for example.

In some variations it may be useful to use conductive threads or other high-conductivity connectors, such as those shown in FIG. 42A-42C. As described above, this may be used to form a stitched zig-zag connector (also referred to herein as a wire ribbon material). In this example, the conductive thread is stitched onto the garment in a wavy (e.g., zig-zag, sigmoidal, etc.) pattern that allows some stretching in the net direction of the stitching. As described above, respiration (sensors) traces may be formed of stretchable conductive ink patterns to take advantage of the change in conductivity with the change in resistivity with stretching of the conductive ink pattern. In this example, the sewn pattern of threads includes an approximately 35-40 degree zig-zag pattern allowed the stitch to elongate slightly with the fabric. In some example, the conductive thread is a metallic conductive thread. The angle formed at each turning point (in the wavy pattern) and the width of the pattern may depend upon the textile used. In general, the higher the stretchability of the textile, the smaller the angle. The number of threads may vary; in general, any number of threads may be used depending, for example, on the number of sensors and their pins that need to be connected. The threads are typically sewn directly on the garment. The electrical insulation of the thread may be obtained by an external coating on the thread (e.g. silicone, polyester, cotton, etc.) and/or by a layer of insulating adhesive, as described above. The thread connectors may also be used as part of a transfer as described above. For example, a conductive thread may be sewn on a band made on the same fabric of the garment and then transferred by a thermal process to the garment, e.g., using a layer of adhesive.

One or more conductive threads may be applied directly to a fabric (such as a compression garment) or to a transfer (e.g., patch of fabric or other material that is then attached to the garment). Conductive threads may be insulated (e.g., enameled) before being sewn. In some variations the conductive thread may be grouped prior to sewing onto a fabric or other substrate. For example, a plurality (e.g., 2, 3, 4, 5, etc.) of threads may be insulated and wound together, then stitched into a substrate, such as the compression fabric. For example, in one variation, an apparatus includes a garment having an IMU and two EMGs with inputs fed into circuitry (e.g., microchip) on the apparatus, including on a sensor module/manager. The components may be operated on the same electronic 'line', where the line is a plurality of electrically conductive threads that are combined together for stitching through the substrate. In one example, two microchips can be operated by the same 'line' made of 4 wires, where each wire is electrically isolated from each other. In stitching a material, the stitch may be formed of two sets of wires; one on top of the substrate and one beneath the substrate, as is understood from mechanical sewing devices; in some variations a stitch formed of conductive thread may include an upper conductive thread (or group of conductive threads) and a lower conductive thread (or group of conductive threads), where the upper conductive thread(s) is primarily on the upper surface and the lower conductive thread(s) are primarily on the lower surface (but one or either may pass through the substrate to engage with the other).

For example, a conductive thread may include a very fine (e.g., 0.7 millimeters gauge/thickness) 'wire' made of 4 twisted and enameled (thus electrically isolated from each other) wires covered with a binding solution (that is silicon or water based) or protected by a jacket, having a total diameter of about 0.9 millimeters. A conductive wire may be sewn in a wavy (e.g., zig-zag) pattern, such as a pattern having 45 to 90 degrees angles between the legs of the zig-zag, directly on a fabric or substrate. In some example, the pattern is formed on a substrate of material (e.g., fabric) and attached to the garment. For example, the substrate may be a 1 cm to 3 cm self-adhesive strip of fabric.

Sensor Manager/Module

Figure 43A:
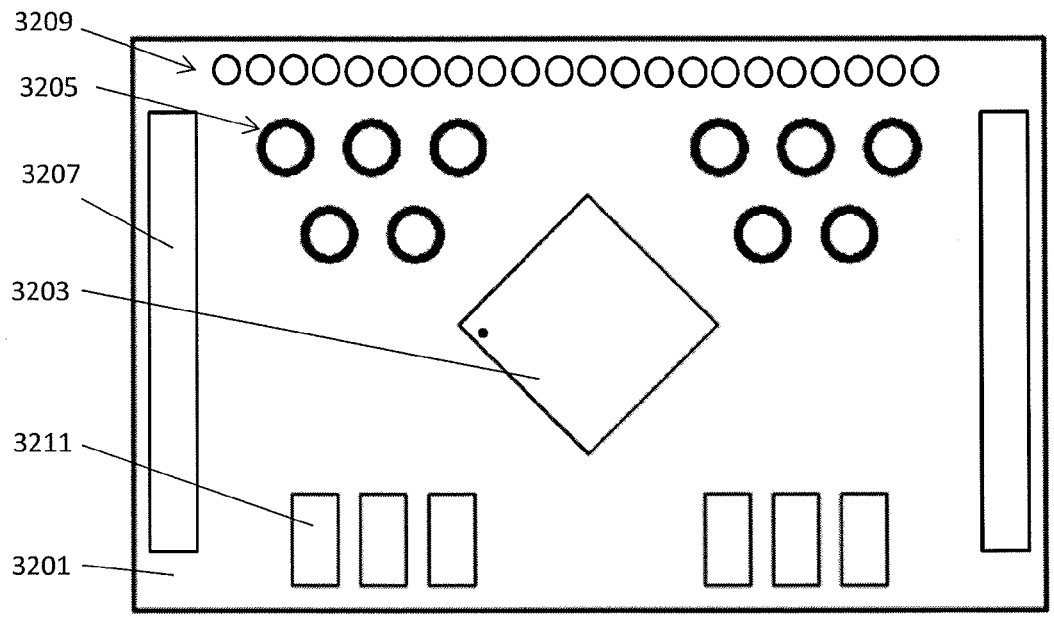
FIG. 43A is a schematic illustration of a SMS module that may be integrated into any of the garments described herein.
Figure 43B:
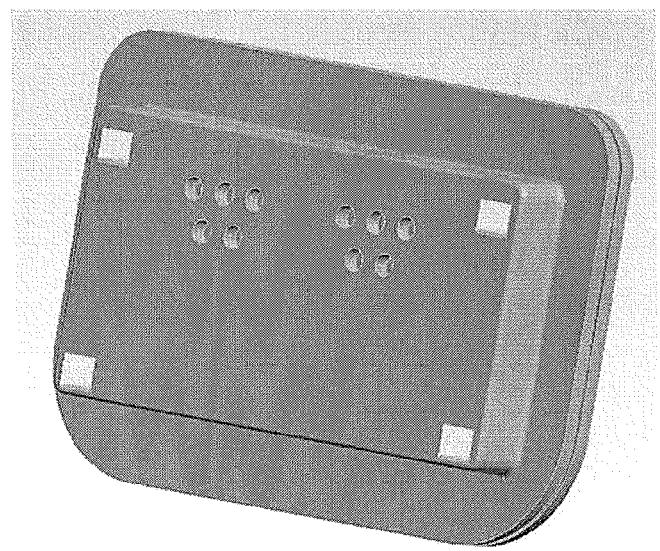
FIG. 43B is an example of a housing for an SMS module such as the one shown in FIG. 43A.

Any of the apparatuses (e.g., garments) described herein may include a sensor manager (SM or SMS), shown schematically in FIG. 43A, that connects the sensors (including electrodes, etc.) on the garment to a processor, including in some variations a smartphone or other mobile device. The sensor manager may be a printed circuit board (PCB) that is part of the sensorized compression garment (e.g., shirt) and may be embedded into a rigid case (as shown in FIG. 43B) placed on the shirt back, e.g., just under the neck as illustrated in FIGS. 1B, 2B, 3B and 4B. It is mainly responsible for collecting and elaborating the data coming from the sensors placed all around the shirt.

As shown in FIG. 43A, the PCB forming the sensor module 3201 may include different elements arranged on the PCB, such as a microcontroller 3203 (e.g., CY8C5 microcontroller (68 pin)) and all the connections with a phone module 3205 (metallized drill), tights 3211 (exposed solderable metal area) and sensors 3207, 3209 (connection with threads).

For example, electrical signals coming from the sensors may be carried by conductive threads sewed onto the shirt fabric or onto a tape (e.g., patch) made of the same material. All of these threads may arrive to the SM PCB and can be connected to it using connectors, or sewed/soldered around metallized drills. In contrast to the SMS illustrated here, an SM architecture in which sensors are connected directly to the Phone module would involve a relatively high number of pins 3205 (e.g., one for each trace/thread coming from the sensors). This may limit the number and type of sensors and could compromise the system stability. The architecture described herein allows connection of traces (e.g., threads) coming from the sensors directly to a microcontroller, using different types of connections (e.g., 3207, 3209) that can be placed on the SM PCB. This way, all the sensors signals may be collected (aggregated) by the microcontroller, which will then communicate the processed data to the mobile processor (e.g., a smartphone) module by using only two pins 3205, for holding a digital UART communication. This solution does not limit the type of number of sensors.

As shown in FIG. 43A above, this schematic shows the female connector for the mobile processor (e.g., smartphone) that may be used. In this example, the Sensor Management System (SMS) may be located in the garment rather than on the module/phone. Thus, the number of pins remains constant even if the number of sensors varies between garments or accessories. For example the numbers of pins may remain constant (e.g., at 10-15) by adapting the specific SMS to generically work with different mobile processors (phones).

Experimental Data

Figure 2A:
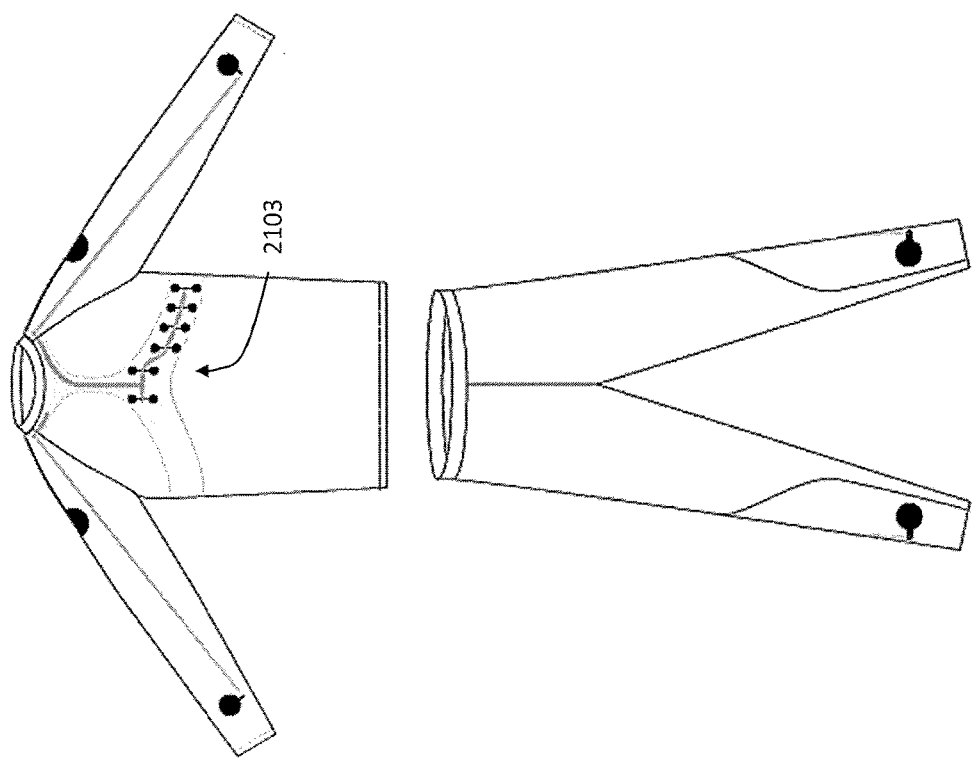
FIG. 2A is a front view of a garment (showing both a shirt and pants) for measuring an ECG.

A garment configured to monitor physiological parameters, including 12-lead ECG detection and respiration was made as described above. The body of the garment was a compression fabric (formed of a compression fabric material) and a 10 ECG electrodes (six chest, one on each arm, and one on each leg) were located as shown in FIG. 2A or 3A. In addition, a respiration sensor, formed of a conductive particle impregnated elastic material, located near the diaphragm when worn, was included. The garment was worn over a subject who was also wearing the standard electrodes for measuring a 12 lead ECG during an activity (stress) test, as well as a mask to measure respiration through the mouth and nose plugs. The patient also wore a support device (inflatable) in the middle of the chest and a support garment (harness) over the shirt, to help keep the electrodes in place against the skin even while performing physical activity.

The patient was asked to pedal against a resistive cycle and measurement were made using standard 12-lead ECG and plethysmography and compared to simultaneous readings made with the garment having integrated sensors as described above. Despite potential interference between the standard leads of the (standard) ECG machine worn under the garment, the physiological monitoring garment described herein performed equivalently or better than then standard (control) devices.

For example, FIG. 48A (on the left) shows ECG results for six leads of the standard 12-lead ECG (I, II, III, aVR, aVL, aVF), and immediately adjacent to these in FIG. 48B, six leads recorded using a garment as described. There was excellent correspondence between the control (reference) device and the garment.

Figure 47A:
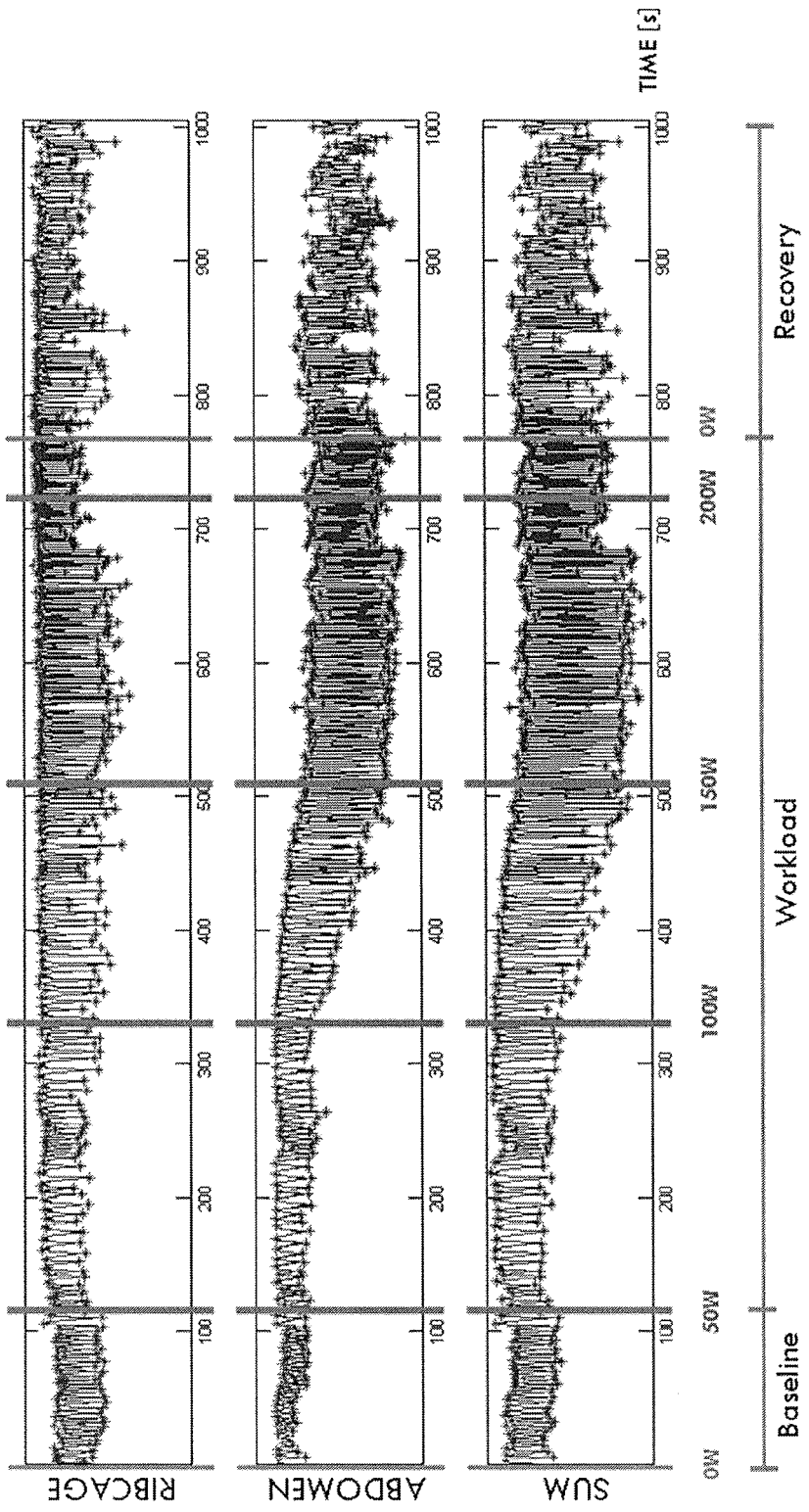
FIG. 47A illustrates measurement of respiration using a garment including a respiration sensors formed from a conductive-particle impregnated elastic strip formed as described herein.

Respiration was also measured from the garment using the respiration sensor, as shown in FIG. 47A. The garment detected noticeable changes in respiration patterns between baseline, workload (pedaling against increasing resistance) and recovery from two regions measured (at the abdomen, and ribcage) from the garment. Comparison was made between standard plethysmography and the garment, and is shown in FIG. 47B. Both techniques measured approximately equivalent breaths per minute during each of the epochs examined.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A garment adapted to monitor a regional respiration of a wearer, the garment comprising:
    a garment body comprising a compression fabric, wherein the garment body is configured as a compression garment;
    a plurality of respiratory sensors arranged on different regions of the garment body, wherein each respiratory sensor comprises an elastic ribbon formed of fabric impregnated with a conductive ink, an electrical connector at each end of the elastic ribbon, and a cover comprising a piece of compression fabric; and
    a sensor module interface located on the garment body, wherein each respiratory sensor connects to the sensor module interface, further wherein the sensor module interface is configured to connect with a sensor manager unit to detect changes in electrical resistance respiratory sensors.

2. The garment of claim 1 wherein the plurality of respiratory sensors comprises six or more respiratory sensors.

3. The garment of claim 1, wherein the plurality of respiratory sensors comprises separately arranged in anterior or posterior, upper or lower, right or left regions of the garment body.

4. The garment of claim 1 configured as a shirt.

5. The garment of claim 1, wherein the respiratory sensors are connected to the sensor module interface via a stitched zig-zag connector formed on a separate piece of compression fabric attached to the garment body.

6. The garment of claim 1, further wherein the respiratory sensors are enclosed in the cover of compression fabric and attached to a surface of the garment body.

7. The garment of claim 1, wherein the respiratory sensors are configured vary the resistance through the sensor as the subject breathes.

8. The garment of claim 1, further comprising a reference line to which each of the respiratory sensors of the plurality of respiratory sensors connects at an end of the respiratory sensor.

9. The garment of claim 1, further comprising at least one ECG electrode on an inner surface of the garment body.

10. The garment of claim 1, further comprising an ECG electrode formed of a conductive ink material on an inner surface of the garment body.

11. The garment of claim 1, further comprising a pocket on the garment body configured to hold a sensor manager unit in connection with the sensor module interface.

12. The garment of claim 1, wherein the plurality of respiratory sensors comprises a first plurality of respiratory sensors on a left side of the garment arranged in parallel and a second plurality of respiratory sensors on a right side of the garment arranged in parallel.

13. The garment of claim 1, further comprising a stitched zig-zag connector formed on a separate piece of compression fabric attached to the garment body, wherein the stitched zig-zag connector comprises a plurality of insulated wires sewn into the separate piece of compression fabric in a sinusoidal or zig-zag pattern, further wherein each respiration sensor of the plurality of respiration sensors connects to an insulated wire in the plurality of insulated wires.

14. The garment of claim 1, wherein each respiratory sensor of the plurality of respiratory sensors is enclosed within the cover comprising the piece of compression fabric and attached to the garment body.

15. The garment of claim 1, wherein each respiration sensor comprises the elastic ribbon impregnated with the conductive ink and less than 10% binder.

* * * * *